United States Patent
Betts

(10) Patent No.: US 11,406,707 B2
(45) Date of Patent: Aug. 9, 2022

(54) STAT3 PHOSPHORYLATION DURING GRAFT-VERSUS-HOST DISEASE

(71) Applicant: H. LEE MOFFITT CANCER CENTER AND RESEARCH INSTITUTE, INC., Tampa, FL (US)

(72) Inventor: Brian Betts, Tampa, FL (US)

(73) Assignee: H. LEE MOFFITT CANCER CENTER AND RESEARCH INSTITUTE, INC., Tampa, FL (US)

( * ) Notice: Subject to any disclaimer, the term of this patent is extended or adjusted under 35 U.S.C. 154(b) by 0 days.

(21) Appl. No.: 15/117,913

(22) PCT Filed: Feb. 10, 2015

(86) PCT No.: PCT/US2015/015174
§ 371 (c)(1),
(2) Date: Aug. 10, 2016

(87) PCT Pub. No.: WO2015/120436
PCT Pub. Date: Aug. 13, 2015

(65) Prior Publication Data
US 2017/0000884 A1    Jan. 5, 2017

Related U.S. Application Data

(60) Provisional application No. 61/937,985, filed on Feb. 10, 2014.

(51) Int. Cl.
| | |
|---|---|
| A61K 39/395 | (2006.01) |
| A61K 31/255 | (2006.01) |
| A61K 31/381 | (2006.01) |
| A61K 45/06 | (2006.01) |
| A61K 31/506 | (2006.01) |
| A61K 31/436 | (2006.01) |
| G01N 33/569 | (2006.01) |
| G01N 33/68 | (2006.01) |
| A61K 39/00 | (2006.01) |
| C07K 16/24 | (2006.01) |
| A61K 38/20 | (2006.01) |

(52) U.S. Cl.
CPC ........ *A61K 39/3955* (2013.01); *A61K 31/255* (2013.01); *A61K 31/381* (2013.01); *A61K 31/436* (2013.01); *A61K 31/506* (2013.01); *A61K 38/2013* (2013.01); *A61K 45/06* (2013.01); *C07K 16/248* (2013.01); *G01N 33/56972* (2013.01); *G01N 33/6893* (2013.01); *A61K 2039/505* (2013.01); *C07K 2317/24* (2013.01); *C07K 2317/76* (2013.01); *G01N 2333/4706* (2013.01); *G01N 2440/14* (2013.01); *G01N 2800/245* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | | |
|---|---|---|---|---|
| 5,204,329 | A * | 4/1993 | Ackerman | A61K 31/47 514/20.5 |
| 7,960,434 | B2 | 6/2011 | Turkson et al. | |
| 2005/0049299 | A1 | 3/2005 | Aggarwal | |
| 2006/0247318 | A1 | 11/2006 | Song et al. | |
| 2009/0011456 | A1 | 1/2009 | Smith et al. | |
| 2009/0069420 | A1* | 3/2009 | Turkson | A61K 31/00 514/518 |
| 2011/0124602 | A1 | 5/2011 | Turkson et al. | |
| 2011/0172429 | A1 | 7/2011 | Asai et al. | |
| 2011/0201576 | A1 | 8/2011 | Turkson et al. | |
| 2011/0212911 | A1 | 9/2011 | Li et al. | |
| 2011/0223661 | A1 | 9/2011 | Turkson et al. | |
| 2011/0312984 | A1 | 12/2011 | Tweardy et al. | |
| 2011/0319362 | A1 | 12/2011 | Wang et al. | |
| 2012/0252763 | A1 | 10/2012 | Li et al. | |

OTHER PUBLICATIONS

AlphaScreen® SureFire STAT3 (p-Tyr705) Assay Kits Manual from Perkin Elmer (Nov. 2010).*
Lu et al. (Blood. Dec. 15, 2008; 112(13): 5254-5258 and Document S1).*
Antin, J.H, et al. Cytokine dysregulation and acute graft-versus-host disease. Blood. 1992 80(12):2964-8.
Betts BC, et al. Anti-IL6-receptor-alpha (tocilizumab) does not inhibit human monocyte-derived dendritic cell maturation or alloreactive T-cell responses. Blood. 2011 118(19):5340-3. Epub Sep. 22, 2011.
Betts BC, et al. STAT5 polarization promotes iTregs and suppresses human T-cell alloresponses while preserving CTL capacity. J Leukoc Biol. 2014 95(2):205-13. Epub Sep. 25, 2013.
Betts, et al., Janus kinase-2 inhibition induces durable tolerance to alloantigen by human dendritic cell-stimulated T cells yet preserves immunity to recall antigen. Blood. 2011 118(19):5330-9. Epub Sep. 13, 2011.
Broady, et al., Cutaneous GVHD is associated with the expansion of tissue-localized Th1 and not Th17 cells. Blood. 2010 116(25):5748-51. Epub Sep. 23, 2010.
Carlson, M.J., et al. Panoskaltsis-Mortari, B.R. Blazar, and J.S. Serody. 2009. In vitro-differentiated TH17 cells mediate lethal acute graft-versus-host disease with severe cutaneous and pulmonary pathologic manifestations. Blood. 2009 113(6):1365-74. Epub Oct. 28, 2008.

(Continued)

*Primary Examiner* — Bong-Sook Baek
(74) *Attorney, Agent, or Firm* — Meunier Carlin & Curfman LLC

(57) ABSTRACT

Compositions and methods to reduce the risk of graft versus host disease (GVHD) in a subject receiving hematopoietic stem cell transplantation (HSCT). Also disclosed are methods for identifying patients receiving HSCT who are at risk for developing GVHD, methods for prognosing the severity of GVHD in a subject receiving HSCT, and methods for monitoring efficacy of a therapeutic for treatment of GVHD in a subject HSCT.

12 Claims, 28 Drawing Sheets

Specification includes a Sequence Listing.

(56) References Cited

OTHER PUBLICATIONS

Couto, JP, et al., AZD1480 blocks growth and tumorigenesis of RET-activated thyroid cancer cell lines. PLoS One. 2012 7(10):e46869. Epub Oct. 2, 2012.

Das R, et al. Blockade of interleukin-23 signaling results in targeted protection of the colon and allows for separation of graft-versus-host and graft-versus leukemia responses. Blood. 2010 115(25):5249-58. Epub Apr. 9, 2010.

Faber LM, et al., Generation of leukemia-reactive cytotoxic T lymphocyte clones from the HLA-identical bone marrow donor of a patient with leukemia. J Exp Med. 1992 176(5):1283-9.

Fine JP, et al., A Proportional Hazards Model for the Subdistribution of a Competing Risk. Journal of the American Statistical Association. 1999 94:496-509.

Fulton LM, et al., Attenuation of acute graft-versus-host disease in the absence of the transcription factor RORγt. J Immunol. 2012 189(4):1765-72. Epub Jul. 9, 2012.

Geiger TL, et al., Nfil3 is crucial for development of innate lymphoid cells and host protection against intestinal pathogens. J Exp Med. 2014 211(9):1723-31. Epub Aug. 11, 2014.

Griffiths CE, et al., Comparison of ustekinumab and etanercept for moderate-to-severe psoriasis. N Engl J Med. 2010 362(2):118-28.

Hedrich CM, et al., Stat3 promotes IL-10 expression in lupus T cells through trans-activation and chromatin remodeling. Proc Natl Acad Sci U S A. 2014 111(37):13457-62. Epub Sep. 3, 2014.

Honda T, et al., Design and synthesis of 2-cyano-3,12-dioxoolean-1,9-dien-28-oic acid, a novel and highly active inhibitor of nitric oxide production in mouse macrophages. Bioorg Med Chem Lett. 1998 8(19):2711-4.

Honda T, et al., Synthetic oleanane and ursane triterpenoids with modified rings A and C: a series of highly active inhibitors of nitric oxide production in mouse macrophages. J Med Chem. 2000 43(22):4233-46.

Iclozan C, et al., T helper17 cells are sufficient but not necessary to induce acute graft-versus-host disease. Biol Blood Marrow Transplant. 2010 16(2):170-8. Epub Oct. 2, 2009.

Kappel LW, et al., IL-17 contributes to CD4-mediated graft-versus-host disease. Blood. 2009 113(4):945-52. Epub Oct. 17, 2008.

Keijsers RR, et al., In vivo induction of cutaneous inflammation results in the accumulation of extracellular trap-forming neutrophils expressing RORγt and IL-17. J Invest Dermatol. 2014 134(5):1276-84. Epub Dec. 6, 2013.

Kim HY, et al, Interleukin-17-producing innate lymphoid cells and the NLRP3 inflammasome facilitate obesity-associated airway hyperreactivity. Nat Med. 2014 20(1):54-61. Epub Dec. 15, 2013.

Konoike, T. et al., Practical Partial Synthesis of Myriceric Acid A, an Endothelin Receptor Antagonist, from Oleanolic Acid. J Org. Chem, 1997 62:960-966.

Kurebayashi Y, et al., PI3K-Akt-mTORC1-S6K½ axis controls Th17 differentiation by regulating Gfi1 expression and nuclear translocation of RORγ. Cell Rep. 2012 1(4):360-73. Epub Mar. 29, 2012.

Laurence A, et al., Interleukin-2 signaling via STAT5 constrains T helper 17 cell generation. Immunity. 2007 26(3):371-81.

Laurence A, et al., STAT3 transcription factor promotes instability of nTreg cells and limits generation of iTreg cells during acute murine graft-versus-host disease. Immunity. 2012 37(2):209-22.

Levine JE, et al., Graft-versus-host disease treatment: predictors of survival. Biol Blood Marrow Transplant. 2010 16(12):1693-9. Epub Jun. 9, 2010.

Lin AM, et al., Mast cells and neutrophils release IL-17 through extracellular trap formation in psoriasis. J Immunol. 2011 187(1):490-500. Epub May 23, 2011.

Lin JX, et al., Critical Role of STAT5 transcription factor tetramerization for cytokine responses and normal immune function. Immunity. 2012 36(4):586-99.

Littman, DR, et al., Th17 and regulatory T cells in mediating and restraining inflammation. Cell. 2010 140(6):845-58.

Liu W, et al., CD127 expression inversely correlates with FoxP3 and suppressive function of human CD4+ T reg cells. J Exp Med. 2006 203(7):1701-11. Epub Jul. 3, 2006.

Longman RS, et al., $CX_3CR1^+$ mononuclear phagocytes support colitis-associated innate lymphoid cell production of IL-22. J Exp Med. 2014 211(8):1571-83. Epub Jul. 14, 2014.

Lord JD, et al., Blood and gastric FOXP3+ T cells are not decreased in human gastric graft-versus-host disease. Biol Blood Marrow Transplant. 2011 17(4):486-96. Epub Sep. 24, 2010.

Lozza L, et al., The strength of T cell stimulation determines IL-7 responsiveness, secondary expansion, and lineage commitment of primed human CD4+IL-7Rhi T cells. Eur J Immunol. 2008 38(1):30-9.

Lu SX, et al., STAT-3 and ERK ½ phosphorylation are critical for T-cell alloactivation and graft-versus-host disease. Blood. 2008 112(13):5254-8. Epub Oct. 6, 2008.

Matsuoka K, et al., Low-dose interleukin-2 therapy restores regulatory T cell homeostasis in patients with chronic graft-versus-host disease. Sci Transl Med. 2013 5(179):179ra43.

Miyao T, et al., Plasticity of Foxp3(+) T cells reflects promiscuous Foxp3 expression in conventional T cells but not reprogramming of regulatory T cells. Immunity. 2012 36(2):262-75. Epub Feb. 9, 2012.

Munneke JM, et al, Activated innate lymphoid cells are associated with a reduced susceptibility to graft-versus-host disease. Blood. 2014 124(5):812-21. Epub May 22, 2014.

Pidala J, et al., Ustekinumab demonstrates activity in glucocorticoid-refractory acute GVHD. Bone Marrow Transplant. 2012 47(5):747-8. Epub Aug. 29, 2011.

Pidala J, et al., A randomized phase II study to evaluate tacrolimus in combination with sirolimus or methotrexate after allogeneic hematopoietic cell transplantation. Haematologica. 2012 97(12):1882-9. Epub Jun. 11, 2012.

Pipkin ME, et al., Interleukin-2 and inflammation induce distinct transcriptional programs that promote the differentiation of effector cytolytic T cells. Immunity. 2010 32(1):79-90. Epub Jan. 21, 2010.

Przepiorka D, et al., 1994 Consensus Conference on Acute GVHD Grading. Bone Marrow Transplant. Jun. 1995;15(6):825-8.

Radojcic V, et al., STAT3 signaling in CD4+ T cells is critical for the pathogenesis of chronic sclerodermatous graft-versus-host disease in a murine model. J Immunol. 2010 184(2):764-74. Epub Dec. 7, 2009.

Ratajczak P, et al., Th17/Treg ratio in human graft-versus-host disease. Blood. 2010 116(7):1165-71. Epub May 18, 2010.

Ratajewski M, et al., Upstream stimulating factors regulate the expression of RORγT in human lymphocytes. J Immunol. 2012 189(6):3034-42. Epub Aug. 13, 2012.

Rautio J, et al., Prodrugs: design and clinical applications. Nat Rev Drug Discov. 2008 7(3):255-70.

Rubio V, et al., Ex vivo identification, isolation and analysis of tumor-cytolytic T cells. Nat Med. 2003 9(11):1377-82. Epub Oct. 5, 2003.

Samarasinghe S, et al., Functional characterization of alloreactive T cells identifies CD25 and CD71 as optimal targets for a clinically applicable allodepletion strategy. Blood. 2010 115(2):396-407. Epub Nov. 4, 2009.

Seddiki N, et al., Expression of interleukin (IL)-2 and IL-7 receptors discriminates between human regulatory and activated T cells. J Exp Med. 2006 203(7):1693-700. Epub Jul. 3, 2006.

Siddiquee K, et al., Selective chemical probe inhibitor of Stat3, identified through structure-based virtual screening, induces antitumor activity. Proc Natl Acad Sci U S A. 2007 104(18):7391-6. Epub Apr. 26, 2007.

Toichi E, et al., An anti-IL-12p40 antibody down-regulates type 1 cytokines, chemokines, and IL-12/IL-23 in psoriasis. J Immunol. 2006 177(7):4917-26.

Toker A, et al., Active demethylation of the Foxp3 locus leads to the generation of stable regulatory T cells within the thymus. J Immunol. 2013 190(7):3180-8. Epub Feb. 18, 2013.

Tonel G, et al., Cutting edge: A critical functional role for IL-23 in psoriasis. J Immunol. 2010 185(10):5688-91. Epub Oct. 18, 2010.

Ueda A, et al., Fyn promotes Th17 differentiation by regulating the kinetics of RORγt and Foxp3 expression. J Immunol. 2012 188(11):5247-56. Epub Apr. 25, 2012.

(56) References Cited

OTHER PUBLICATIONS

Veerapathran A, et al., Human regulatory T cells against minor histocompatibility antigens: ex vivo expansion for prevention of graft-versus-host disease. Blood. 2013 122(13):2251-61. Epub Aug. 1, 2013.

Veerapathran A, et al., Ex vivo expansion of human Tregs specific for alloantigens presented directly or indirectly. Blood. 2011 118(20):5671-80. Epub Sep. 23, 2011.

Warren EH, et al., Cytotoxic T-lymphocyte-defined human minor histocompatibility antigens with a restricted tissue distribution. Blood. Mar. 15, 1998;91(6):2197-207.

Yu Y, et al., Prevention of GVHD while sparing GVL effect by targeting Th1 and Th17 transcription factor T-bet and RORgammat in mice. Blood. 2011 118(18):5011-20. Epub Aug. 19, 2011.

Zeiser R, et al., Differential impact of mammalian target of rapamycin inhibition on CD4+CD25+Foxp3+ regulatory T cells compared with conventional CD4+ T cells. Blood. 2008 111(1):453-62. Epub Oct. 29, 2007.

Zeng ZZ, et al., 5(S)-hydroxyeicosatetraenoic acid stimulates DNA synthesis in human microvascular endothelial cells via activation of Jak/STAT and phosphatidylinositol 3-kinase/Akt signaling, leading to induction of expression of basic fibroblast growth factor 2. J Biol Chem. 2002 277(43):41213-9. Epub Aug. 21, 2002.

International Search Report and Written Opinion in PCT/US2015/015174 dated Jun. 22, 2015.

\* cited by examiner

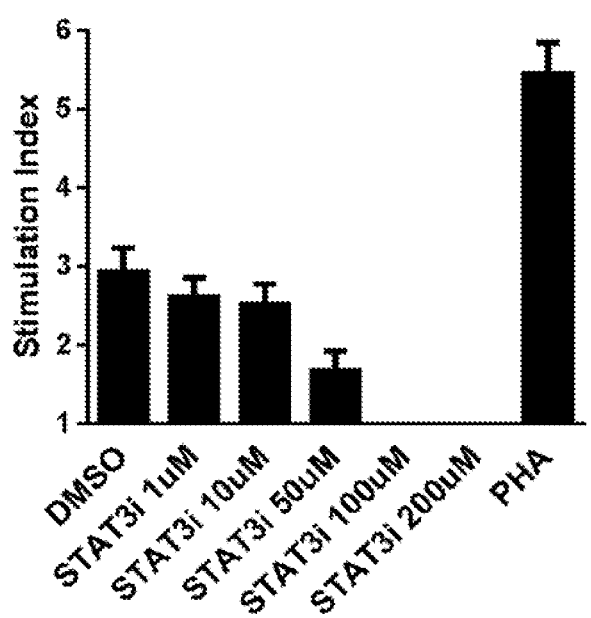
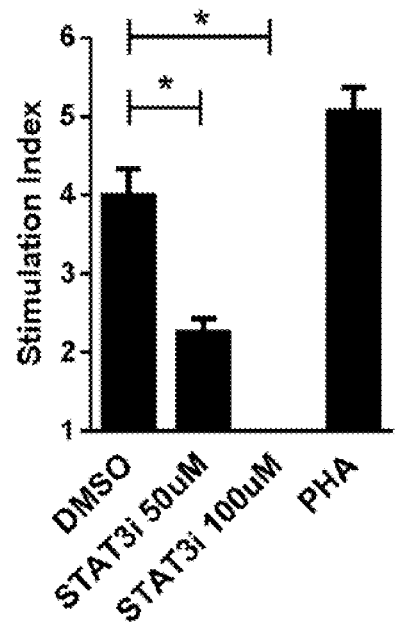
FIGURE 1A    FIGURE 1B
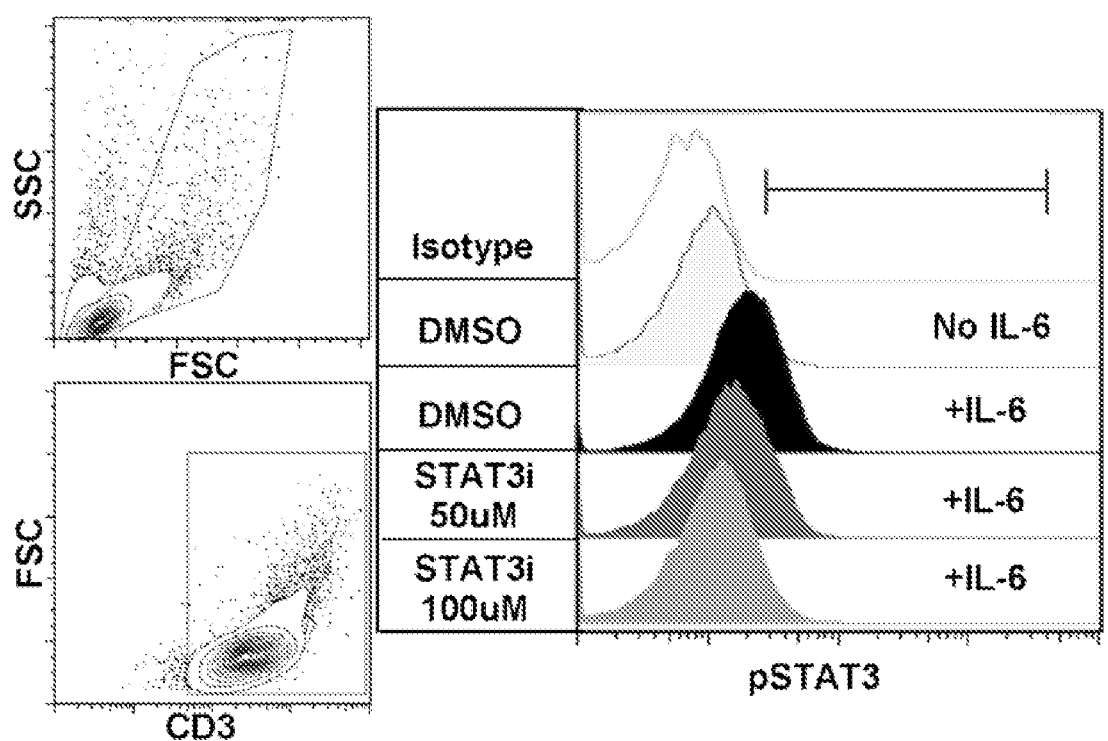
FIGURE 1C

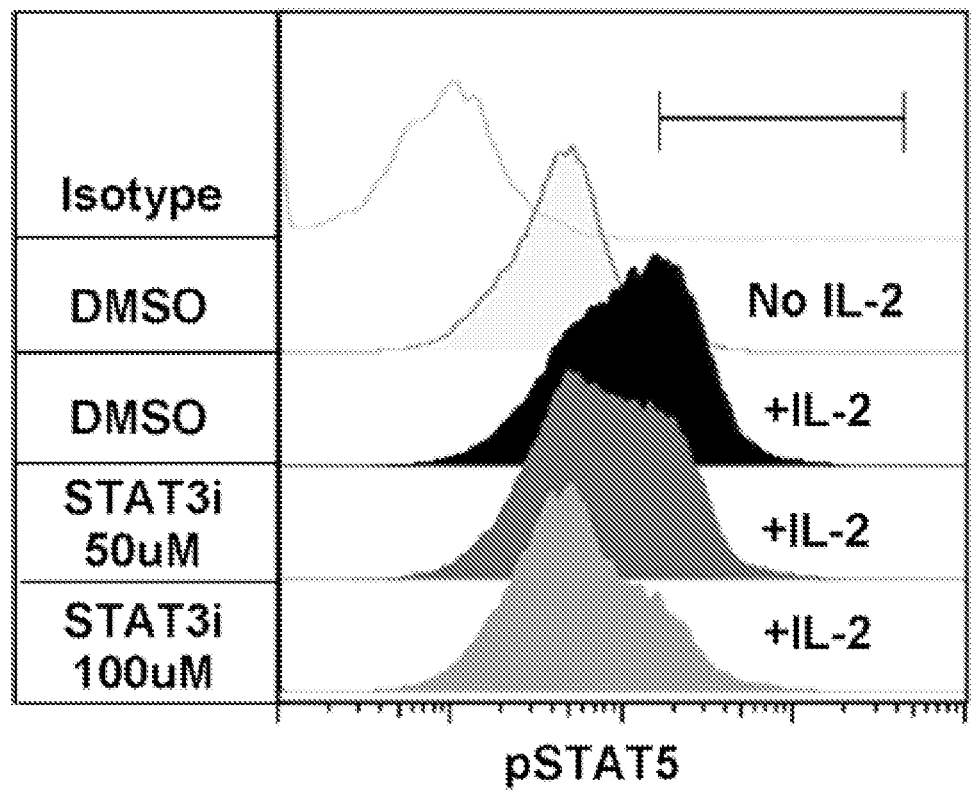
FIGURE 1D
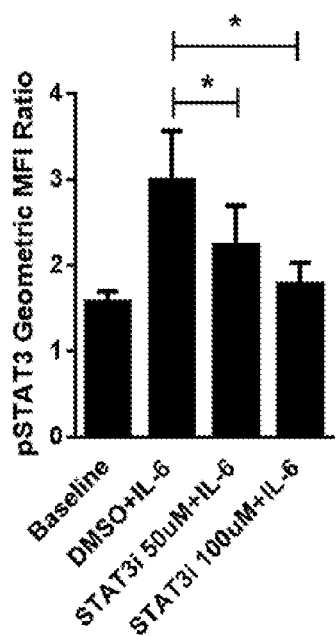 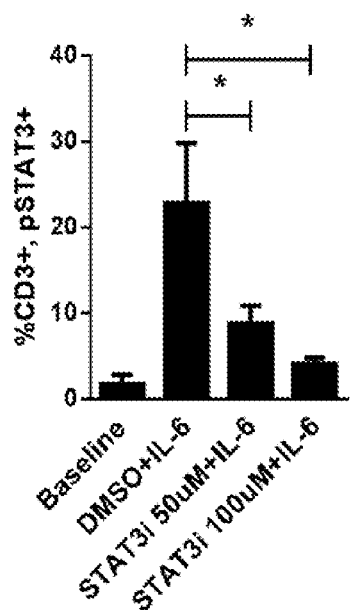
FIGURE 1E　　　　　　FIGURE 1F

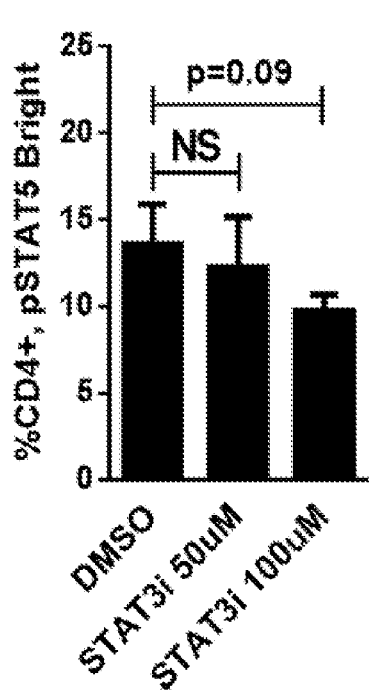
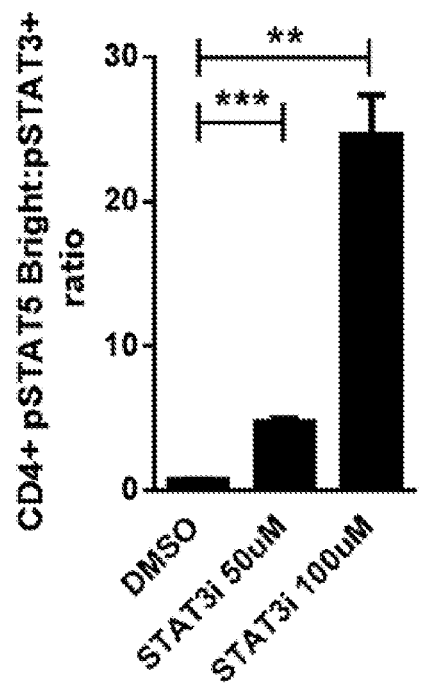
FIGURE 2E          FIGURE 2F
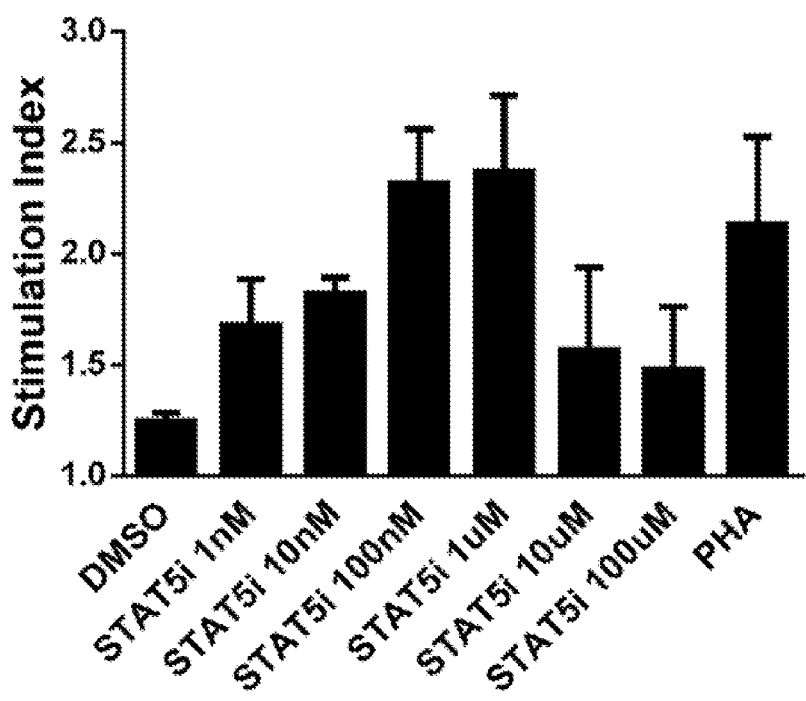
FIGURE 3A

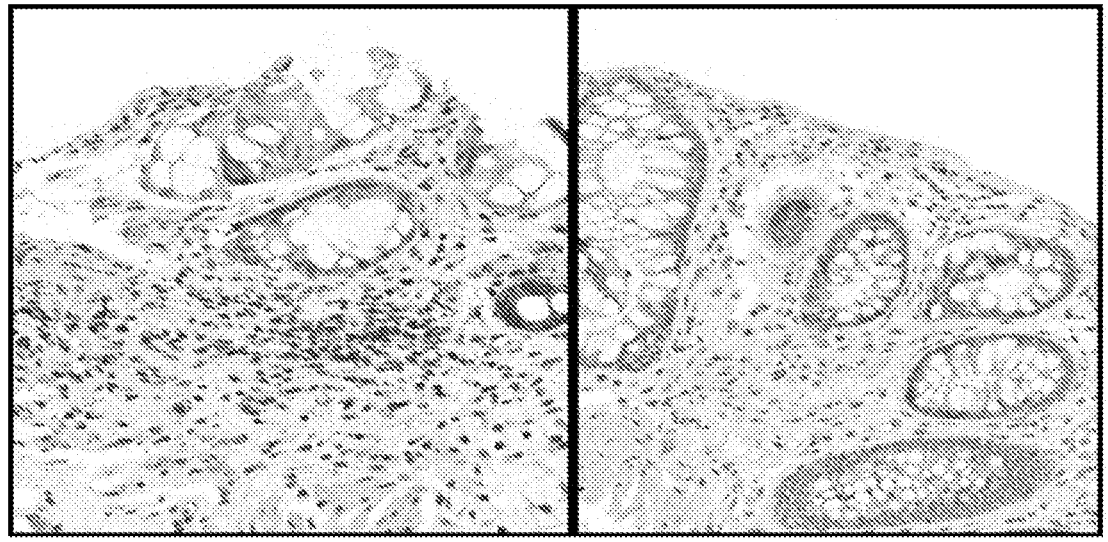
FIGURE 12A  FIGURE 12B
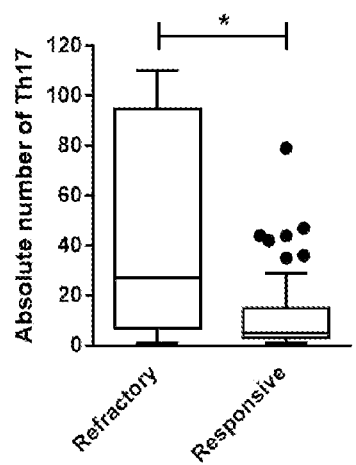 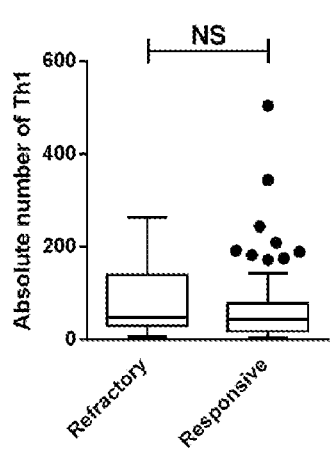 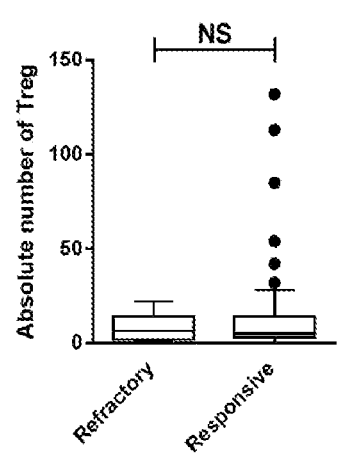
FIGURE 12C  FIGURE 12D  FIGURE 12E

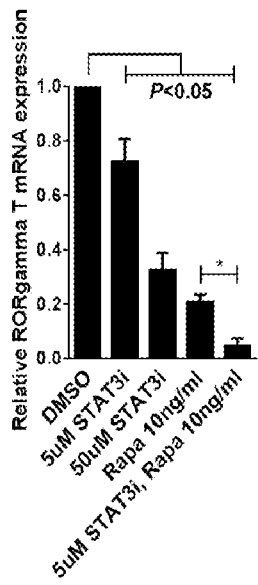 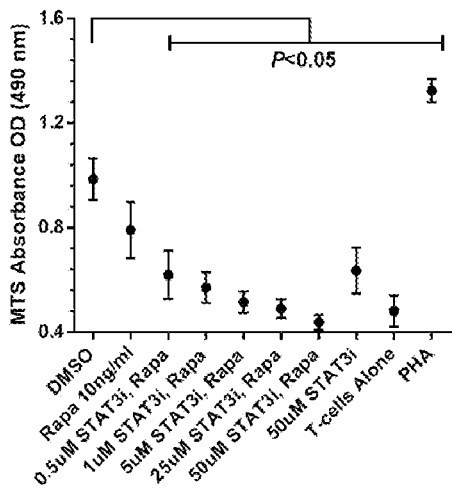 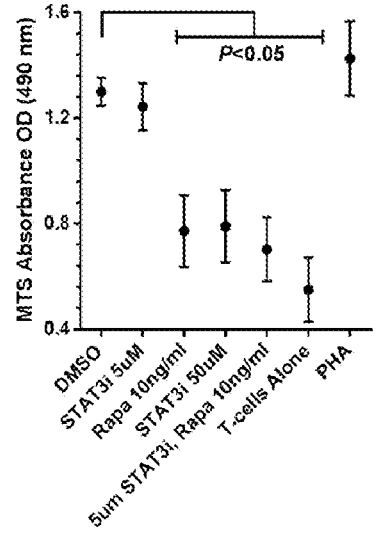
FIGURE 14A    FIGURE 14B    FIGURE 14C
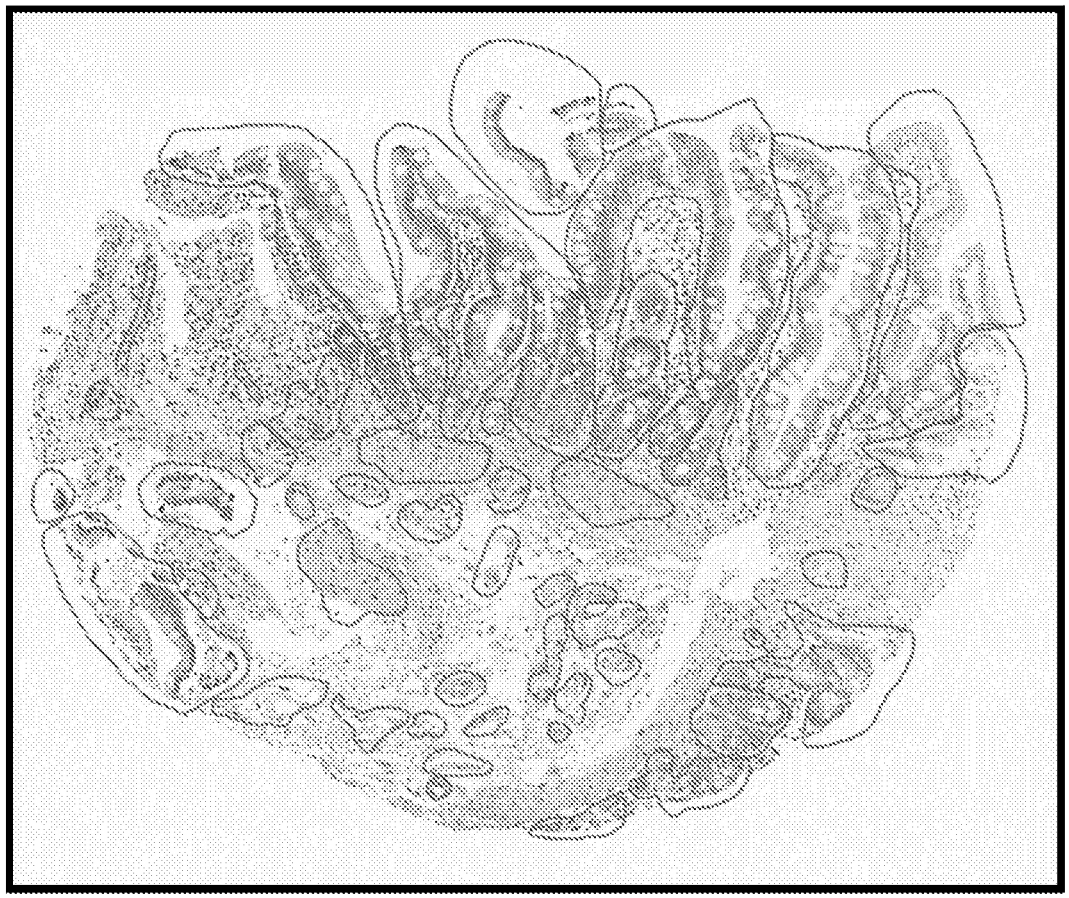
FIGURE 15

STAT3 PHOSPHORYLATION DURING GRAFT-VERSUS-HOST DISEASE

CROSS-REFERENCE TO RELATED APPLICATIONS

This application claims benefit of U.S. Provisional Application No. 61/937,985 filed Feb. 10, 2014, which is hereby incorporated herein by reference in its entirety.

STATEMENT REGARDING FEDERALLY SPONSORED RESEARCH

This invention was made with Government support under Grant No. CA132197 awarded by the National Institutes of Health. The Government has certain rights in the invention.

BACKGROUND

Hematopoietic stem cell transplantation (HSCT) is the transplantation of multipotent hematopoietic stem cells, usually derived from bone marrow, peripheral blood, or umbilical cord blood. It is a medical procedure in the fields of hematology and oncology, most often performed for patients with certain cancers of the blood or bone marrow, such as multiple myeloma or leukemia. In these cases, the recipient's immune system is usually destroyed with radiation or chemotherapy before the transplantation. Allogeneic HSC donors must have a tissue (HLA) type that matches the recipient. Matching is performed on the basis of variability at three or more loci of the HLA gene, and a perfect match at these loci is preferred. However, even if there is a good match at these critical alleles, alloreactivity can negatively influence outcomes of HSCT from allogeneic donors.

Graft versus host disease (GVHD) is an inflammatory disease that is peculiar to allogeneic transplantation. It is an attack of the "new" bone marrow's immune cells against the recipient's tissues. This can occur even if the donor and recipient are HLA-identical because the immune system can still recognize other differences between their tissues. It is aptly named graft-versus-host disease because bone marrow transplantation is the only transplant procedure in which the transplanted cells must accept the body rather than the body accepting the new cells. Acute graft-versus-host disease typically occurs in the first 3 months after transplantation and may involve the skin, intestine, or the liver. High-dose corticosteroids such as prednisone are a standard treatment; however this immuno-suppressive treatment often leads to deadly infections. Chronic graft-versus-host disease may also develop after allogeneic transplant. It is the major source of late treatment-related complications, although it less often results in death. In addition to inflammation, chronic graft-versus-host disease may lead to the development of fibrosis, or scar tissue, similar to scleroderma; it may cause functional disability and require prolonged immunosuppressive therapy.

GVHD is usually mediated by alloreactive T helper ($T_H$) cells, which react to foreign peptides presented on the MHC of the host. In particular, T helper 17 cells ($T_H17$) are a subset of pathogenic T helper cells producing interleukin 17 (IL-17) that play a key role in autoimmune disease. In contrast, regulatory T cells (Treg) are a subpopulation of T cells which modulate the immune system, maintain tolerance to self-antigens, and abrogate autoimmune disease. Since standard pharmacologic immune suppression impairs all T-cell function, it jeopardizes the beneficial reconstitution of regulatory T-cells (Treg). Therefore, needed are immune suppression agents that more selectively control alloresponses after transplantation.

SUMMARY

Compositions and methods to reduce the risk of graft versus host disease (GVHD) in a subject receiving hematopoietic stem cell transplantation (HSCT) are described. The method can involve administering to the subject an inhibitor of STAT3 (signal transducer and activator of transcription), which is highly expressed in alloreactive T-cells. The method can also involve administering to the subject a mammalian receptor of rapamycin (mTOR) inhibitor. The method can also involve administering to the subject a therapeutically effective amount of tacrolimus. The method can also involve administering to the subject a therapeutically effective amount of IL-2.

Also disclosed are methods for identifying patients receiving HSCT who are at risk for developing GVHD. The methods generally involve assaying for STAT3 phosphorylation (e.g., Y705) within $CD4^+$ T-cells from the patient. The $CD4^+$ T-cells can also be pulsed with IL-6 prior to the immunoassay to stimulate STAT3 phosphorylation.

Also disclosed are methods for prognosing the severity of GVHD in a subject receiving HSCT, and methods for monitoring efficacy of a therapeutic for treatment of GVHD in a subject receiving HSCT. These methods generally involve assaying a biological sample from the patient for detection of T-helper 17 ($T_H17$) cells. In some embodiments, tissue-resident $T_H17$ cells is an indication of pathological grade of GVHD, and a reduction in $T_H17$ cells after treatment is an indication of therapeutic efficacy.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 12. Tissue-resident Th17 cells are increased in the target-organs of those with steroid-refractory acute GVHD. (A) shows increased RORgamma positive lymphocytes in the lamina propria from a rectal biopsy. The panel A patient was diagnosed with pathologic grade 3 GVHD and was refractory to steroid therapy. (B) shows fewer RORgamma positive lymphocytes in the lamina propria on rectal biopsy. The panel B patient was diagnosed with pathologic grade 2 GVHD in the rectum and was responsive to steroid therapy. [RORgamma, ×400]. Box and whisker plots show absolute number of tissue-resident Th17 (C), Th1 (D), and Treg (E) by response to corticosteroid therapy. Line depicts median. NS=not significant, *P<0.05.

FIG. 14. Dual STAT3/mTOR inhibition exerts enhanced control over RORgammaT and alloreactivity. (A) Purified CD4+ T-cells were stimulated with allogeneic moDCs for 5 days with DMSO, rapamycin (10 ng/ml), STAT3i (5 or 5 uM), or both inhibitors. Media was supplemented with IL-6, TGF-beta, and anti-IFN-gamma mAb to enhance RORgammaT detection. Bar graph depicts the triplicate means±SEM from 3 independent experiments evaluating the relative RORgammaT expression in response to mTOR, STAT3, or dual pathway blockade. (B) 5-day alloMLRs (DC:T-cell ratio 1:30) treated with a fixed dose of rapamycin (10 ng/ml) with or without varying concentrations of STAT3i (500 nM-50 uM), or DMSO diluent control, with all drugs added once on day 0. T-cell proliferation was measured by a colorimetric assay. Bar graph shows the triplicate means±SEM of the optical density (OD analyzed at 490 nm) from 4 independent experiments. (C) Untreated primary 5-day alloMLR, followed by 3-day restimulation with first-party allogeneic moDCs in the presence of rapamycin (10 ng/ml) with or without STAT3i (5 or 50 uM), or DMSO diluent control, with all drugs added once on day 0. T-cell proliferation was measured by a colorimetric assay. Bar graph shows the triplicate means±SEM of the optical density (490 nm) from 3 independent experiments. *P<0.05.

FIG. 15. Representative biopsy image demonstrating negative pen exclusion of non-scored sections, including the epithelium, to exclude nonspecific staining of ROR or IL-17.

DETAILED DESCRIPTION

Figure 1G:
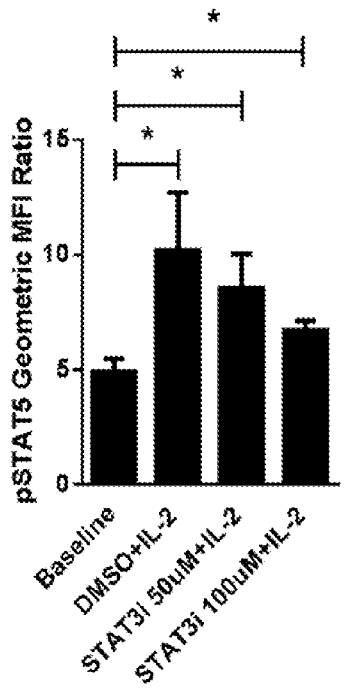
FIG. 1. Selective STAT3 inhibition impaired DC-allosensitized T-cell responses. (A) Dose response of S3I-201 (STAT3 inhibitor, 0-200 µM) in human allo-MLRs (DC:T cell ratio 1:30) treated once on day 0 with drug or DMSO diluent control, with a readout of T-cell proliferation on day 5. (B) Suppression of responder T-cell proliferation was confirmed in subsequent allo-MLRs exposed to S3I-201 (50 or 100 µM) or DMSO once on day 0, in identical culture conditions. T-cell proliferation was determined by a colorimetric assay on day 5. The stimulation index was calculated by dividing the OD of the allo-MLR by the OD of T cells alone. PHA-stimulated T cells served as the positive control. The stimulation index is an average of triplicate means from 3 independent experiments±sem. (C, D) Representative contour plots demonstrate gating strategy of $CD3^+$ T cells and histograms show on-target inhibition of IL-6/STAT3 phosphorylation, paired with intact IL-2/STAT5 activation in cytokinepulsed T cells. Gates in (C) and (D) define the $CD3^+$, $pSTAT3^+$ and $CD3^+$, $pSTAT5^{Bright}$ T cells, respectively. (E, G) Geometric MFI ratio of STAT3 or -5 phosphorylation and (F, H) percentage of STAT3 or bright STAT5 phosphorylation in DMSO- or S3I-201-treated T cells pulsed with IL-6 or -2, respectively, ±SD from 4 independent experiments. The geometric MFI ratio was calculated by dividing the geometric MFI of the cytokine-pulsed cells by the geometric MFI of the corresponding fluorochrome isotype.*P<0.05, **P=0.001-0.01, paired t test.
Figure 1H:
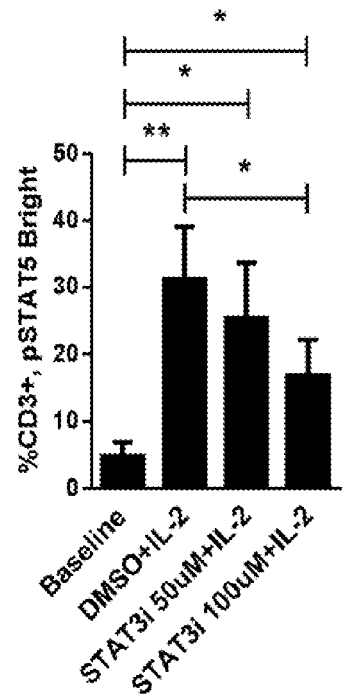

STAT3 (signal transducer and activator of transcription 3) activation of CD4+ T-cells is disclosed herein to be increased in allogeneic hematopoietic stem cell transplantation (HSCT) recipients that eventually develop acute GVHD. STAT3 phosphorylation is detectable early post-transplant, even when the clinical syndrome is not yet recognized. Interestingly, $T_H17$ cells significantly accumulate within the target-organ tissues of those diagnosed with severe acute GVHD. The STAT3-RORgammaT axis is shown herein to be an evaluable indicator of acute GVHD onset and therapy response to corticosteroids. Furthermore, mammalian receptor of rapamycin (mTOR) blockade with rapamycin is shown herein to reduce the burden of tissue-resident $T_H17$, and rapamycin-resistance among allo-responders is shown to be overcome with selective inhibition of STAT3.

Selective small molecule inhibitors of STAT3 (e.g., S3I-201) are shown herein to suppress human DC-allosensitized T-cell proliferation and abrogate $T_H17$ responses, but permit IL-2-driven, STAT5-dependent Treg differentiation from naïve CD4+ precursors. CD8+ cytolytic effector function remains intact despite STAT3 deprivation. In some embodiments, STAT3 inhibition polarizes the ratio of STAT phosphorylation in favor of STAT5 over STAT3. Conversely, selective impairment of STAT5 phosphorylation markedly reduced the ratio of Tregs to alloreactive effectors. STAT3 therefore represents a relevant target to achieve control over alloresponses after transplantation, by augmenting the STAT5:STAT3 phosphorylation ratio in donor T-cells.

Disclosed are methods for identifying patients receiving HSCT who are at risk for developing acute GVHD. The methods involve assaying for STAT3 phosphorylation within CD4+ T-cells in a biological sample (e.g., peripheral blood mononuclear cells (PBMC) from heparinized peripheral blood) from the patient. In particular, the method can comprise detecting phosphorylated STAT3 Y705. The CD4+ T-cells can be pulsed with IL-6 prior to the immunoassay to stimulate STAT3 phosphorylation.

In some embodiments, a detection of STAT3 phosphorylation in at least 45%, 46%, 47%, 48%, 49%, or 50% of the CD4+ T-cells is an indication that the patient will develop GVHD, e.g., grade II-IV GVHD, i.e., has a 90%, 91%, 92%, 93%, 94%, 95%, 96%, 97%, 98%, 99%, or 100% likelihood of developing GVHD. Likewise, a detection of less than 45%, 46%, 47%, 48%, 49%, or 50% is an indication that the patient is not likely to develop GVHD, i.e., has only a 1%, 2%, 3%, 4%, 5%, 6%, 7%, 8%, 9%, 10%, 11%, 12%, 13%, 14%, or 15% likelihood of developing GVHD.

STAT3 phosphorylation in $CD4^+$ T-cells can be assayed using routine immunoassay methods. Examples of immunoassays are enzyme linked immunosorbent assays (ELISAs), radioimmunoassays (RIA), radioimmune precipitation assays (RIPA), immunobead capture assays, Western blotting, dot blotting, gel-shift assays, Flow cytometry, protein arrays, multiplexed bead arrays, magnetic capture, in vivo imaging, fluorescence resonance energy transfer (FRET), and fluorescence recovery/localization after photobleaching (FRAP/FLAP).

Also disclosed are methods for prognosing the severity of GVHD in a subject receiving HSCT, as well as methods for monitoring efficacy of a therapeutic for treatment of GVHD. These methods generally involve assaying a biological sample from the patient for detection of T-helper 17 ($T_H17$) cells. In some embodiments, the amount of tissue-resident $T_H17$ cells is an indication of pathological grade of GVHD in the subject. In some embodiments, a reduction in the amount of tissue-resident $T_H17$ cells after treatment is an indication of therapeutic efficacy. $T_H17$ are a distinct T helper lineage mediating tissue inflammation. Retinoic acid receptor-related orphan receptor gamma (ROR gamma) regulates $T_H17$ differentiation. Therefore, in some embodiments, $T_H17$ cells are detected by assaying for RORgamma expression.

Disclosed are compositions and methods for treating and/or preventing GVHD in a subject. Also disclosed is a method for inhibiting alloreactive effector T cells in a subject receiving HSCT while permitting Treg activity. The methods can comprise administering to the subject an inhibitor of STAT3, alone or in combination with a mammalian receptor of rapamycin (mTOR) inhibitor. In some embodiments, the STAT3 inhibitor is a selective STAT3 inhibitor.

STAT3 Inhibitors

As used herein, a "selective STAT3 inhibitor" is an agent, such as a small molecule, protein, or oligonucleotide, that inhibits the activity of STAT3 in a subject without significantly inhibiting STAT5 activity. In certain embodiments, the STAT3 inhibitor is a small molecule.

"Activities" of a protein include, for example, transcription, translation, intracellular translocation, secretion, phosphorylation by kinases, cleavage by proteases, homophilic and heterophilic binding to other proteins, and ubiquitination.

STAT family members are phosphorylated by receptor-associated kinases and then form homo- or heterodimers that translocate to the cell nucleus, where they act as transcription activators. Therefore, in some embodiments, the selective STAT3 inhibitor inhibits STAT3 phosphorylation, dimerization, and/or DNA-binding.

The disclosed STAT3 inhibitor can in some cases increase the ratio of $CD4^+$ Tregs to $CD8^+$ alloreactive T effectors in the blood of the subject.

In some embodiments, the STAT3 inhibitor can increase the STAT5:STAT3 phosphorylation ratio by at least 10, 20, 30, 40, 50, 60, 70, 80, 90, or 100%. This signaling relationship can force DC-allostimulated T-cells to yield to selective STAT3 inhibition, and significantly optimizes Treg development in an otherwise proinflammatory environment.

Suitable STAT3 inhibitors are known in the art, and include, for example, quinolinecarboxamide derivatives, curcuminoid compounds, and anthraquinone derivatives. Example STAT3 inhibitors include, but are not limited to, 2-(1-hydroxyethyl)-naphtho[2,3-b]furan-4,9-dione; 2-acetyl-7-chloro-naphtho[2,3-b]furan-4,9-dione; 2-acetyl-7-fluoro-naphtho[2,3-b]furan-4,9-dione; 2-acetylnaphtho[2,3-b]furan-4,9-dione; 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester; phosphoric acid 1-(4,9-dioxo-3a,4,9,9a-tetrahydro-naphtho[2,3-b]furan-2-yl)-vinyl ester dimethyl ester; 4-[3-(2,3-dihydro-1,4-benzodioxin-6-yl)-3-oxo-1-propen-1-yl]benzoic acid; 4-{5-[(3-ethyl-4-oxo-2-thioxo-1,3-thiazolidin-5-ylidene)methyl]-2-furyl}benzoic acid; 4-[({3-[(carboxymethyl)thio]-4-hydroxy-1-naphthyl}amino)sulfonyl]benzoic acid; 3-(2-chloro-4-[(1,3-dioxo-1,3-dihydro-2H-inden-2-ylidene)methyl[-6-ethoxyphenoxy}methyl)benzoic acid; methyl 4-({[3-(2-methyoxy-2-oxoethyl)-4,8-dimethyl-2-oxo-2H-chromen-7-yl]oxy}methyl)benzoate; and 4-chloro-3-{5-[(1,3-diethyl-4,6-dioxo-2-thioxotetrahydro-5(2H)-pyrimidinylidene)methyl]-2-furyl}benzoic acid. Other STAT3 inhibitors known in the art include S3I-201; NSC 59263; NSC 42067; NSC 75912; NSC 11421; NSC 91529; NSC 263435; HL2-006-1; HL2-006-2; HL2-006-3; HL2-006-4; HL2-006-5; HL2-011-1; HL2-011-2; HL2-011-3; HL2-011-4; HL2-011-5; BG2069-1; HL2-011-6; HL2-011-7; HL2-005; HL2-003; BG2066; BG2074; BG3004; BG3006A; BG3006B; BG3006D; BG3009; RPM381; RPM384; RPM385; RPM405; RPM411; RPM407; RPM412; RPM408; RPM410; RPM415; RPM416; RPM418; RPM418-A; RPM427; RPM431; RPM432; RPM444; RPM448; RPM445; RPM447; RPM452; and RPM202 (See, for example, U.S. Patent Application Publication No. 2011/0201576 to Turkson, et al., which is hereby incorporated by reference for its teaching of STAT3 inhibitors).

Other STAT3 inhibitors are described in, for example, U.S. Patent Application Publication No. 2011/0223661 to Turkson, et al., U.S. Patent Application Publication No. 2011/0124602 to Turkson, et al., U.S. Pat. No. 7,960,434 to Turkson, et al., U.S. Patent Application Publication No. 2006/0247318 to Song, et al., U.S. Patent Application Publication No. 2011/0319362 to Wang, et al., U.S. Patent Application Publication No. 2011/0172429 to Asai, et al., U.S. Patent Application Publication No. 2005/0049299 to Aggarwal, et al., U.S. Patent Application Publication No. 2011/0212911 to Li, et al., U.S. Patent Application Publication No. 2012/0252763 to Li, et al., and U.S. Patent Application Publication No. 2011/0312984 to Tweardy, et al., each of which is hereby incorporated by reference for its teaching of STAT3 inhibitors.

Methods of screening compounds for activity against STAT3 are also known in the art. See, for example, U.S. Patent Application Publication No. 2011/0312984, which is hereby incorporated by reference for its teaching related to assaying STAT3 inhibition.

In some embodiments, the STAT3 inhibitor is a compound defined by Formula I

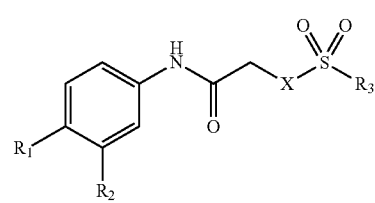

Formula I wherein

R$_1$ represents a phosphate mimic (e.g., —COOH, —SO$_3$H, —PO$_3$H, —NO$_2$, —CH$_2$COOH, —CF$_2$COOH, —CF(COOH)$_2$, or a tetrazole ring);

R$_2$ represents hydrogen, a hydroxy group, an amine, or a halogen;

X represents —O—, —NH—, —(CR$_4$ R$_4$)—NH—, —NR$_4$—, —(CR$_4$ R$_4$)—NR$_4$—, —CH$_2$—, —CH$_2$—CH$_2$—, —CHR$_4$—, —CHR$_4$—CH$_2$—, —C(R$_4$R$_4$)—; or —C(R$_4$ R$_4$)—CH$_2$—;

R$_3$ represents an alkyl group, a cycloalkyl group, an alkenyl group, an alkynyl group, an aryl group, a heteroaryl group, or an alkylaryl group; and R$_4$ represents, independently for each occurrence, hydrogen, a hydroxy group, an alkyl group, a cycloalkyl group, an alkenyl group, an alkynyl group, an aryl group, a heteroaryl group, or an alkylaryl group;

or a pharmaceutically acceptable salt or prodrug thereof.

In certain embodiments, the STAT3 inhibitor comprises S3I-201 (CAS 501919-59-1), the structure of which is shown below.

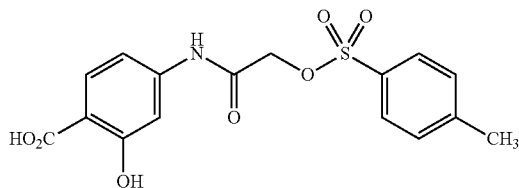 [SMILES: Cc1ccc(S(=O)(=O)OCC(=O)Nc2ccc(C(=O)O)c(O)c2)cc1]

In certain embodiments, the STAT3 inhibitor comprises a derivative of S3I-201. "Derivative", as used herein, refers to a compound that possesses the same core or skeleton as a parent compound, but differs from the parent compound in bond order, in the absence or presence of one or more atoms and/or groups of atoms, and combinations thereof. The derivative can differ from the parent compound, for example, in one or more substituents present on the core or skeleton, which may include one or more atoms, functional groups, or substructures. The derivative can also differ from the parent compound in the bond order between atoms within the core or skeleton.

In general, a derivative can be imagined to be formed, at least theoretically, from the parent compound via chemical and/or physical processes, for example, by adding and/or removing substituents, or oxidation or reduction of the parent structure. Derivatives of Stat3 inhibitors, including the STAT3 inhibitors described herein, can be prepared using a variety of reactions known in the art. Examples of suitable reactions include, but are not limited to, hydrogenation, alkylation, acetylation, and acidification reactions. Chemical modifications can be accomplished by those skilled in the art by protecting all functional groups present in the molecule and deprotecting them after carrying out the desired reactions using standard procedures known in the scientific literature. See, for example, Greene, T. W. and Wuts, P. G. M. "Protective Groups in Organic Synthesis" John Wiley & Sons, Inc. New York. 3rd Ed. pg. 819, 1999; Honda, T. et al. Bioorg. Med. Chem. Lett., 1997, 7:1623-1628; Honda, T. et al. Bioorg. Med. Chem. Lett., 1998, 8:2711-2714; Konoike, T. et al. J. Org. Chem., 1997, 62:960-966; Honda, T. et al. J. Med. Chem., 2000, 43:4233-4246; each of which are hereby incorporated herein by reference in their entirety. Derivatives exhibiting the desired biological activity (e.g., STAT 3 inhibition) can be identified or confirmed using, for example, cellular assays or other in vitro or in vivo assays.

In some embodiments, the STAT3 inhibitor comprises Stattic (CAS 19983-44-9), the structure of which is shown below.

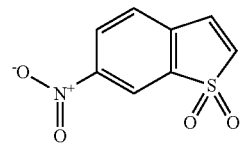

The STAT3 inhibitor may have one or more chiral centers, and thus exist as one or more stereoisomers. Such stereoisomers can exist as a single enantiomer, a mixture of enantiomers, a mixture of diastereomers, or a racemic mixture.

As used herein, the term "stereoisomers" refers to compounds made up of the same atoms having the same bond order but having different three-dimensional arrangements of atoms that are not interchangeable. The three-dimensional structures are called configurations. As used herein, the term "enantiomers" refers to two stereoisomers that are non-superimposable mirror images of one another. As used herein, the term "optical isomer" is equivalent to the term "enantiomer". As used herein the term "diastereomer" refers to two stereoisomers which are not mirror images but also not superimposable. The terms "racemate", "racemic mixture" or "racemic modification" refer to a mixture of equal parts of enantiomers. The term "chiral center" refers to a carbon atom to which four different groups are attached. Choice of the appropriate chiral column, eluent, and conditions necessary to effect separation of the pair of enantiomers is well known to one of ordinary skill in the art using standard techniques (see e.g. Jacques, J. et al., "Enantiomers, Racemates, and Resolutions", John Wiley and Sons, Inc. 1981).

The STAT3 inhibitor can also be a pharmaceutically acceptable salt of any of the compounds described above. In some cases, it may be desirable to prepare the salt of a compound described above due to one or more of the salt's advantageous physical properties, such as enhanced stability or a desirable solubility or dissolution profile.

Generally, pharmaceutically acceptable salts can be prepared by reaction of the free acid or base forms of a compound described above with a stoichiometric amount of the appropriate base or acid in water, in an organic solvent, or in a mixture of the two. Generally, non-aqueous media including ether, ethyl acetate, ethanol, isopropanol, or acetonitrile are preferred. Lists of suitable salts are found in Remington's Pharmaceutical Sciences, 20th ed., Lippincott Williams & Wilkins, Baltimore, Md., 2000, p. 704; and "Handbook of Pharmaceutical Salts: Properties, Selection, and Use," P. Heinrich Stahl and Camille G. Wermuth, Eds., Wiley-VCH, Weinheim, 2002.

Suitable pharmaceutically acceptable acid addition salts include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids.

Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

In some cases, the pharmaceutically acceptable salt may include alkali metal salts, including sodium or potassium salts; alkaline earth metal salts, e.g., calcium or magnesium salts; and salts formed with suitable organic ligands, e.g., quaternary ammonium salts. Base salts can also be formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may also be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others.

The STAT3 inhibitor can also be a pharmaceutically acceptable prodrug of any of the compounds described above. Prodrugs are compounds that, when metabolized in vivo, undergo conversion to compounds having the desired pharmacological activity. Prodrugs can be prepared by replacing appropriate functionalities present in the compounds described above with "pro-moieties" as described, for example, in H. Bundgaar, Design of Prodrugs (1985). Examples of prodrugs include ester, ether or amide derivatives of the compounds described above, polyethylene glycol derivatives of the compounds described above, N-acyl amine derivatives, dihydropyridine pyridine derivatives, amino-containing derivatives conjugated to polypeptides, 2-hydroxybenzamide derivatives, carbamate derivatives, N-oxides derivatives that are biologically reduced to the active amines, and N-mannich base derivatives. For further discussion of prodrugs, see, for example, Rautio, J. et al. *Nature Reviews Drug Discovery.* 7:255-270 (2008).

In some embodiments, the STAT3 inhibitor comprises an IL-6 inhibitor. For example, the IL-6 inhibitor can be a neutralizing antibody, such as Siltuximab (anti-IL 6 Monoclonal Antibody) or Tocilizumab (Actemra; humanised IL-6 receptor-inhibiting monoclonal antibody).

In some embodiments, the STAT3 inhibitor comprises a selective JAK2 inhibitor, such as TG101348 (CAS 936091-26-8)

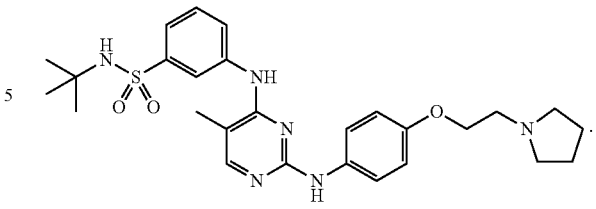

mTOR Inhibitors

In some embodiments, the method further involves administering to the subject a therapeutically effective amount of an mTOR inhibitor, such as mTOR inhibitor rapamycin (sirolimus) or a rapamycin derivative (rapalogs). Examples of rapamycin derivatives include esters, ethers, carbamates, oximes, hydrazones, and hydroxylamines of rapamycin, as well as compounds in which one or more of the functional groups attached to the attached to the rapamycin nucleus have been modified, for example, through reduction or oxidation. In certain embodiments, the mTOR inhibitor is rapamycin, temsirolimus, everolimus, ridaforolimus, pimecrolimus, merilimus, zotarolimus, TOP216, TAFA93, or nab-rapamycin.

In some embodiments, the method further involves administering to the subject a therapeutically effective amount of an immunosuppressive drug, such as tacrolimus. The method can also involve administering to the subject a therapeutically effective amount of IL-2.

Pharmaceutical Formulations

Also provided are pharmaceutical formulations which comprise a therapeutically effective amount of a STAT3 inhibitor and/or an mTOR inhibitor, or a pharmaceutically acceptable salt or prodrug thereof, in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS), and may be administered to an individual without causing undesirable biological side effects or unwanted interactions. In some cases, the pharmaceutical formulation can further contain one or more additional active agents.

Enteral Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations may be prepared using one or more pharmaceutically acceptable excipients, including diluents, preservatives, binders, lubricants, disintegrators, swelling agents, fillers, stabilizers, and combinations thereof.

Excipients, including plasticizers, pigments, colorants, stabilizing agents, and glidants, may also be used to form coated compositions for enteral administration. Delayed release dosage formulations may be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers are used to inhibit or retard drug decomposition reactions that include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Controlled Release Formulations Oral dosage forms, such as capsules, tablets, solutions, and suspensions, can for formulated for controlled release. For example, the one or more compounds and optional one or more additional active agents can be formulated into nanoparticles, microparticles, and combinations thereof, and encapsulated in a soft or hard gelatin or non-gelatin capsule or dispersed in a dispersing medium to form an oral suspension or syrup. The particles can be formed of the drug and a controlled release polymer or matrix. Alternatively, the drug particles can be coated with one or more controlled release coatings prior to incorporation in to the finished dosage form.

In another embodiment, the one or more compounds and optional one or more additional active agents are dispersed in a matrix material, which gels or emulsifies upon contact with an aqueous medium, such as physiological fluids. In the case of gels, the matrix swells entrapping the active agents, which are released slowly over time by diffusion and/or degradation of the matrix material. Such matrices can be formulated as tablets or as fill materials for hard and soft capsules.

In still another embodiment, the one or more compounds, and optional one or more additional active agents are formulated into a sold oral dosage form, such as a tablet or capsule, and the solid dosage form is coated with one or more controlled release coatings, such as a delayed release coatings or extended release coatings. The coating or coatings may also contain the compounds and/or additional active agents.

Extended Release Formulations

Extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit® In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit®. RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Eudragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS may be mixed together in any desired ratio in order to ultimately obtain a sustained-release formulation having a desirable dissolution profile. Desirable sustained-release multiparticulate systems may be obtained, for instance, from 100% Eudragit®RL, 50% Eudragit® RL and 50% Eudragit® RS, and 10% Eudragit® RL and 90% Eudragit® RS. One skilled in the art will recognize that other acrylic polymers may also be used, such as, for example, Eudragit®L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed Release Formulations

Delayed release formulations can be created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion.

Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Pulsatile Release

The formulation can provide pulsatile delivery of the one or more of the compounds disclosed herein. By "pulsatile" is meant that a plurality of drug doses are released at spaced apart intervals of time. Generally, upon ingestion of the dosage form, release of the initial dose is substantially immediate, i.e., the first drug release "pulse" occurs within about one hour of ingestion. This initial pulse is followed by a first time interval (lag time) during which very little or no drug is released from the dosage form, after which a second dose is then released. Similarly, a second nearly drug release-free interval between the second and third drug release pulses may be designed. The duration of the nearly drug release-free time interval will vary depending upon the dosage form design e.g., a twice daily dosing profile, a three times daily dosing profile, etc. For dosage forms providing a twice daily dosage profile, the nearly drug release-free interval has a duration of approximately 3 hours to 14 hours between the first and second dose. For dosage forms providing a three times daily profile, the nearly drug release-free interval has a duration of approximately 2 hours to 8 hours between each of the three doses.

In one embodiment, the pulsatile release profile is achieved with dosage forms that are closed and preferably sealed capsules housing at least two drug-containing "dosage units" wherein each dosage unit within the capsule provides a different drug release profile. Control of the delayed release dosage unit(s) is accomplished by a controlled release polymer coating on the dosage unit, or by incorporation of the active agent in a controlled release polymer matrix. Each dosage unit may comprise a compressed or molded tablet, wherein each tablet within the capsule provides a different drug release profile. For dosage forms mimicking a twice a day dosing profile, a first tablet releases drug substantially immediately following ingestion of the dosage form, while a second tablet releases drug approximately 3 hours to less than 14 hours following ingestion of the dosage form. For dosage forms mimicking a three times daily dosing profile, a first tablet releases drug substantially immediately following ingestion of the dosage form, a second tablet releases drug approximately 3 hours to less than 10 hours following ingestion of the dosage form, and the third tablet releases drug at least 5 hours to approximately 18 hours following ingestion of the dosage form. It is possible that the dosage form includes more than three tablets. While the dosage form will not generally include more than a third tablet, dosage forms housing more than three tablets can be utilized.

Alternatively, each dosage unit in the capsule may comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles may be formulated to provide immediate release, beads and granules are generally employed to provide delayed release.

Parenteral Formulations

STAT3 inhibitors and/or an mTOR inhibitors can be formulated for parenteral administration. "Parenteral administration", as used herein, means administration by any method other than through the digestive tract or non-invasive topical or regional routes. For example, parenteral administration may include administration to a patient intravenously, intradermally, intraperitoneally, intrapleurally, intratracheally, intramuscularly, subcutaneously, by injection, and by infusion.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

The parenteral formulations described herein can be formulated for controlled release including immediate release, delayed release, extended release, pulsatile release, and combinations thereof. For example, the compounds, and optionally one or more additional active agents, can be incorporated into microparticles, nanoparticles, or combinations thereof that provide controlled release. In embodiments wherein the formulations contains two or more drugs, the drugs can be formulated for the same type of controlled release (e.g., delayed, extended, immediate, or pulsatile) or the drugs can be independently formulated for different types of release (e.g., immediate and delayed, immediate and extended, delayed and extended, delayed and pulsatile, etc.).

STAT3 inhibitors and/or an mTOR inhibitors can be formulated for depot injection. In a depot injection, the active agent is formulated with one or more pharmaceutically acceptable carriers that provide for the gradual release of active agent over a period of hours or days after injection. The depot formulation can be administered by any suitable means; however, the depot formulation is typically administered via subcutaneous or intramuscular injection.

Implantation of a slow-release or sustained-release system, such that a constant level of dosage is maintained is also contemplated herein. In such cases, the active agent(s) provided herein can be dispersed in a solid matrix optionally coated with an outer rate-controlling membrane. The compound diffuses from the solid matrix (and optionally through the outer membrane) sustained, rate-controlled release. The solid matrix and membrane may be formed from any suitable material known in the art including, but not limited to, polymers, bioerodible polymers, and hydrogels.

Topical Formulations

STAT3 inhibitors and/or an mTOR inhibitors can also be formulated for topical, transdermal, or mucosal delivery. Dosage forms for topical or transdermal administration include, but are not limited to, ointments, pastes, creams, lotions, gels, powders, solutions, sprays, inhalants, or patches. The compounds are typically admixed under sterile conditions with a pharmaceutically acceptable carrier and any excipients (e.g., preservatives, buffers, etc.) that may be required. The ointments, pastes, creams and gels may contain, in addition to the active agent, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Transdermal patches have the added advantage of providing controlled delivery of a compound to the body. Such dosage forms can be made by dissolving or dispensing the compounds described herein in a proper medium. Absorption enhancers can also be used to increase the flux of the compound across the skin. The rate can be controlled by either providing a rate controlling membrane or by dispersing the compound(s) in a polymer matrix or gel.

Powders and sprays (e.g., for pulmonary delivery) can contain, in addition to the active agent, excipients such as lactose, talc, silicic acid, aluminum hydroxide, calcium silicates and polyamide powder, or mixtures of these drugs. Sprays can additionally contain customary propellants such as chlorofluorohydrocarbons.

Compositions for rectal or vaginal administration are preferably suppositories which can be prepared by mixing the compounds described herein with suitable non-irritating excipients or carriers such as cocoa butter, polyethylene glycol, or a suppository wax which are solid at ambient temperature but liquid at body temperature and therefore melt in the rectum or vaginal cavity and release the compound(s).

Administration

The disclosed STAT3 inhibitor and/or an mTOR inhibitor can be administered before, during, or after hematopoietic stem cell transplantation (HSCT) to inhibit the risk of graft-versus-host disease. For example, the STAT3 inhibitor and/or an mTOR inhibitor can be administered within 2 weeks, 1 week, 6 days, 5 days, 4 days, 3 days, 2 days, or 1 day before HSCT. The STAT3 inhibitor and/or an mTOR inhibitor can be administered on the same day as HSCT, including simultaneously. The STAT3 inhibitor and/or an mTOR inhibitor may be administered up to 1, 2, 3, 4, 5, 6 days, 1 week, 2 weeks, 1 month, 6 months, or 1 year after HSCT. In some embodiments, the STAT3 inhibitor and/or an mTOR inhibitor is administered as a controlled release formulation in order to provide sustained levels of STAT3 inhibitor and/or an mTOR inhibitor.

HSCT is the transplantation of multipotent hematopoietic stem cells, usually derived from bone marrow, peripheral blood, or umbilical cord blood. In the case of a bone marrow transplant, the HSC can be removed from a large bone of the donor, typically the pelvis, through a large needle that reaches the center of the bone. Peripheral blood stem cells can be collected from the blood through a process known as apheresis. The peripheral stem cell yield can be boosted with daily subcutaneous injections of granulocyte-colony stimulating factor, serving to mobilize stem cells from the donor's bone marrow into the peripheral circulation. It is also possible to extract hematopoietic stem cells from amniotic fluid for both autologous or heterologous use at the time of childbirth. Umbilical cord blood is obtained when a mother donates her infant's umbilical cord and placenta after birth.

Unlike other organs, bone marrow cells can be frozen (cryopreserved) for prolonged periods without damaging too many cells. To cryopreserve HSC, a preservative, DMSO, can be added, and the cells cooled very slowly in a controlled-rate freezer to prevent osmotic cellular injury during ice crystal formation. HSC may be stored for years in a cryofreezer, which typically uses liquid nitrogen.

Chemotherapy or irradiation is generally given to the subject immediately prior to a transplant to help eradicate the patient's disease prior to the infusion of HSC and to suppress immune reactions. The bone marrow can be ablated (destroyed) with dose-levels that cause minimal injury to other tissues. In allogeneic transplants a combination of cyclophosphamide with total body irradiation is conventionally employed. This treatment also has an immunosuppressive effect that prevents rejection of the HSC by the recipient's immune system. However, in some embodiments, immunosuppressive drugs are either not used, or are used at reduced dosages, in the disclosed methods.

Reduced-intensity (non-myeloablative allogeneic) transplants use lower doses of chemotherapy and radiation, which are too low to eradicate all the bone marrow cells of a recipient. After several weeks of growth in the bone marrow, expansion of HSC and their progeny is sufficient to normalize the blood cell counts and reinitiate the immune system.

The disclosed compositions, including pharmaceutical formulations, may be administered in a number of ways. For example, the disclosed formulations can be administered intravenously, intraperitoneally, intramuscularly, subcutaneously, intracavity, or transdermally. The formulations may be administered orally, parenterally, by intramuscular injection, by intraperitoneal injection, transdermally, extracorporeally, ophthalmic ally, vaginally, rectally, intranasally, topically or the like, including topical intranasal administration or administration by inhalant.

DEFINITIONS

The term "individual," "host," "subject," and "patient" are used interchangeably to refer to any individual who is the target of administration or treatment. The subject can be a vertebrate, for example, a mammal Thus, the subject can be a human or veterinary patient.

The term "therapeutically effective" refers to the amount of a composition or formulation used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "small molecule" refers to a molecule, such as an organic or organometallic compound, with a molecular weight of less than 1,500 Daltons (e.g., less than 1250 Da, less than 1000 Da, or less than 800 Da). The small molecule can be a hydrophilic, hydrophobic, or amphiphilic compound.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. In certain embodiments, alkyl refers to a lower alkyl group (e.g., $C_1$-$C_6$ for a straight chain, $C_3$-$C_6$ for a branched chain). Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The alkyl groups may also be substituted with one or more groups including, but not limited to, halogen, hydroxy, amino, thio, ether, ester, carboxy, oxo, and aldehyde groups. The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methyl-enedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

As generally used herein "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio. Pharmaceutically acceptable carriers and/or excipients include those include compounds or materials generally recognized as safe (GRAS) by the U.S. Food and Drug Administration.

A number of embodiments of the invention have been described. Nevertheless, it will be understood that various modifications may be made without departing from the spirit and scope of the invention. Accordingly, other embodiments are within the scope of the following claims.

EXAMPLES

Example 1

STAT5 Polarization Promotes iTregs and Suppresses Human T-Cell Alloresponses while Preserving CTL Capacity Materials and Methods
Cells, Media, and Reagents Donor leukocyte concentrates were obtained from healthy volunteers in accordance with the Declaration of Helsinki (Florida Blood Services, St. Petersburg, Fla., USA). PBMCs were isolated over lymphocyte separation medium (Corning Cellgro, Manassas, Va., USA). T cells were isolated in an inactivated state through nylon-wool column elution (Fisher Scientific, Pittsburgh, Pa., USA), with a purity of greater than 95%. moDCs were cytokine generated and matured as published [Betts, B. C., et al. (2011) Blood 118, 5330-5339]. Small-molecule inhibitors included S3I-201 (STAT3) and CAS 285986-31-4 (STAT5) (EMD Millipore, Billerica, Mass., USA), diluted in DMSO (<0.1% v/v).

mAbs and Flow Cytometry

Fluorochrome-conjugated mouse anti-human mAbs included anti-CD3, -CD4, -CD8, -CD25, -CD45RO, -CD107a, -CD127, -Foxp3, -pSTAT3/pY705, -pSTAT5/pY694, -IFN-, and -IL-17A (BD Biosciences, San Jose, Calif. USA; eBioscience; San Diego, Calif., USA; Invitrogen; Carlsbad, Calif., USA). Viability was assessed by Live/Dead staining (Invitrogen). Live events were acquired on FACSCalibur or LSRII (BD Biosciences) flow cytometers (FlowJo software, ver. 7.6.4; TreeStar, Ashland, Oreg., USA). Gates were defined by appropriate isotype controls. Naive T-cell sorting was performed on the FACSVantage-DiVa (BD Biosciences). Where indicated, CD4$^+$ T cells were purified by magnetic-bead negative selection (Miltenyi Biotec, Auburn, Calif., USA).

Allo-MLRs

Allo-MLRs consisted of T cells stimulated by cytokine-mature moDCs (DC:T-cell ratio 1:30, $1\times10^5$ T cells per 100 µl medium in a 96-well plate, 37° C.). S3I-201 (50 or 100 µM) or DMSO control was added once on day 0. The allogeneic moDC stimulators were matured with a cytokine cocktail and terminally differentiated, eliminating the need for irradiation [Betts, B. C., et al. (2011) Blood 118, 5330-5339]. T-cell proliferation was quantified by a colorimetric assay (CellTiter 96 AQueous One Solution Cell Proliferation Assay [MTS]; Promega, Madison, Wis.) on day 5, per the manufacturer's instructions, with absorbance quantified at 490 nm [Betts, B. C., et al. (2011) Blood 118, 5330-5339]. The stimulation index was calculated by dividing the OD of the allo-MLR by the OD of T cells alone. PHA-stimulated T cells served as a positive control. Identical allo-MLRs were cultured with CAS 285986-31-4, to determine the dose-response effect of STAT5 inhibition on allostimulated T-cell growth. For these initial experiments, the cultures were analyzed on day 4 because of the early rapid T-cell proliferation among the STAT5 inhibitor-treated wells. The stimulation index was determined as described. CAS 285986-31-4 (1 µM) was identified as the optimal concentration, based on maximum T-cell proliferation, and 5-day cocultures were used in subsequent experiments.

Evaluation of STAT3 and -5 Phosphorylation

To confirm selective STAT3 inhibition, T cells were first briefly allostimulated by moDCs (DC:T cell ratio 1:30) and then pulsed with the relevant STAT3- or -5-dependent cytokine in the presence or absence of S3I-201. The 3-day exposure to allogenic moDCs allows the responding T cells to increase CD25 expression and capacity to receive IL-2 signaling, while resting or stimulated T cells phosphorylate STAT3 in response to IL-6 [Betts, B. C., et al. (2011) Blood 118, 5330-5339]. DC-allostimulated T cells ($1\times10^6$) were then exposed to S3I-201 (50 or 100 µM) or DMSO for 4 h in serum-free RPMI (Corning Cellgro) to reduce background phosphorylation, followed by a 15 min pulse with IL-6 (4000 IU/ml) or -2 (50 IU/ml). T-cell STAT phosphorylation was determined by surface staining for CD3, followed by fixation (CytoFix; BD Biosciences), permeabilization with cold methanol, and intracellular staining for STAT3 and -5. The phosphorylated STAT3 and -5 geometric MFI ratio was calculated by dividing the geometric MFI of the cytokine-pulsed cells by the geometric MFI of the corresponding fluorochrome isotype. The percentage of STAT3 and bright STAT5 phosphorylation in the T cells is depicted by the gates in each respective histogram (FIG. 1C, D).

To evaluate the effect of selective STAT3 or -5 blockade on STAT polarization after DC allosensitization alone, S3I-201 (50 or 100 µM), CAS 285986-31-4 (STAT5 inhibitor, 1 µM), or DMSO was added to the allo-MLRs once on day 0. No exogenous cytokine was added. DC-allosensitized T cells were harvested on day 5. STAT3 and -5 phosphorylation and geometric MFI ratios were determined by flow cytometry, as described earlier. The ratio of CD4$^+$, pSTAT5$^{Bright}$ to CD4$^+$, pSTAT3$^+$ T cells was calculated by percentage of phosphorylation.

iTreg and Tconv Expansion and Staining

To evaluate iTreg development, naive CD4$^+$ cells were isolated from nylon-wool-eluted T cells by magnetic-bead selection (Miltenyi Biotec), based on the positive expression of CD4 and lack of CD45RO, CD25, or both. In addition, CD127 staining of the naive CD4$^+$ cells was performed after the purification, to ensure depletion of natural Tregs from the cell product. Negligible amounts of CD127$^-$, CD25$^{Bright}$ nTregs were observed after magnetic-bead purification. The naive CD4$^+$ T cells were DC allostimulated (DC:T cell ratio 1:30, $1\times10^5$ T cells per 200 µl medium in a 96-well plate, 37° C.) with S3I-201 (25-100 µM), CAS 285986-31-4 (1 µM), or DMSO added once on day 0. The T cells were harvested and surface stained on day 5 for CD3, -4, -25, and -127, followed by fixation and permeabilization (eBioscience), and then intracellular staining for Foxp3 [Liu, W., et al. (2006) J. Exp. Med. 203, 1701-1711; Seddiki, N., et al. (2006) J. Exp. Med. 203, 1693-1700]. Tregs were characterized by gating on the live cells expressing surface $CD3^+$, $CD4^+$, and absence of $CD127$, followed by expression of Foxp3 and $CD25^{bright}$ [Liu, W., et al. (2006) J. Exp. Med. 203, 1701-1711; Seddiki, N., et al. (2006) J. Exp. Med. 203, 1693-1700]. The absolute number of iTregs and Tconv ($CD4^+$ $CD25^-$) cells was obtained by timed acquisition. The ratio of iTreg:Tconv was calculated based on the absolute number of each T-cell population.

iTreg suppression assay. The suppressive potency of the STAT3 inhibitor-treated iTregs were compared with nTreg function in an allo-MLR. iTregs were generated by coculturing purified naive $CD4^+$ $CD25^-$ T cells with allogeneic moDCs, as described in the presence of S3I-201 (50 μM). On day 5, iTregs were selected by expression of CD3 and CD4; lack of CD127; and bright expression of CD25 by flow sorting. The purified iTregs were titrated against allo-MLRs consisting of $5 \times 10^4$ responder $CD4^+$ $CD25^-$ T cells from the iTreg donor and $1.6 \times 10^3$ HLA-disparate mature moDCs from the original stimulator donor. iTreg-to-responder $CD4^+$ $CD25^-$ T-cell ratios included 0:1, 1:27, 1:9, 1:3, 1:1, and 1:0, with iTregs alone and Tconvs alone as the controls. Sorted, untreated nTregs from the iTreg donors were titrated against allo-MLRs, by using identical methods. T-cell proliferation was determined by pulsing cells with 1 μCi/well 3H-thymidine for the last 18 h in culture and harvested on day 6. The limited number of iTregs from cocultures treated with S3I-201 (100 μM) or CAS 285986-31-4 (1 μM) prevented their inclusion in these suppression experiments.

iTreg Foxp3 demethylation assay. The degree of Foxp3 demethylation among purified iTregs was measured to evaluate the stability of the iTreg populations in response to STAT3 (S3I-201 at 50 or 100 μM) or -5 (CAS 285986-31-4 at 1 μM) inhibition [Toker, A., et al. (2013) J. Immunol. 190, 3180-3188; Miyao, T., et al. (2012) Immunity 36, 262-275]. The degree of Foxp3 TSDR demethylation among iTregs from DMSO-treated allo-MLRs, purified nTregs, and Tconvs served as the controls [Veerapathran, A., et al. (2013) Blood 122(13):2251-61]. For these experiments, iTregs and nTregs were sorted to select the $CD4^+$ $CD25^+$ $CD127^-$ population. PCR products were amplified by using methylation or demethylation specific TSDR forward and reverse primers from bisulphate-treated genomic DNA of sorted natural Tregs. DNA fragments were cloned into a pCR2.1-Topo vector (Life Technologies, Grand Island, N.Y., USA) and verified by DNA sequencing. The following TSDR primers and probes were used for PCR: methylation forward 5'-GTTTTCGATT TGTTTAGATT TTTTCGTT-3' (SEQ ID NO:1), reverse 5'-CCTCTTCTCT TCCTCCGTAA TATCG-3' (SEQ ID NO:2), and hydrolysis probe 5'-TAMRA-ATGGCGGTCG GATGCGTCGG GT-FAM-3' (SEQ ID NO:3); and demethylation forward 5'-GTTTTTGATT TGTTTAGATT TTTTTGTT-3' (SEQ ID NO:4), reverse 5'-CCTCTTCTCT TCCTCCATAA TATCA-3' (SEQ ID NO:5), and hydrolysis probe 5'-TAMRA-ATGGTGGTTG GATGTGT TGGGT-FAM-3' (SEQ ID NO:6). Standards were diluted at concentrations ranging from $2^7$ to $2^3$ plasmid copies of each methylation or demethylation TSDR. Genomic DNA was isolated by using the DNeasy Blood and Tissue kit (Qiagen, Valencia, Calif., USA) from sorted natural or expanded iTregs.

Genomic DNA (200-500 ng) was treated with bisulfite from the EZ DNA Methylation-Gold Kit (Zymo Research, Irvine, Calif., USA). After bisulfite conversion, qPCR was performed with TaqMan Universal PCR Master Mix No AmpErase UNG (Life Technologies) containing methylation or demethylation TSDR forward or reverse primers, methylation- or demethylation TSDR specific hydrolysis probe, and bisulfite-treated genomic DNA. PCR was performed with a 95° C. preheating step for 10 min, and then 50 cycles at 95° C. for 15 s, followed by 1 min at 61° C.

Evaluation of $T_H17$ Responses

To optimize the detection of IL-17A producing cells, nylon-wool-purified T cells underwent $CD4^+$ magnetic-bead selection. The $CD4^+$ T cells were cultured in triplicate with allogeneic, mature moDCs (DC:T cell ratio 1:30, $1 \times 10^6$ T cells/1 ml medium in a 48-well plate, 37° C.) and treated with S3I-201 (50 or 100 μM) or DMSO. The medium was supplemented with IL-6 ($10^5$ IU/ml), TGF-β (4 ng/ml), and anti-IFN-γ mAb (10 μg/ml) to support $T_H17$ growth. The T cells were harvested and stimulated with PMA/ionomycin for 5 h, with GolgiStop Protein Transport Inhibitor (BD Biosciences) added after 1 h of activation. $T_H17$ cells were identified by surface CD3 and CD4 expression, followed by intracellular staining for IL-17A. The absolute number of IL-17A-producing $CD4^+$ T cells was obtained by timed acquisition.

The concentration of IL-17A was measured (anti-human IL-17A [homodimer] ELISA Ready-Set-Go; eBioscience) in the supernatant of identically prepared and drug-treated CD4 T-cell allo-MLRs (DC:T cell ratio 1:30, $1.5 \times 10^5$ T cells per 125 μl medium in a 96-well plate, 37° C.). After 5 days, PMA/ionomycin was added directly to the cultures and stimulated for 5 h. GolgiStop was omitted from the PMA/ionomycin activation step, to permit detection of IL-17A in the culture supernatants. The supernatants were collected, and the IL-17A protein concentration was measured in triplicate, per the manufacturer's instructions.

Evaluation of CD8 CTL Capacity

The naive $CD8^+$ T cells were purified by live cell sorting ($CD4^-$ and $CD45RO/CD25^-$) and were stimulated with allogeneic moDCs (DC:T cell ratio of 1:30), with S3I-201 (50 or 100 μM) or DMSO added once on day 0. On day 5, the allosensitized CD8 T cells were harvested and stimulated with PMA/ionomycin in the presence of Golgi Stop and anti-CD107a, followed by surface CD8 and intracellular IFN-γ staining.

Statistical Analysis

Statistical comparisons were determined with the paired, 2-tailed Student's t test (Prism software, ver. 5.04; GraphPad, San Diego, Calif., USA). Statistical significance was defined by $P<0.05$.

Results

Specific STAT3 Inhibition Impaired DC-Allosensitized T-Cell Proliferation

A dose titration of S3I-201-treated allo-MLRs showed a 50% reduction in T-cell proliferation at 50 μM and complete impairment at 100 μM, with little effect at 1 or 10 μM of the STAT3 inhibitor (FIG. 1A). Additional experiments confirmed that S3I-201 significantly reduced T-cell proliferation in allo-MLRs, compared with DMSO (FIG. 1B). T-cell viability was preserved at 50 μM of S3I-201, although viability staining showed toxicity at 100 μM, with the greatest effect observed among the Tconvs, rather than the iTregs.

S3I-201 Suppressed STAT3 Phosphorylation while Permitting IL-2/STAT5 Signaling

To evaluate the selectivity of STAT inhibition by S3I-201, T cells were briefly pulsed with IL-6 or -2, to measure the degree of permitted STAT3 or -5 phosphorylation, respectively. S3I-201 inhibited IL-6-mediated STAT3 signaling at 50 and 100 μM in alloactivated T cells (FIG. 1C, E, F). Conversely, IL-2-induced STAT5 phosphorylation occurred in all treated T cells, as demonstrated by significant increases in STAT5 geometric MFI and bright STAT5 signaling compared with unstimulated baseline levels (FIG. 1D, G, H). The highest degree of STAT3 inhibition selectivity was achieved with 50 μM S3I-201. Off-target effects of S3I-201 were seen at 100 μM, given the decrease in IL-2/STAT5 phosphorylation by geometric MFI ratio ($P>0.5$) and percentage of phosphorylation ($P<0.5$), compared with the DMSO control (FIG. 1G, H).

STAT3 Blockade Polarized T Cells Toward STAT5 Phosphorylation

Figure 2A:
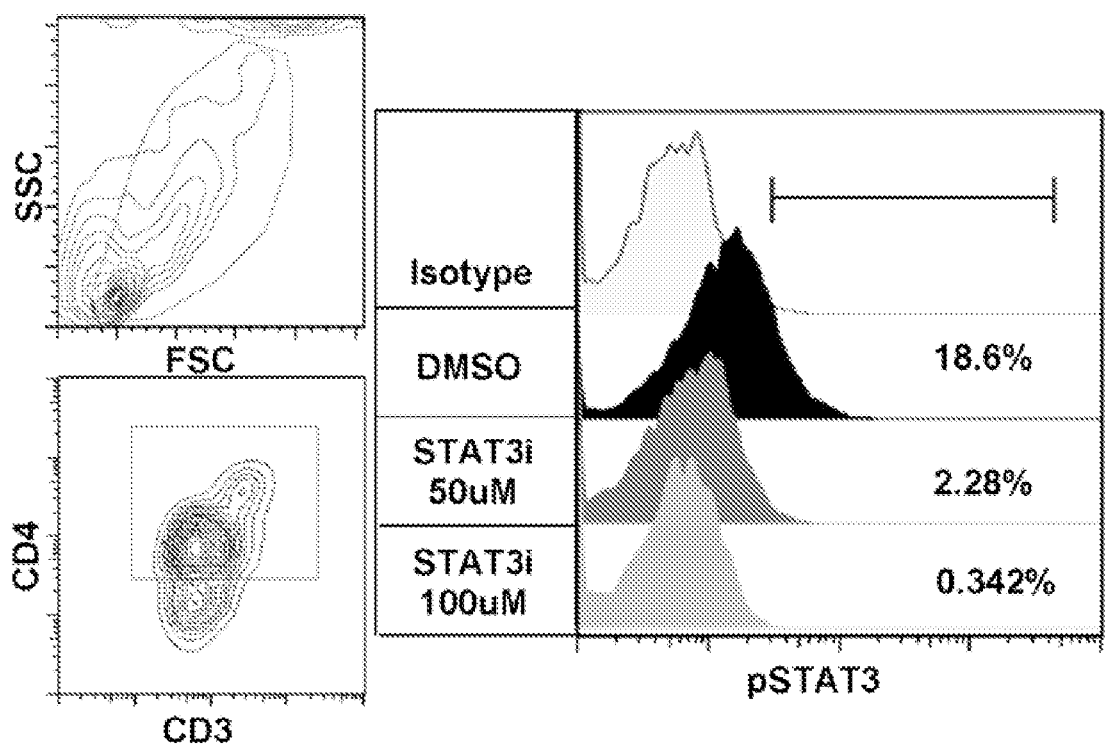
FIG. 2. STAT3 inhibition with S3I-201 polarized STAT5 phosphorylation in allostimulated CD4+ T cells. (A, B) Representative contour plots show gating strategy and histograms demonstrate reduced STAT3 phosphorylation in CD4+ alloresponders, with preservation of STAT5 activity, in 5 day allogeneic cocultures (DC:T cell ratio 1:30) treated with S3I-201 vs. DMSO without the addition of any exogenous cytokine. (A, B) Gates define the CD4+, pSTAT3+ and CD4+, pSTAT5$^{Bright}$ T cells, respectively. (C, D) The mean±SD of results in 3 independent experiments of STAT3 and -5 phosphorylation by geometric MFI ratio. (E) the frequency of CD4+, pSTAT5$^{Bright}$ T cells, and (F) the CD4+, pSTAT5$^{Bright}$: pSTAT3+ ratio by percentage of phosphorylation, in CD4+ T cells harvested from S3I-201- or DMSO-treated 5 day allogeneic cocultures. *P<0.05, P=0.001-0.01, *P=0.0001-0.001, NS, by paired t test.
Figure 2B:
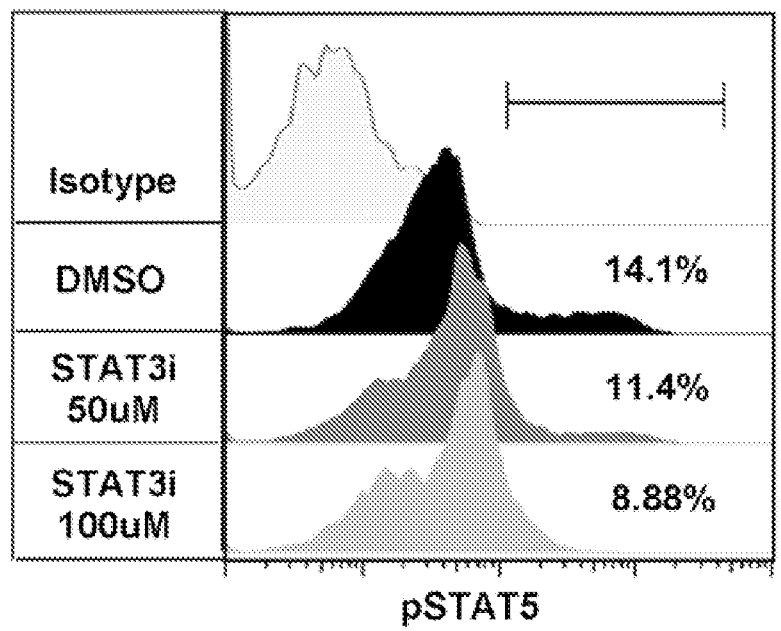

S3I-201 maintained on-target suppression of STAT3 in 5 day allo-MLRs, where no exogenous cytokines were added (FIG. 2A, C). STAT5 activation was preserved in response to DC allostimuli, without a statistically significant decline in measurable phospho-protein (FIG. 2B, D). Specific attention was focused on the CD4$^+$, pSTATSBright population, given that Tregs are known to express higher levels of STAT5 phosphorylation than Tconvs [Zeiser, R., et al. (2008) Blood 111, 453-462; Matsuoka, K., et al. (2013) Sci. Transl. Med. 5, 179ra43]. This population was maintained among the S3I-201- and DMSO-exposed alloresponders, although a trend in reduced STAT5 phosphorylation was observed at 100 μM of the STAT3 inhibitor (FIG. 2E). However, the S3I-201-treated conditions showed reduced STAT3 signaling in all cases and resulted in a robust, dose-dependent polarization of the ratio of CD4$^+$, pSTAT5$^{Bright}$ to CD4$^+$, pSTAT3$^+$ T cells (FIG. 2F).

Figure 3B:
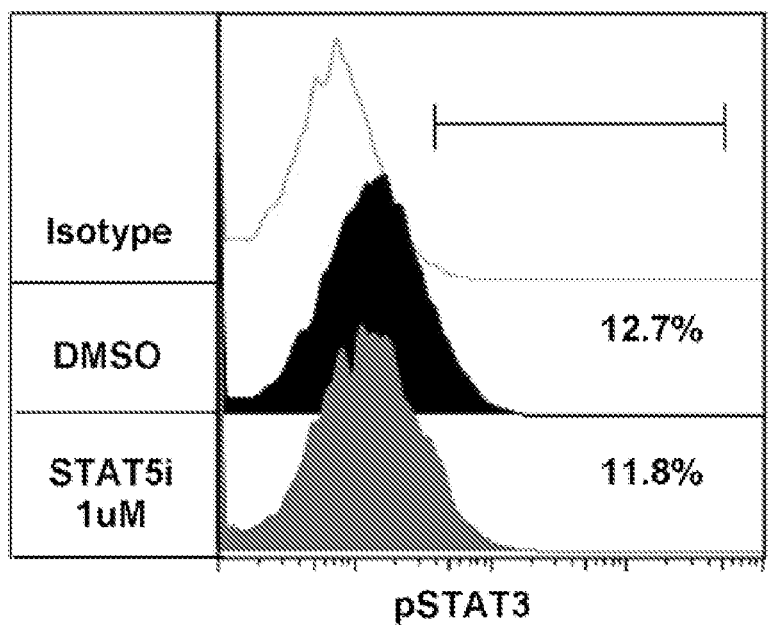
FIG. 3. Inhibition of bright STAT5 phosphorylation among CD4+ alloresponders. (A) Dose response of CAS 285986-31-4 (STAT5 inhibitor, 0-100 μM) in human allo-MLRs (DC:T cell ratio 1:30) treated once on day 0 with drug or DMSO diluent control. T-cell proliferation was determined by a colorimetric assay on day 4. The stimulation index was calculated by dividing the OD of the allo-MLR by the OD of T cells alone. (B, C) Representative histograms (using an identical gating strategy as in FIG. 2A) demonstrate the on-target selectivity of CAS 285986-31-4, impairing bright STAT5 activity, yet preserving STAT3 phosphorylation in 5 day allostimulated T cells. (B, C) Gates in the histograms define the (B) CD4+, pSTAT3+ and (C) CD4+, pSTAT5$^{Bright}$ T cells. Graph data are the mean±SD of results in 3 independent experiments. (D) STAT3 and (E) −5 phosphorylation by geometric MFI ratio, (F) the frequency of CD4+, pSTAT5$^{Bright}$ T cells, and (G) the CD4+, pSTAT5$^{Bright}$:pSTAT3 ratio by percentage of phosphorylation in CD4+ T cells harvested from CAS 285986-31-4- or DMSO-treated 5 day allogeneic cocultures. *P<0.05, paired t test.
Figure 3C:
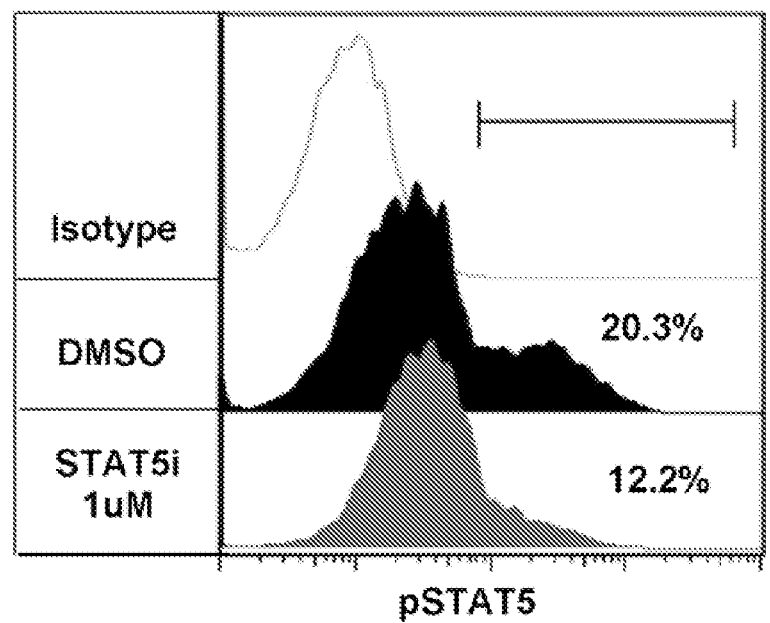
Figure 3D:
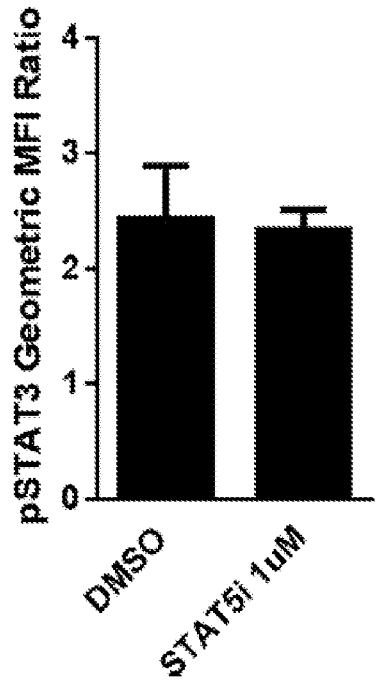
Figure 3E:
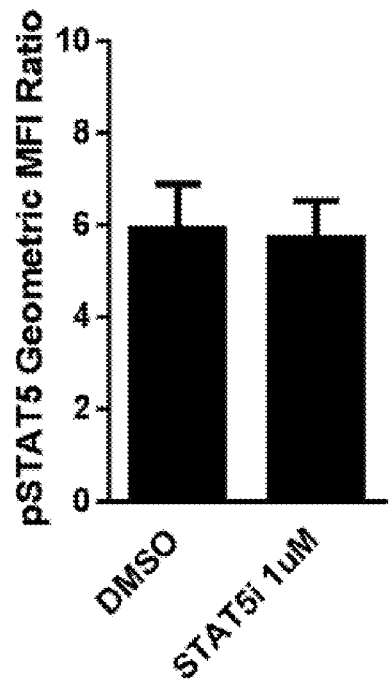
Figure 3F:
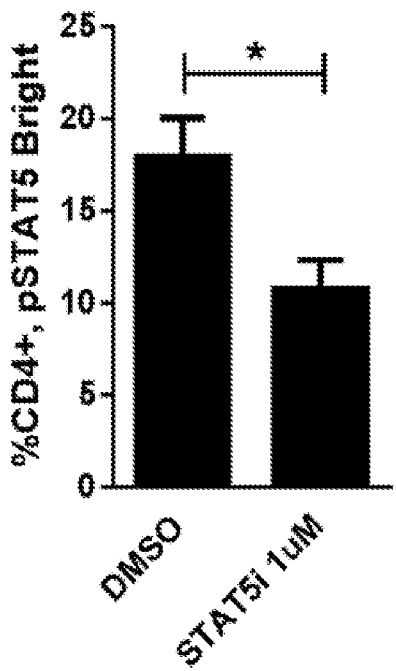
Figure 3G:
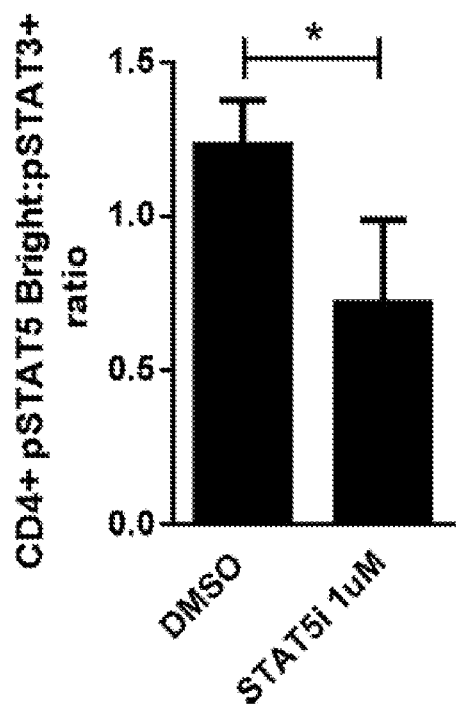

CAS 285986-31-4 (a STAT5 inhibitor, 1 μM) was used to further evaluate the influence of STAT5 phosphorylation on alloreactivity. Partial blockade of STAT5 was chosen to shift STAT phosphorylation and avoid the broad effects of complete IL-2 deprivation among the alloresponders [Lin, J. X., et al. (2012) Immunity 36, 586-599]. The dose of CAS 285986-31-4 was titrated by T-cell proliferation in treated allo-MLRs. A concentration of 1 μM achieved maximum allostimulated T-cell growth, with no toxic effects by viability staining (FIG. 3A). While 1 μM of CAS 285986-31-4 did not affect the overall geometric MFI of CD4$^+$ STAT5 phosphorylation (FIG. 3C, E), this dose selectively impaired the CD4$^+$, pSTAT5$^{Bright}$ population (FIG. 3C, F) and maintained intact STAT3 signaling (FIG. 3B, D). This significantly decreased the ratio of CD4$^+$, pSTAT5$^{Bright}$ to CD4$^+$, pSTAT3$^+$ T cells (FIG. 3G).

STAT3 Blockade Significantly Expanded Allostimulated iTregs

Figure 4A:
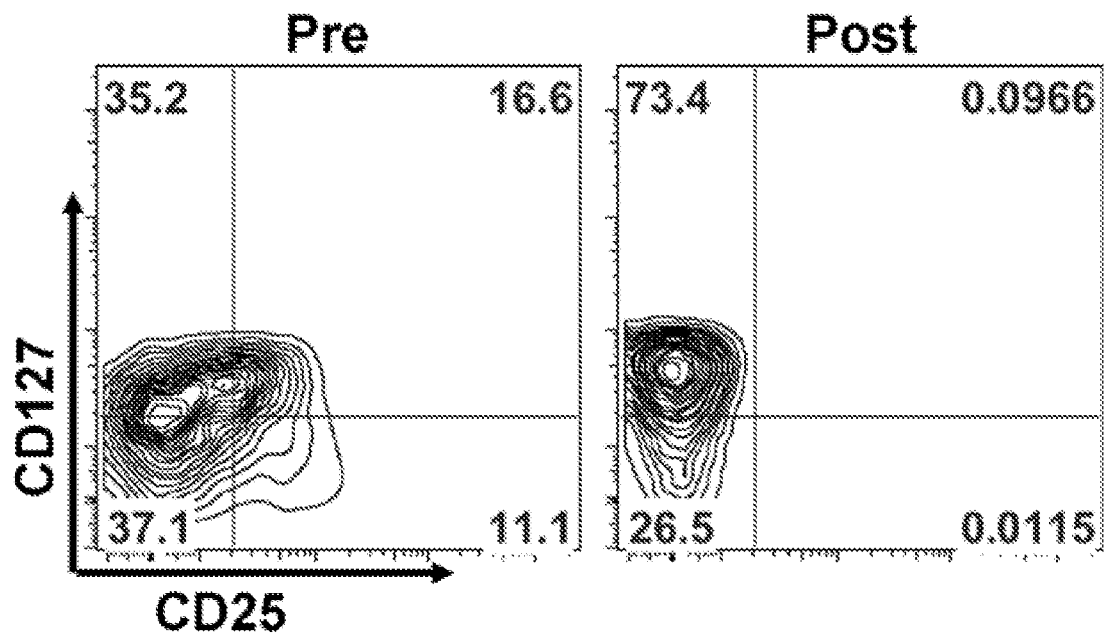
FIG. 4. STAT3 inhibition expanded potent allostimulated iTregs. (A) Naive CD4+, CD45RO−/CD25− T cells were purified through magnetic bead selection and depleted of nTregs before allogeneic coculture. nTregs are shown as CD127−, CD25$^{Bright}$ gating on the CD4+ T cells before and after depletion. (B) Representative histogram demonstrates the degree of Foxp3 expression among CD4+, CD127−, CD25$^{Bright}$ T cells after allostimulation of naive CD4+ T cells with mature moDCs (DC:T cell ratio 1:30 for 5 days) treated with either S3I-201 (STAT3 inhibitor), CAS 285986-31-4 (STAT5 inhibitor), or DMSO-diluent control. (C) Expansion of iTregs vs. Tconvs in absolute number (triplicate mean±SD) from 5 day allogeneic cocultures treated with S3I-201, CAS 285986-31-4, or DMSO. (D) The effects of STAT3 vs. −5 inhibition on the ratio (triplicate means±SD) of iTregs to Tconvs, calculated according to absolute number of T cells. Results are from 1 representative experiment of 5. (E) The suppressive capacity of sorted iTregs expanded from STAT3-treated allogeneic cocultures vs. purified untreated nTregs was tested at different ratios to self CD4+ CD25− responders stimulated by original allogeneic moDCs (DC:T cell ratio 1:30). Graphs show the percentage of proliferation based on 3H-thymidine incorporation and triplicate means±SD of counts per minute at day 6. (F) Triplicate means±SD of percentage of demethylated Foxp3 among purified iTregs expanded in allogeneic cocultures treated with S3I-201, CAS 285986-31-4, or DMSO. Results shown are from 1 representative experiment of 2. *P<0.05, paired t test.
Figure 4B:
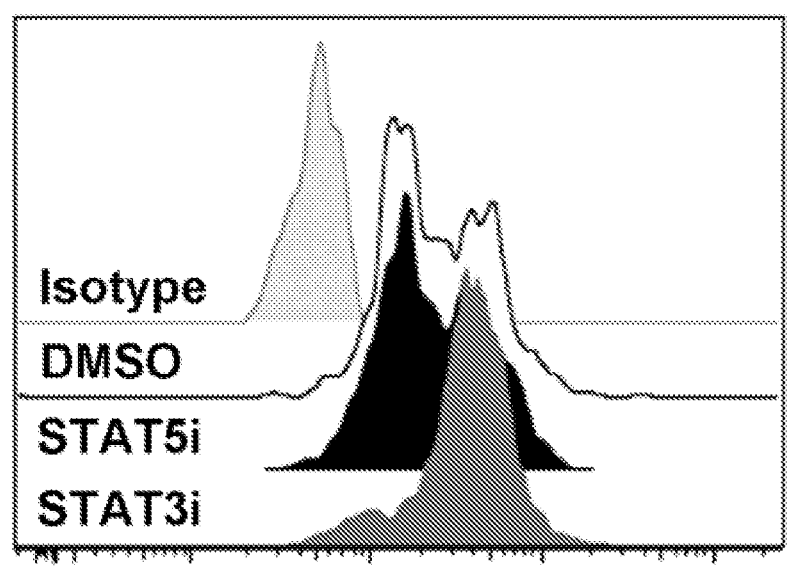
Figure 4C:
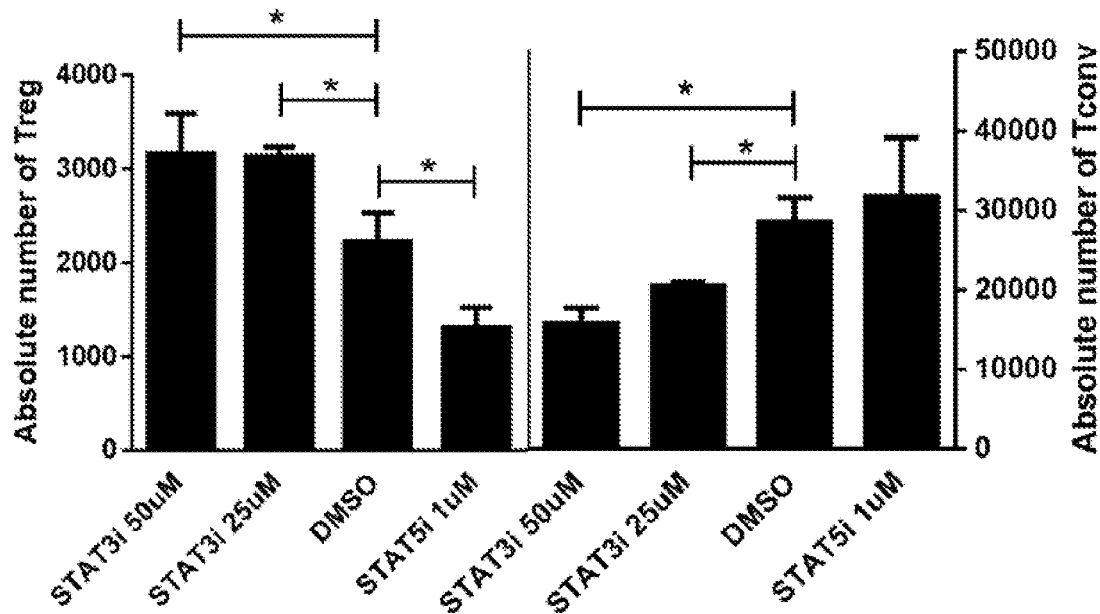
Figure 4D:
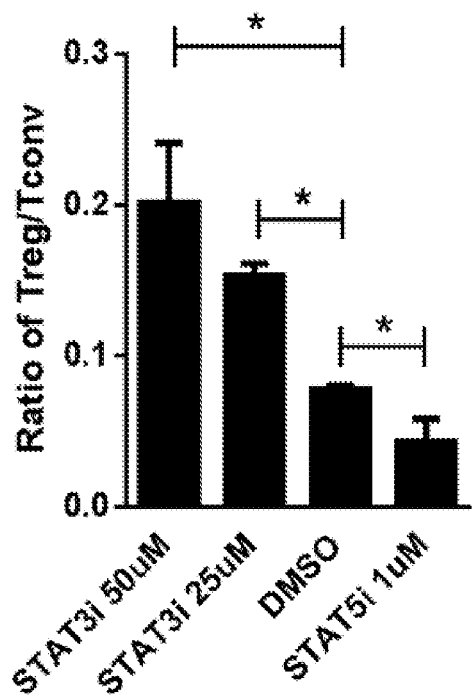

Based on the observation that STAT3 inhibition polarized STAT5 signaling in CD4 alloresponders, the effects of S3I-201 on Foxp3 expression and iTreg expansion was investigated. Use of purified, naive CD4$^+$ T cells devoid of contaminating nTregs showed that STAT3 inhibition significantly increased the absolute number of iTregs in a dose-dependent manner at 25 μM and 50 μM of S3I-201 (FIG. 4A-C). Moreover, the number of competing alloreactive Tconvs was dramatically reduced, resulting in an increased ratio of iTregs to Tconvs (FIG. 4D). While 100 μM of S3I-201 significantly reduced the number of iTregs compared with DMSO, the effect on the Tconvs was greater, suggesting a lower susceptibility threshold of STAT3 deprivation among the Tconvs. Conversely, STAT5 inhibition with CAS 285986-31-4 significantly decreased allostimulated iTreg expansion, paired with a significant reduction in the iTreg:Tconv ratio compared with DMSO or the STAT3 inhibitor-treated conditions (FIG. 4D).

Figure 4E:
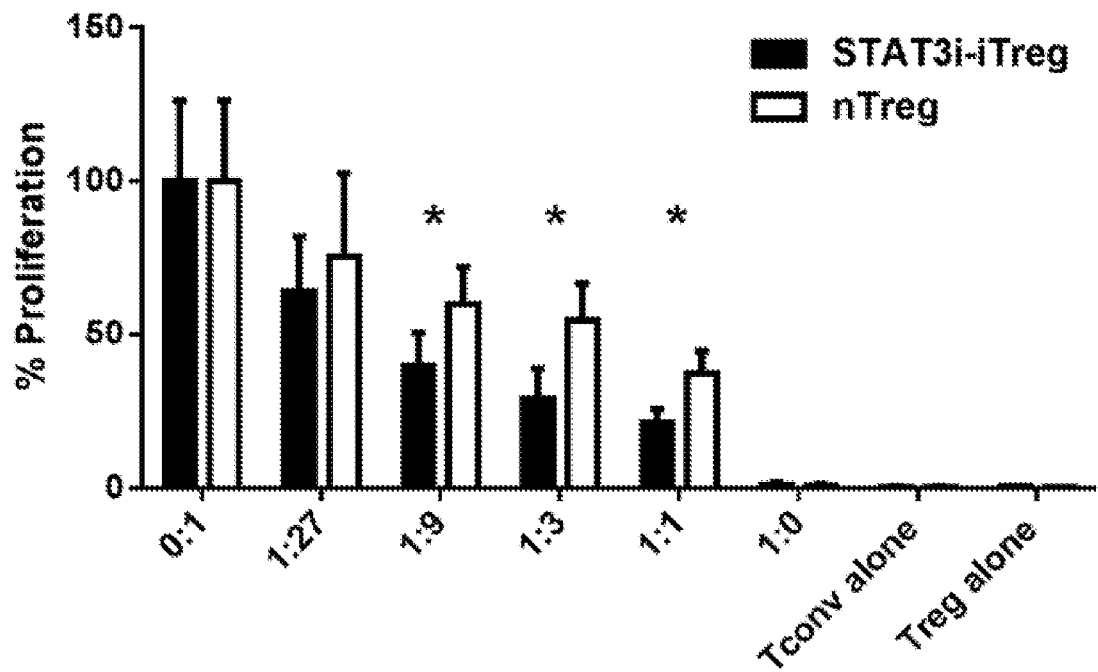

STAT3-Deprived iTregs Displayed a Potent Suppressive Function iTregs expanded from STAT3 inhibitor-treated cocultures were titrated against Tconvs from the same donor in allo-MLRs (DC:T cell ratio 1:30) to evaluate iTreg suppression of DC-allostimulated T cells. Similarly, untreated nTregs from the same iTreg donors where titrated in parallel allo-MLRs. In all cases, no inhibitors or exogenous cytokines were added to the suppression assay allo-MLRs. After 6 days of culture, T-cell proliferation was measured. The STAT3-deprived iTregs demonstrated significant suppressive potency, compared with the nTregs at Treg:Tconv ratios of 1:9, 1:3, and 1:1 (FIG. 4E).

Figure 4F:
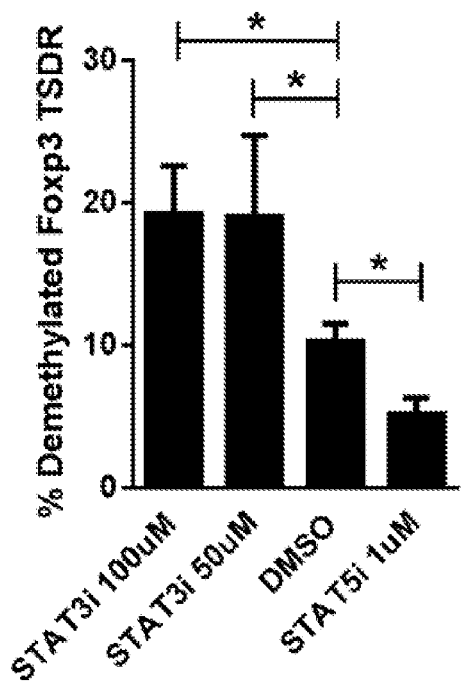

STAT3 Inhibition Facilitated Foxp3 Demethylation Among Expanded iTregs iTreg phenotype stability and suppressive function is linked to the degree of Foxp3 demethylation. iTreg reverting to a Tconv-like state may still express Foxp3; however, in such cases, Foxp3 becomes highly methylated [Toker, A., et al. (2013) J. Immunol. 190, 3180-3188; Miyao, T., et al. (2012) Immunity 36, 262-275]. The degree of Foxp3 demethylation was quantified among the iTregs expanded from S3I-201-, CAS 285986-31-4-, and DMSO-treated cocultures. STAT3 inhibition with 50 or 100 μM of S3I-201 significantly enhanced the amount of iTreg Foxp3 demethylation, compared with DMSOtreated iTregs (FIG. 4F). Moreover, STAT5 inhibition with 1 μM of CAS 285986-31-4 rendered a significant reduction in Foxp3 demethylation (FIG. 4F).

STAT3 Inhibition Suppressed T$_H$17

Figure 5A:
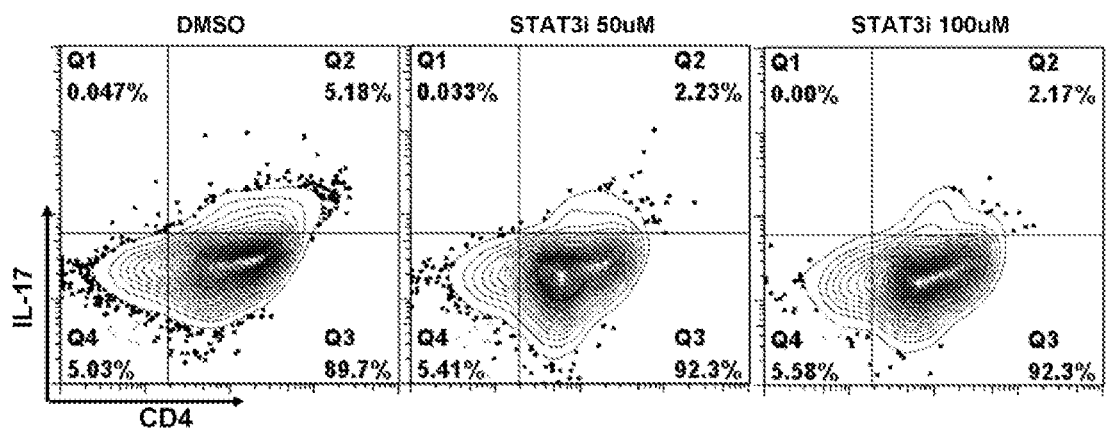
FIG. 5. STAT3 inhibition suppressed Th17 responses. (A) Contour plots show a reduction in the CD4+, IL-17A+ population among allostimulated T cells (DC:CD4+ T cell ratio 1:30) in 5 day cocultures treated with S3I-201, compared with DMSO. (B, C) Effects of STAT3 inhibition on the percentage and absolute number of allostimulated CD4+, IL-17A+ T cells as triplicate means±SD from 3 independent experiments. (D) Reduction in IL-17A protein concentration (triplicate means±SD from 3 independent experiments) from the supernatants of 5 day allogeneic cocultures treated with S3I-201 or DMSO control. *P<0.05, paired t test.
Figure 5B:
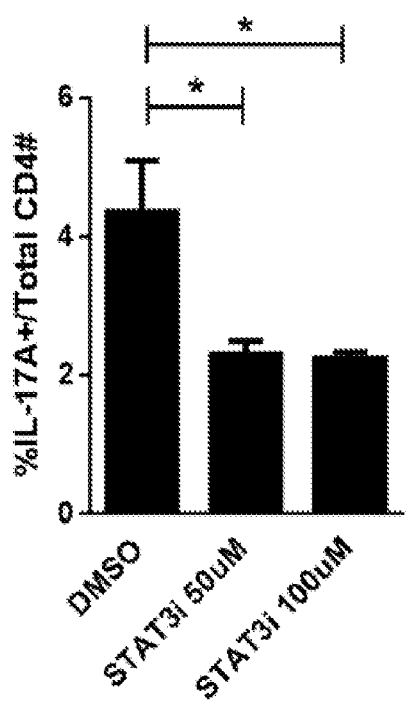
Figure 5C:
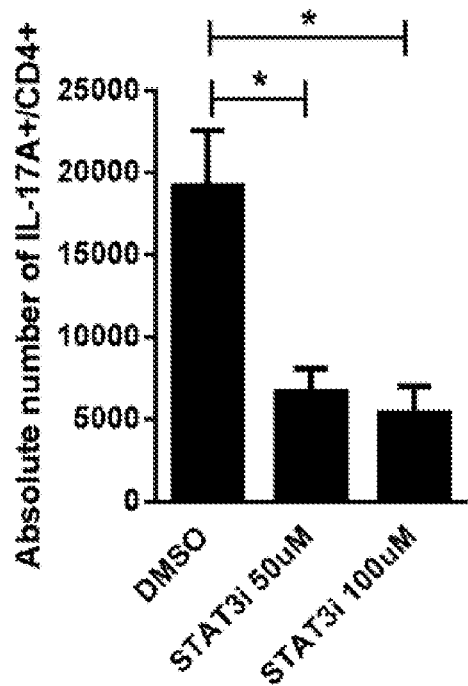
Figure 5D:
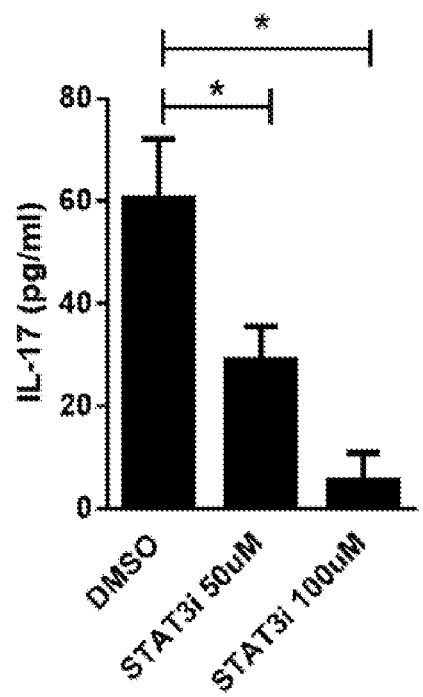

STAT3 blockade impaired T$_H$17 responses, as demonstrated by a significant reduction in both the frequency and absolute numbers of CD4$^+$, IL-17A$^+$ T cells, compared with DMSO (FIG. 5A-C). Given that T$_H$17 cells represent a small fraction of alloresponders, these findings were further strengthened by a significant decrease in IL-17A protein concentration within the supernatants of cocultures treated with S3I-201 (FIG. 5D). In these experiments, 1×10$^6$ CD4$^+$ T cells (as opposed to 1×10$^5$) were cultured with moDCs at a DC:T-cell ratio of 1:30, to optimize the final T$_H$17 yield.

STAT3 Inhibition Preserved CTL Capacity

Figure 6A:
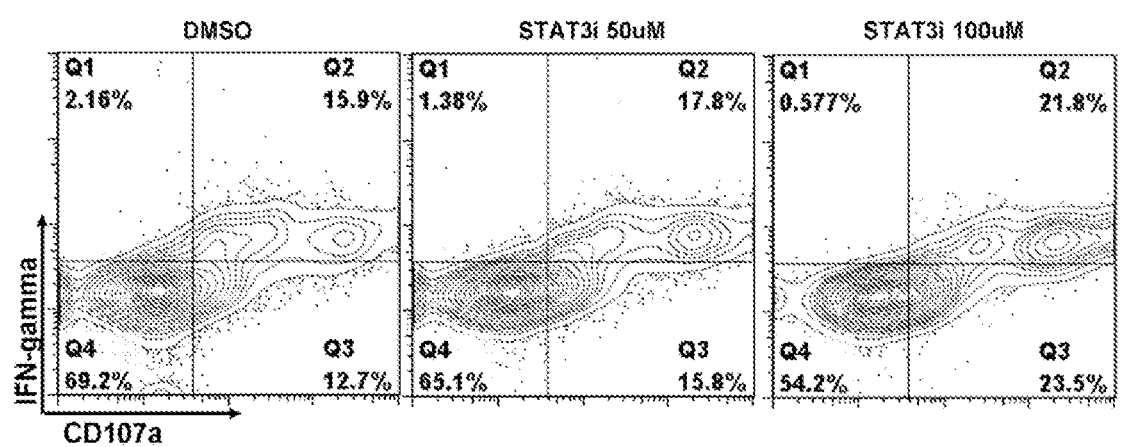
FIG. 6. STAT3 inhibition preserved CTL capacity. (A) Contour plots and (B) bar graph shows preserved CD8 CTL capacity by CD107a and IFN-γ expression, in S3I-201- or DMSO-treated allo-MLRs. Allogeneic cocultures (DC: CD8+ T cell ratio 1:30) were analyzed on day 5. Graph data are the mean±SD from 3 independent experiments. NS, paired t test.
Figure 6B:
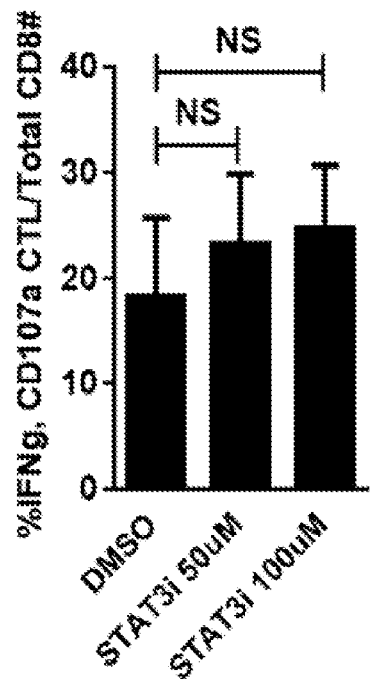

Maintenance of CTL function is critical for the beneficial anti-malignancy immune properties of the allograft [Warren, E. H., et al. (1998) Blood 91, 2197-2207; Faber, L. M., et al. (1992) J. Exp. Med. 176, 1283-1289]. Allostimulated CD8+ effectors from cocultures treated with S3I-201 demonstrated intact cytolytic potential by way of CD107a expression [Rubio, V., et al. (2003) Nat. Med. 9, 1377-1382] and intracellular IFN-γ production (FIG. 6). The CTL potential among S3I-201-treated CD8$^+$ T cells was not significantly different from that of the DMSO control.

Discussion

In this study, human alloresponder T cells were susceptible to selective STAT3 inhibition. This approach impaired allostimulated T-cell proliferation, while promoting STAT5-mediated iTreg growth and function. Allostimulated iTregs were most efficiently expanded when treated with 50 μM of S3I-201, paired with a decrease in Tconvs and a positive shift in the iTreg:Tconv ratio. These iTregs not only had intact suppressive capacity, but they displayed greater potency than the nTregs. Moreover, the expressed Foxp3 among the STAT3 inhibitor-exposed iTreg demonstrated a significantly increased amount of demethylation. This finding indicates a higher degree of Foxp3 expression stability and functional capacity among these expanded iTregs. Of interest, the dose-dependent increase in the ratio of CD4$^+$, pSTAT5$^{Bright}$ to CD4$^+$, pSTAT3$^+$ T cells appeared to share a similarly positive trend with the iTreg:Tconv ratio in response to the STAT3 inhibitor.

Conversely, partial STAT5 inhibition with 1 μM of CAS 285986-31-4 dramatically impaired iTreg expansion. Moreover, STAT3 phosphorylation was enabled at this concentration and Tconv expansion was maintained. Although Foxp3-expressing iTregs were still detectable in cultures treated with CAS 285986-31-4, the degree of Foxp3 demethylation was severely decreased and was rendered susceptible to potential instability. These opposing effects induced by STAT5 inhibition strengthen the importance of balance between STAT5 and −3 phosphorylation with respect to human iTreg alloresponses.

In this setting, iTregs differentiated and expanded when challenged with DC-allostimuli, and this effect was significantly enhanced by blocking STAT3 during culture. This result identifies a potential distinction between human and murine allostimulated iTreg growth. In murine GVHD models, where MHC-disparate recipients receive donor marrow accompanied by unmodified, naive T cells, iTregs show negligible development [Laurence, A., et al. (2012) Immunity 37, 209-222]. Conversely, iTregs are detected only when the mice receive allogeneic STAT3 knockout, naive T cells [Laurence, A., et al. (2012) Immunity 37, 209-222].

Selective STAT3 inhibition by S3I-201 was confirmed, with potent suppression of IL-6/STAT3 signaling in the treated T cells. STAT5 phosphorylation occurred in response to stimulation with IL-2 as well, with the greatest degree of STAT3 inhibition selectivity achieved at 50 M of S3I-201.

Off-target reduction in IL-2-mediated STAT5 phosphorylation was observed an at 100 μM of S3I-201, the concentration at which iTreg expansion was impaired. It was noted that the responding Tconvs were more extensively affected by S3I-201 at 100 μM and correspondingly increased the ratio of iTregs to Tconvs. Although Tconvs may be more susceptible to STAT3 deprivation, this observation may be confounded by off-target effects of S3I-201 at high concentrations.

In a human system of alloreactivity, STAT3 inhibition abrogates $T_H17$ responses when added to cocultures supplemented with IL-6, TGF-β, and IFN-γ mAb. Neutralization of IL-6 with tocilizumab is an insufficient means of reducing $T_H17$ responses or enhancing opposing Treg development [Betts, B. C., et al. (2011) Blood $T_H17$, 5340-5343]. Selective JAK2 inhibition, however, successfully achieved a reduction in Th17 cells, while preserving rather than increasing Treg populations [Betts, B. C., et al. (2011) Blood 118, 5330-5339]. It is now clearly shown that downstream STAT3 inhibition is sufficient to both reduce $T_H17$ and alternatively optimize iTreg expansion. As such, this approach directly targets unwanted $T_H17$-dependent STAT3 signaling, while facilitating Treg-dependent STAT5 activity and Foxp3 demethylation.

The preservation of human $CD8^+$ CTL capacity provides mechanistic evidence that STAT3 blockade permits effector function through intact IL-2/STAT5 signaling pathways. In all CTL experiments, CD107a expression was linked to concurrent intracellular expression of IFN-γ within the $CD8^+$ alloresponders. Although STAT3 inhibition reduced overall T-cell proliferation in allo-MLRs, the cytolytic potential was unhindered by S3I-201. As such, $CD8^+$ CTL capacity remained intact despite STAT3 blockade with S3I-201, where similar amounts of CD107a and IFN-γ expression were observed compared with that found with DMSO control.

STAT3 inhibition with agents such as S3I-201 can offer enhanced fidelity in controlling alloreactivity, compared with upstream JAK2 or relevant cytokine receptor blockade [Betts, B. C., et al. (2011) Blood 118, 5330-5339; Betts, B. C., et al. (2011) Blood 118, 5340-5343], given that STAT3 phosphorylation is not exclusive to JAK2 activation alone. Moreover, the current data identified the plasticity of the STAT5:STAT3 dynamics as a critical mediator and target of human alloreactivity. The approach proposed here is highly translatable and reveals the potential implications of incorporating selective STAT3 inhibition in the prevention and management of GVHD.

Example 2

S3I-201 Treatment of GVHD In Vivo

Figure 7A:
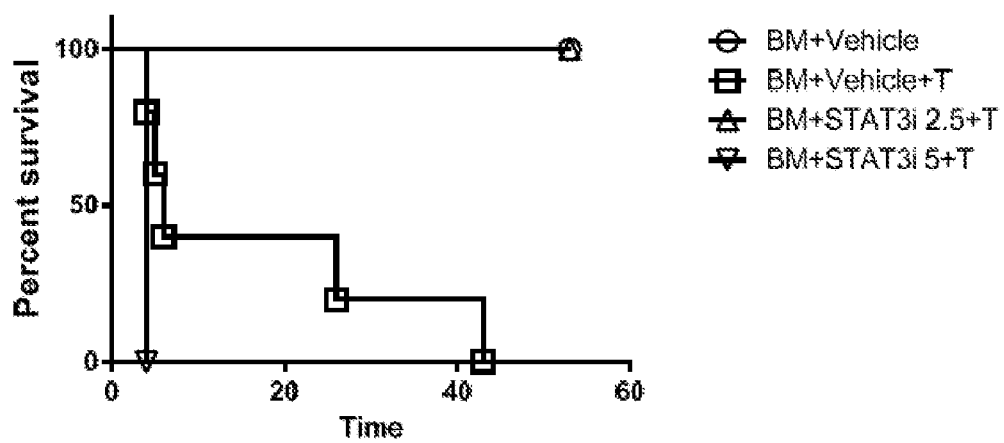
FIG. 7. B6 T-cell depleted marrow (+/− T-cells) were given to Balb/c mice. S3I-201 or vehicle was given by i.p. from day 0 to day +7 only. Mice were then followed for body weight (FIG. 7B), GVHD clinical scores (FIGS. 7C, 7D), and survival (FIG. 7A).
Figure 7B:
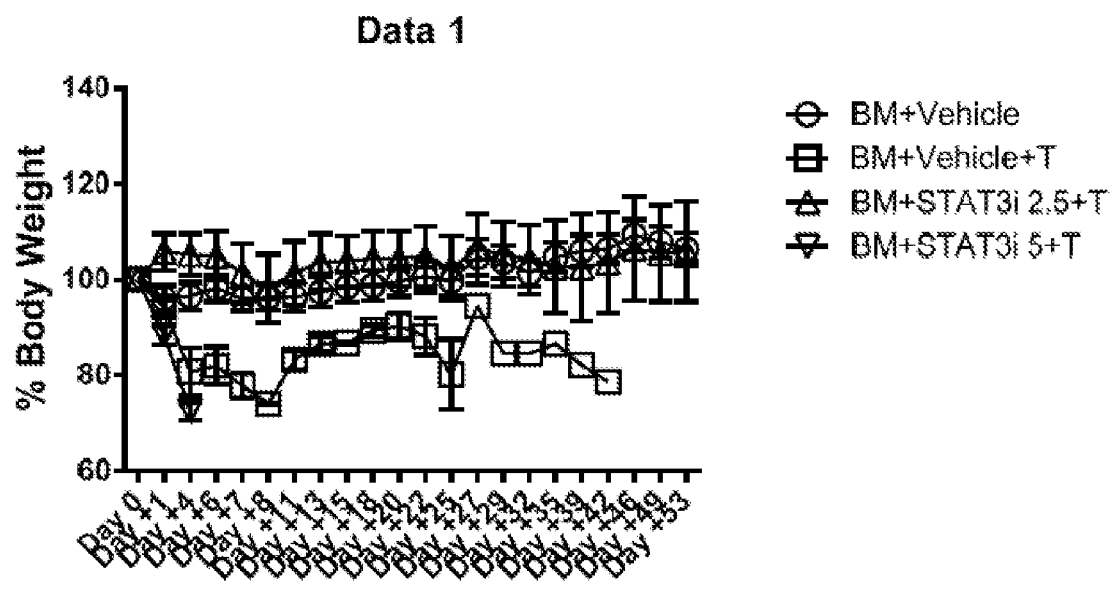
Figure 7C:
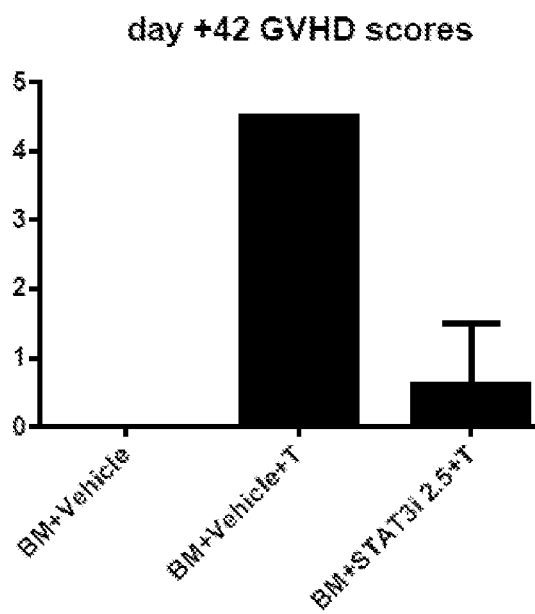
Figure 7D:
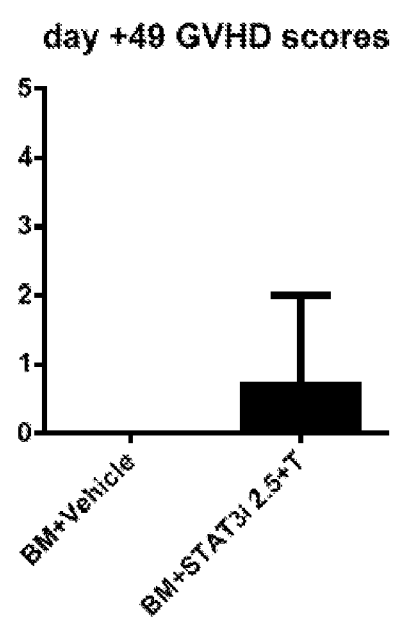

B6 T-cell depleted marrow (+/− T-cells) were given to Balb/c mice. S3I-201 or vehicle was given by i.p. from day 0 to day +7 only. Mice were then followed for body weight (FIG. 7B), GVHD clinical scores (FIGS. 7C, 7D), and survival (FIG. 7A). The 5 mg/kg of S3I-201 was toxic, but 2.5 mg/kg was well tolerated. All of the GVHD control mice (i.e., TCD marrow+T-cells+vehicle) have since died of GVHD. All of the S3I-201 and TCD marrow negative controls (no T-cells) were alive at day +53.

Example 3

STAT3 Activation and RORgammaT+ $T_H17$ Cell Tissue Invasion are Associated with Acute GVHD Onset, Severity, and Therapeutic Response Materials and Methods STAT3 Phosphorylation Among Allogeneic HCT Recipients Patients over 18 years of age (n=18) receiving an allogeneic peripheral blood or bone marrow hematopoietic cell transplantation had a single peripheral blood sample collected day +21 after HCT. Eligibility for the STAT3 activation study (MCC 16925) was not restricted by primary malignancy, transplantation indication, conditioning regimen, or GVHD prophylaxis regimen. All enrolled patients demonstrated an absolute neutrophil count >500 at time of peripheral blood collection. Patients were consented in accordance with the Declaration of Helsinki. Recipients of umbilical cord blood grafts were not eligible due to concern for associated lymphopenia at day +21. Patients demonstrating any proven or potential signs (nausea, diarrhea, rash, and/or hyperbilirubinemia) or diagnosis of acute GVHD at or before day +21 were excluded from the investigation. Additionally, patients receiving systemic glucocorticoids were deemed ineligible. STAT3 phosphorylation was measured by flow cytometry at day +21 (+/−2 days) from allograft infusion as described below. T-cell STAT3 phosphorylation was also measured in samples from healthy volunteers (n=5, OneBlood, St. Petersburg, Fla., USA). Descriptive data was collected, including transplantation date, patient age, gender, primary disease, graft source (relation, gender, and age), GVHD prophylaxis regimen, and conditioning intensity. The patients were followed prospectively for GVHD symptoms, onset, and severity until day +100. The acute GVHD grade was verified by chart review and recorded according to consensus criteria (Przepiorka et al 1995) [Przepiorka, D, et al. (1995) Bone Marrow Transplant 15:825-8]. Assignment of acute GVHD grade was based on clinical manifestations as standard, and patients were categorized as GVHD grade 0-I or grade II-IV. Due to confounding etiologies of nausea and/or anorexia during the post-transplant period, data from patients with upper gastrointestinal symptoms alone (i.e. no skin, liver, or lower gastrointestinal GVHD) were analyzed within the grade 0-I group. In a secondary analysis, we included such cases in the grade II-IV acute GVHD group.

mAbs and Flow Cytometry

Fluorochrome-conjugated mouse anti-human mAbs included anti-CD3, anti-CD4, anti-CD126, anti-phosphorylated STAT3 Y705, and anti-phosphorylated S6 ribosomal protein ser235/236 (BD Biosciences, San Jose, Calif. USA; eBioscience San Jose, Calif. USA; Cell Signaling Technology, Boston, Mass. USA). Live events were acquired on a FACSCalibur flow cytometer (FlowJo software, ver. 7.6.4; TreeStar, Ashland, Oreg., USA). The phosphorylated STAT3 and S6 gates were defined by an isotype control.

Measurement of STAT3 Phosphorylation

At 21 days following allograft infusion, a total of 30 ml of heparinized peripheral blood was collected from asymptomatic patients. Peripheral blood mononuclear cells (PBMC) were freshly isolated from patient and healthy volunteer blood (OneBlood) by gradient density over Ficoll-Paque PLUS (GE Healthcare Bio-Sciences Corp., Piscataway, N.J. USA). To amplify STAT3 phosphoprotein detection, $1-3\times10^6$ PBMCs were either pulsed or not with 4000 IU/ml of IL-6 (R&D Systems, Minneapolis, Minn. USA) for 15 minutes in 1 ml of serum-free RPMI (Corning Cellgro, Manassas, Va. USA) at 37° C. [Betts, B C, et al. (2011) Blood 118:5330-9; Betts, B C, et al. (2013) J Leukoc Biol. 2014 95(2):205-13; Betts, B C, et al. (2011) Blood 118: 5340-3]. The PBMCs were then directly treated with CytoFix (BD Biosciences) pre-warmed to 37° C. for 10 minutes. Following a wash with PBS, the PBMCs were permeabilized with ice-cold methanol (90% vol/vol) for at least 20 minutes at −20° C. The cells were stained for expression of CD3, CD4, and phosphorylated STAT3 Y705. The absolute numbers of STAT3+CD4 and CD8 T-cells were calculated by multiplying the fraction of each phosphorylated T-cell subset among the patient's absolute lymphocyte count on the day of blood draw.

Measurement of IL-6 Receptor Alpha

PBMCs were isolated from donor leukocyte concentrates of healthy volunteers (OneBlood). T-cells were purified using nylon wool column elution then stimulated with cytokine-matured autologous or allogeneic monocyte-derived dendritic cells (moDC) (DC:T-cell ratio of 1:30) for 3 days as previously described (Florida Blood Services) [Betts, B C, et al. (2011) Blood 118:5330-9; Betts, B C, et al. (2013) J Leukoc Biol. 2014 95(2):205-13; Betts, B C, et al. (2011) Blood 118:5340-3]. Resting T-cells were included as a baseline control. CD4+ T-cell surface expression of IL-6 receptor alpha (CD126) was evaluated by flow cytometry.

GVHD Tissue Immunohistochemistry

Tissue samples were obtained upon diagnosis of GVHD from patients randomized to rapamycin (Rapa)/tacrolimus (TAC), or methotrexate (MTX)/TAC in a GVHD prevention trial (NCT00803010) [Pidala, J, et al. (2012) Haematologica 97:1882-9]. Cases with acute GVHD who had a diagnostic biopsy performed were identified for this analysis. Biopsy was not mandated on protocol for GVHD diagnosis, and thus included GVHD biopsy samples reflect usual clinical practice Immunohistochemistry (IHC) was performed to evaluate the phenotype of tissue-resident CD4+ T-cells. Clinical acute GVHD severity was scored per standard criteria [Przepiorka, D, et al. (1995) Bone Marrow Transplant 15:825-8].

Pathologic GVHD grading was performed according to standard criteria by a Pathologist blinded to the administered GVHD prophylaxis regimen. Biopsies were preserved in neutral buffered formalin and processed in usual manner. On the H&E stained tissue sections, the portion of interest on each biopsy was outlined by the pathologist for incorporation into a tissue microarray (TMA). Cylindrical punches were removed from paraffin-embedded tissue blocks to create a TMA. Tissue microarray was utilized to improve experimental uniformity and ensure highly parallel analysis.

Slides were stained using a Ventana Discovery XT automated system (Ventana Medical Systems, Tucson, Ariz.) per manufacturer's recommendations with proprietary reagents. Antibodies to RORgamma (rabbit, 1:300 Abcam, Cambridge, Mass.), T-bet (mouse, 1:25, BD Biosciences, San Jose, Calif.), FoxP3 (mouse, 1:25, Abcam, Cambridge, Mass.) and CD4 (rabbit, 1:25, Cell Marque, Rocklin, Calif.) were utilized for IHC. Briefly, 4 µm sections were transferred to positively charged slides. The slides were deparaffinized on the automated system with EZ Prep solution (Ventana Medical Systems). Heat-induced antigen retrieval was performed in Cell Conditioning 1 (Ventana) for FoxP3 and T-bet, and in RiboCC (Ventana) for CD4 and RORgamma. The samples were then incubated with the selected antibodies using Dako antibody diluent (Carpenteria, Calif.), followed by Ventana UltraMap anti-mouse or -rabbit secondary antibody. Ventana ChromoMap kit detection system was used and the slides were counterstained with hematoxylin. The slides were then dehydrated and coverslipped per normal laboratory protocol.

For the double stains, after deparaffinization, heat induced antigen retrieval was performed with Cell Conditioning 1. The samples were incubated first with either the CD3 or IL-17 antibody and then the OmniMap anti-rabbit secondary antibody was applied. First antibody detection utilized the Ventana ChromoMap kit. Then the slides were subsequently incubated with RORgamma antibody (1:200) followed by the UltraMap anti-rabbit multimer (Ventana) and the Alk Phos chromagen (Ventana). Finally, the slides were counterstained with hematoxylin, dehydrated and coverslipped per normal laboratory protocol.

Stained slides were scanned using Aperio™ (Vista, Calif., USA) ScanScope XT with a 200×/0.75 NA objective lens at a rate of 3 minutes per slide via Basler tri-linear-array. Positivity for each marker was quantitatively scored using the TMA module of the TissueStudio v3.0 software platform from Definiens (Munich, Germany) for each TMA core (0.6 mm diameter, or 1.13 mm² area) Staining intensity thresholds were held constant throughout the study. In a subset of 10 randomly selected TMA cores, contiguous sections (4 nm thickness) were stained with CD4 and RORgamma for co-registration analysis. The negative pen tool was used on each core to manually segment the regions which would NOT be scored, including the epithelium (FIG. 15). RORgamma was used to identify $T_H17$, T-bet for Th1, and FoxP3 for Treg. A subset of cores were double stained for 1) RORgamma and CD3 (n=24) or 2) RORgamma and IL-17 (n=16) to confirm low background inclusion of type 3 innate lymphoid cells (ILC3) from our tissue analysis (CD3 negative, RORgamma or IL-17 positive) [Kim, H Y, et al. (2014) Nature medicine 20:54-61; Geiger, T L, et al. (2014) The Journal of experimental medicine 211:1723-31; Longman, R S, et al. (2014) The Journal of experimental medicine 211:1571-83; Munneke, J M, et al. (2014) Blood 124:812-211 The double stained cores were scanned using the Aperio™ (Vista, Calif.) ScanScope XT with a 200×/0.8 NA objective lens with a 2× doubler (0.265 µm/pixel) at a rate of 10 minutes per slide via Basler tri-linear-array detection. The whole slide image (.svs) was loaded in ImageScope (Aperio) and the epithelium was excluded from the scoring. The resultant image was imported into Tissue Studio v3.0 (Definiens) and segmented as described above. Within the specific region of interest indicated by the study pathologist (EMS), individual cells were identified using hematoxylin thresholding (0.2) and an IHC threshold for both red (0.85) and brown (0.35) staining. The typical nucleus size was set to be 60 μm$^2$ and the cells were grown (cell simulation at 2 nm) in every direction. A nucleus size of 60 μm$^2$ was used to exclude IL-17+ mast cells from the double stained cores [Lin, A M, et al. (2011) J Immunol 187:490-500; Keijsers, R R, et al. (2014) The Journal of investigative dermatology 134:1276-84]. Cells were binned into four categories based upon the IHC stain intensity: negative, red only positive (CD3 or IL-17, respectively) or brown only (RORgamma) positive or double stained for both red and brown stain.

Akt-mTOR-S6 Versus IL-6-STAT3 Signaling Among Random Donor T-Cells

T-cells were serum-starved in RPMI treated with DMSO diluent control, rapamycin 100 ng/ml (EMD Millipore, Billerica, Mass. USA), or STAT3 inhibitor S3I-201 50 uM (H. Lee Moffitt Cancer Center, Drug Discovery Core) for 4 hours. For the STAT3 experiments, the T-cells were first DC-allostimulated (DC:T-cell ratio of 1:30) for 3 days to optimize surface expression of IL-6 receptor alpha and STAT3 signaling among healthy volunteers. The T-cells were then cytokine-pulsed for 15 minutes with either IL-2 (R&D Systems) to activate the Akt-mTOR-S6 pathway, or IL-6 to stimulate STAT3 phosphorylation. The cells were then fixed and permeabilized as described, and then stained for CD3, CD4 (STAT3 experiments), phosphorylated STAT3 Y705, and phosphorylated S6.

RORgammaT Expression by RT-PCR

To optimize the detection of RORgammaT expression, CD4+ T-cells were isolated by magnetic bead negative selection (Miltenyi Biotec, Auburn, Calif. USA). The human CD4+ T-cells were then stimulated with cytokine-matured, allogeneic monocyte-derived dendritic cells (moDC) (DC: T-cell ratio of 1:30) for 5 days as previously described (Florida Blood Services) [Betts, B C, et al. (2011) Blood 118:5330-9; Betts, B C, et al. (2013) J Leukoc Biol. 2014 95(2):205-13; Betts, B C, et al. (2011) Blood 118:5340-3]. The allogeneic co-cultures were treated with DMSO, rapamycin 10 ng/ml, S3I-201 5 or 50 nM, or both inhibitors at low doses where added once on day 0. The media was supplemented with IL-6 (10$^5$ IU/ml), TGF-beta (4 ng/ml, R&D Systems), and anti-IFN-gamma mAb (10 ng/ml, eBioscience) to promote RORgammaT polarization. After the 5 day culture, the T-cells were harvested. Total RNA was extracted using TRIZOL (Life Technologies) according to manufacturer instructions. Complementary DNA was synthesized using SuperScript® III First-Strand Synthesis System (Life Technologies). RT-PCR was carried out on an ABI 7900 instrument (Applied Biosystems) and performed [Ratajewski, M, et al. (2012) J Immunol 189:3034-42] with some modification using SYBR® Green PCR Master Mix (Life Technologies) as follows: 10 minutes at 95° C. and then 45 cycles each at 95° C. for 15 seconds, 59° C. for 45 seconds, and 72° C. for 10 seconds. The following primers were used: RORgammaT forward 5'-CTGCT-GAGAAGGACAGGGAG-3' (SEQ ID NO:7) and reverse 5'-AGTTCTGCTGACGGGTGC-3'(SEQ ID NO:8); GAPDH forward 5'-ACCACAGTCCATGCCATCAC-3' (SEQ ID NO:9) and reverse 5'-TCCAC-CACCCTGTTGCTGTA-3' (SEQ ID NO:10). PCR product purity was assessed by dissociation curves. The differences in gene expression were calculated by 2-ΔΔCt in triplicate. Data were normalized to GAPDH expression.

Allogeneic Mixed Leukocyte Reactions (alloMLR)

Primary alloMLR:

Bulk donor T-cells were allostimulated with cytokine-matured, allogeneic moDCs at a DC:T-cell ratio of 1:30 as previously described (Florida Blood Services) [Betts, B C, et al. (2011) Blood 118:5330-9; Betts, B C, et al. (2013) J Leukoc Biol. 2014 95(2):205-13; Betts, B C, et al. (2011) Blood 118:5340-3]. Rapamycin (10 ng/ml) with or without S3I-201 (500 nM-50 nM), or DMSO diluent control, were added once only on day 0. Lower doses of each drug were used in these experiments to mimic expected physiologic concentrations [Siddiquee, K, et al. (2007) Proceedings of the National Academy of Sciences of the United States of America 104:7391-6; Zeiser, R, et al. (2008) Blood 111: 453-62], and to better detect potential synergistic activity with the combination of rapamycin and S3I-201. After 5 days of culture at 37° C., T-cell proliferation was measured by a colorimetric assay per the manufacturer's instructions (CellTiter 96 Aqueous One Solution Cell Proliferation Assay [MTS]; Promega, Madison, Wis. USA) [Betts, B C, et al. (2011) Blood 118:5330-9; Betts, B C, et al. (2013) J Leukoc Biol. 2014 95(2):205-13; Betts, B C, et al. (2011) Blood 118:5340-3]. Absorbance/optical density (OD) was analyzed at 490 nm. Secondary alloMLR: T-cells were first DC-allostimulated (DC:T-cell ratio of 1:30) for 5 days with no vehicle or drugs added. Following priming, the T-cells were then rested and re-cultured with fresh first-party moDCs (DC:T-cell ratio of 1:30). DMSO, rapamycin (10 ng/ml), S3I-201 (5 or 50 nM), or rapamycin (10 ng/ml) with S3I-201 (5 μm) were added once on day 0 of the secondary alloMLR. After 3 days, T-cell proliferation was measured by a colorimetric assay as described (Promega). T-cells alone and PHA-stimulated T-cells served as negative and positive controls, respectively, for both the primary and secondary alloMLRs.

Statistical Analysis Statistical differences in patient characteristics were determined by Fisher's exact test for proportions. ROC curves evaluated the sensitivity and specificity of STAT3 phosphorylation with regard to acute GVHD onset. A cut-point of 48% STAT3 phosphorylation among the CD4+ T-cells was selected to distinguish those at risk to develop grade II-IV acute GVHD by day +100 to maximize the area under the ROC curve. The cumulative incidence rate of grade II-IV acute GVHD was estimated among those with < and ≥48% CD4+ STAT3 phosphorylation, where death and relapse were considered competing risks. The Gray method was used to evaluate the difference in incidence rates between the two groups [Fine, J P and Gray, R J. (1999) Journal of the American Statistical Association 94]. GVHD IHC data are presented as absolute numbers for each, and ratio of each to total CD4+ cells. For comparisons of matched data sets, the paired t test was used. For comparisons of independent data sets, the unpaired Student t test or Mann-Whitney test was used based on Gaussian distribution. ANOVA was used for group comparisons. The log-transformation was taken to meet the assumptions for ANOVA. Logistic regression analysis was used to study the association between lymphocyte subset numbers and response to primary GVHD systemic glucocorticoid therapy. The statistical analysis was conducted using SAS 9.3 (SAS Institute Inc, Cary, N.C. USA) and Prism software, ver. 5.04 (GraphPad, San Diego, Calif. USA). Statistical significance was defined by $P<0.05$.

Results

STAT3 Phosphorylation Identifies Those Patients at Risk for Acute GVHD

Figure 8A:
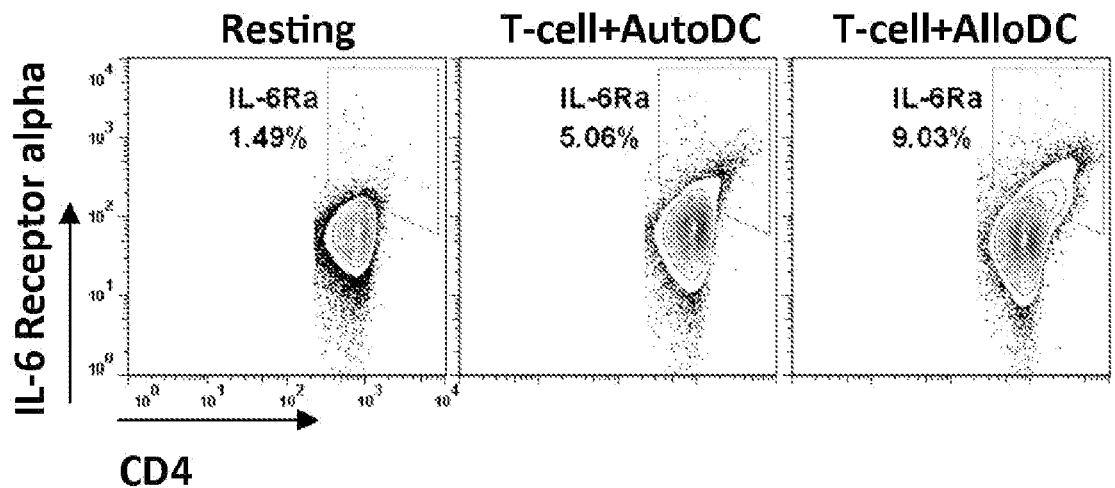
FIG. 8. CD4+ T-cell STAT3 phosphorylation identifies those at risk for acute GVHD. (A,B) Representative contour plots and bar graph (means from 3 independent experiments) depict CD4+ T-cell surface expression of IL-6 receptor alpha in response to resting state, 3-day auto-, or 3-day alloDC stimulation. (C-E) Box and whisker plots demonstrate STAT3 phosphorylation (%, geometric MFI ratio, and absolute number) among CD4+ T-cells at day +21 following allogeneic HCT, based on development of grade II-IV acute GVHD by day +100 (n=18). Healthy volunteer data are included as a reference control (n=5). (F) Representative histograms show CD4+ T-cell STAT3 phosphorylation at day +21 in a patient that never acquired GVHD and a patient that later developed grade II lower gastrointestinal acute GVHD at day +43. (G) ROC curves depict the sensitivity and specificity of day +21% STAT3 activation among CD4+ T-cells (AUC 0.95) as a test to identify those at risk to develop acute GVHD. (H) Cumulative incidence of acute GVHD stratified by degree of CD4+ T-cell STAT3 phosphorylation at day +21 post allogeneic HCT. Gray method was used to evaluate the difference in incidence rates between the two groups. (I-K) Box and whisker plots demonstrate STAT3 phosphorylation (%, geometric MFI ratio, and absolute number) among CD8+ T-cells at day +21 following allogeneic HCT, based on development of grade II-IV acute GVHD by day +100. NS=not significant, *P<0.05, P=0.001-0.01, *P=0.0001-0.001, ****P<0.0001.
Figure 8B:
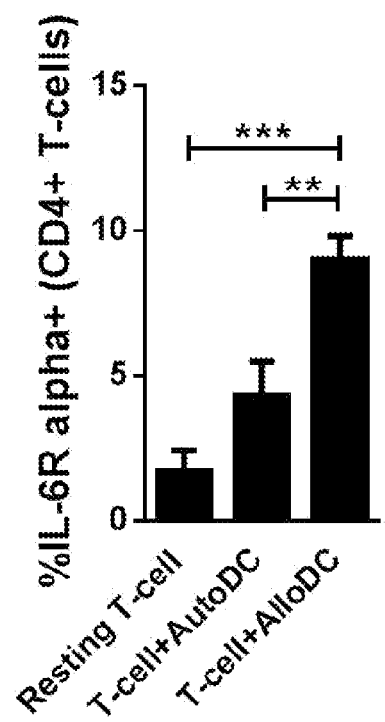

DC-allostimulation significantly increased the surface expression of the IL-6 receptor alpha subunit on healthy donor CD4+ T-cells, compared with resting state or autologous DC-stimulation (FIGS. 8A, 8B). To functionally study this observation in the setting of allogeneic HCT, IL-6-induced STAT3 phosphorylation was measured in T-cells from patients prior to the onset of acute GVHD. A total of 18 patients consented to STAT3 Y705 phosphorylation quantification on day +21 (+/−2 days) and subsequent monitoring for GVHD onset until day +100 at the Moffitt Cancer Center. None of the enrolled patients demonstrated any signs of acute GVHD at time of the day +21 peripheral blood collection. Baseline patient characteristics and clinical variables are summarized in Table 1. The median time of grade II-IV acute GVHD onset was 36 (24-65) days. All cases of acute GVHD occurred before day +100, even when the monitoring period was extended to day +180 to capture potential incidences of late acute GVHD.

TABLE 1

Characteristics of patients where STAT3 phosphorylation was measured on day +21.

|  | GVHD Grade 0-I (N = 10) | GVHD Grade II-IV (N = 8) | P value |
|---|---|---|---|
| Age | 57.6 (37-70) | 51.7 (33-70) | NS |
| Gender | 4 female, 6 male | 3 female, 5 male | NS |
| Primary disease |  |  | NS |
| Acute myelogenous leukemia | 7 | 0 |  |
| Myelodysplasia | 2 | 1 |  |
| Myeloproliferative neoplasm | 0 | 1 |  |
| Acute lymphoblastic leukemia | 1 | 2 |  |
| Chronic myelogenous leukemia | 0 | 1 |  |
| Chronic lymphocytic leukemia | 0 | 0 |  |
| Non-Hodgkin lymphoma | 0 | 2 |  |
| Multiple Myeloma | 0 | 1 |  |
| Conditioning |  |  | NS |
| Myeloablative | 7 | 3 |  |
| Reduced-intensity | 3 | 5 |  |
| GVHD Prophylaxis |  |  | NS |
| Rapa/TAC | 8 | 5 |  |
| MTX/TAC | 1 | 2 |  |
| Mycophenolate Mofetil/TAC | 1 | 1 |  |
| Graft source |  |  | N/A |
| Peripheral blood stem cells | 10 | 8 |  |
| Marrow | 0 | 0 |  |
| Donor relation |  |  | NS |
| HLA-matched related | 2 | 4 |  |
| HLA-matched unrelated | 8 | 4 |  |
| Female donor => Male recipient | 2 | 1 |  |
| Acute GVHD grade II-IV | N/A |  | N/A |
| II |  | 6$^a$ |  |
| III |  | 1$^b$ |  |
| IV |  | 1$^c$ |  |

Figure 8C:
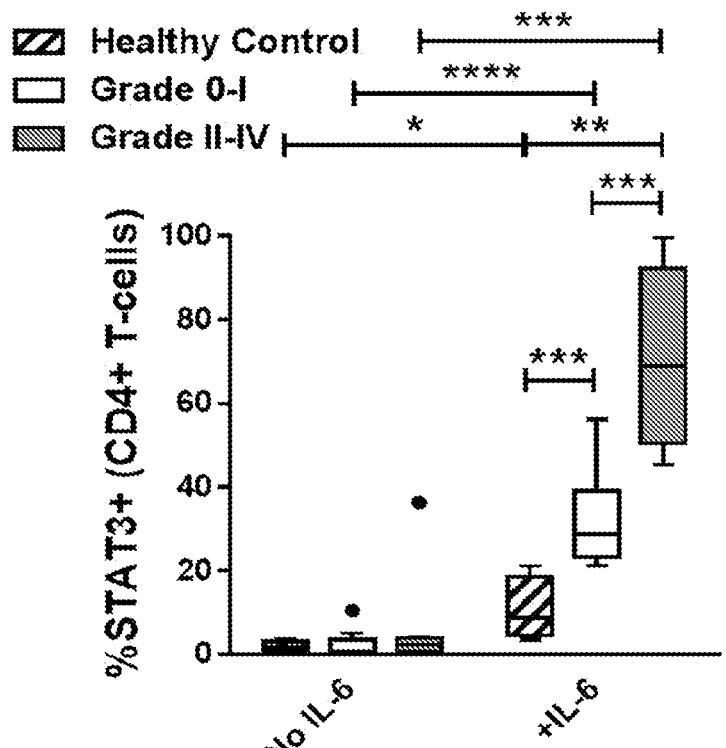
Figure 8D:
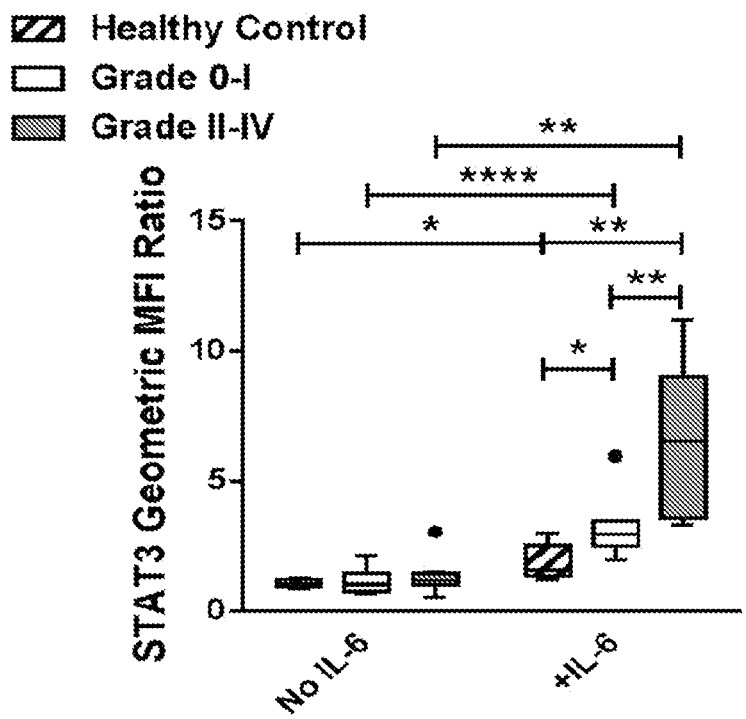
Figure 8E:
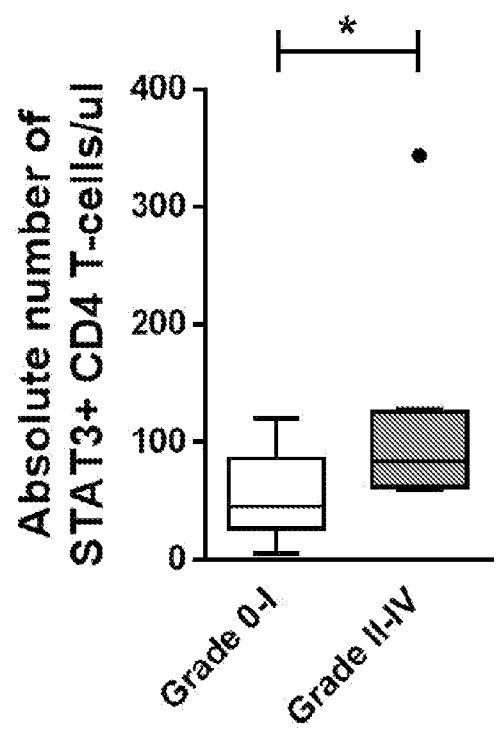
Figure 8F:
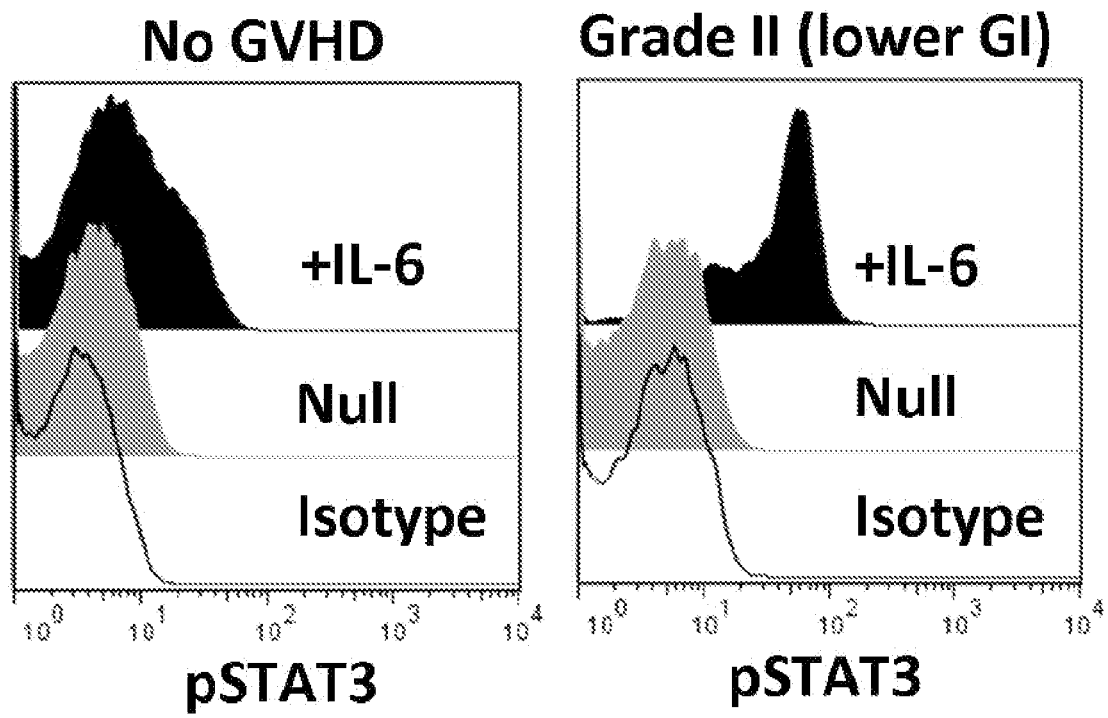
Figure 16A:
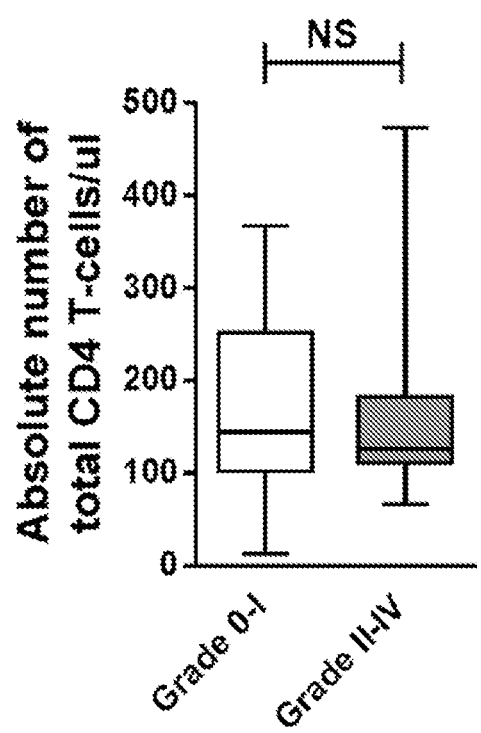
FIGS. 16A and 16B. Box and whisker plots show the absolute number of total CD4+ and CD8+ T-cells at day +21 following allogeneic HCT, based on development of grade II-IV acute GVHD by day +100. NS=not significant. N=10 Grade 0-I and 8 Grade II-IV.

NS = not significant,
NA = not applicable
$^a$4 patients with stage 1 lower GI acute GVHD, 2 patients with stage 3 skin acute GVHD
$^b$1 patient with stage 4 lower GI acute GVHD
$^c$1 patient with stage 4 skin acute GVHD Patients that developed grade II-IV acute GVHD by day +100 demonstrated a significant increase in STAT3 Y705 phosphorylation among CD4+ T-cells pulsed with IL-6, compared with either healthy volunteers or patients with grade 0-I acute GVHD (FIGS. 8C, 8D). Both the percentage of STAT3 activation among CD4+ T-cells and relative intracellular antigen density (STAT3 geometric MFI ratio normalized to isotype negative control autofluorescence) of the stimulated CD4+ T-cells were highly expressed in patients who eventually developed acute GVHD (FIGS. 8C, 8D, 8F). The absolute number of IL-6-responsive STAT3+ CD4 T-cells at day +21 was increased among those who later developed grade II-IV acute GVHD (FIG. 8E). The absolute number of total CD4+ T-cells was similar among both groups of patients (FIG. 16A). The amount of STAT3 activation did not directly correlate with the grade-wise severity or rapidity of GVHD onset during the 100 days following allogeneic HCT.

Figure 8G:
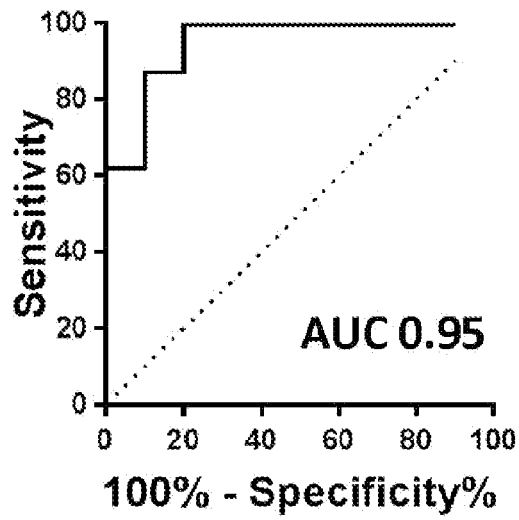

Receiver operator characteristic (ROC) curves were generated to test the ability of CD4+ T-cell STAT3 Y705 phosphorylation to discriminate among those with and without grade II-IV acute GVHD by day +100. The area under the curve (AUC) for percent STAT3 activation among CD4+ T-cells was 0.95 (FIG. 8G), and 0.87 for the STAT3 geometric MFI ratio. A cut-off point of 48% STAT3 Y705 phosphorylation among CD4+ T-cells demonstrated a test sensitivity of 87.5% and specificity of 90% with a likelihood ratio of 8.75. Though patients with nausea and/or anorexia alone were analyzed within the grade 0-I group to minimize confounding etiologies, a secondary analysis demonstrated similar results when these patients were considered to have grade II upper gastrointestinal GVHD (CD4+ % pSTAT3+ P=0.02 with AUC of 0.84; STAT3 geometric MFI ratio P=0.01 with AUC of 0.84).

Figure 8H:
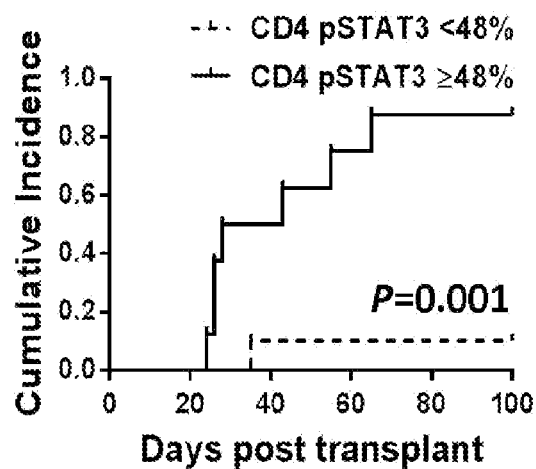
Figure 8I:
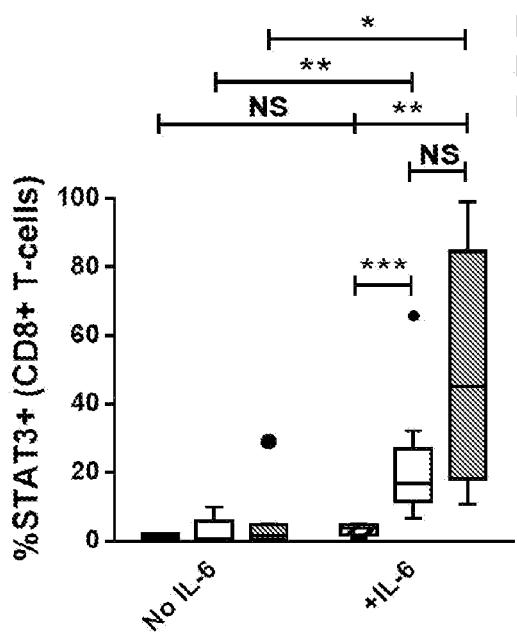
Figure 8J:
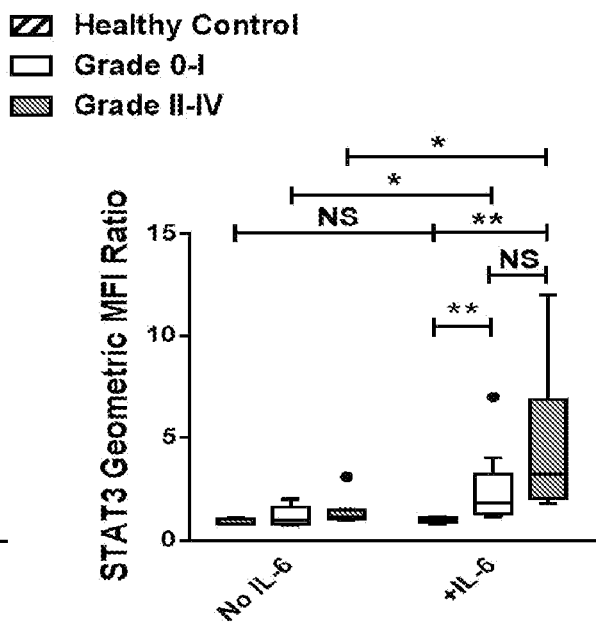
Figure 8K:
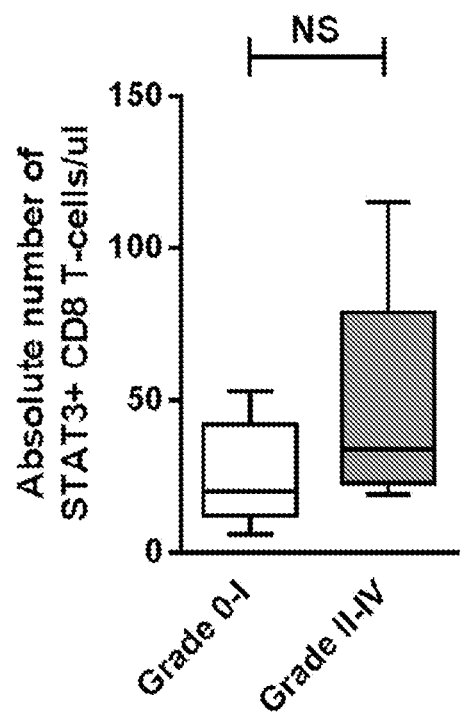
Figure 16B:
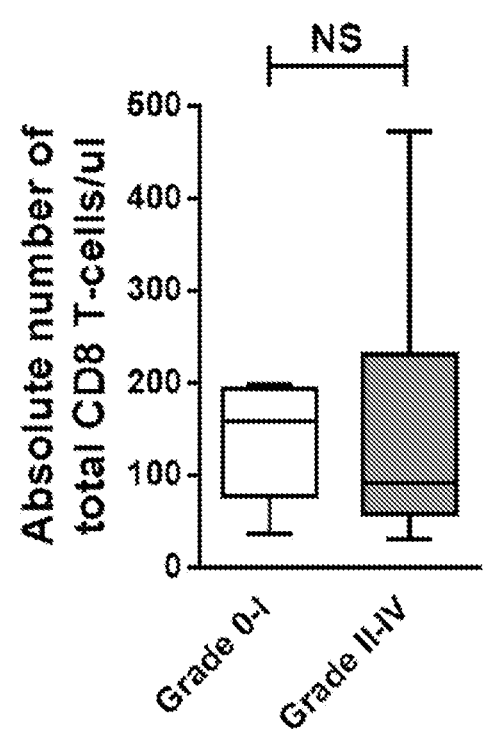

Using the selected cut-off point of 48% STAT3 activation among CD4+ T-cells, the cumulative incidence of grade II-IV acute GVHD was estimated for patients with % STAT3+Y705 phosphorylation values < and ≥48%. This approach significantly stratified those at risk to develop grade II-IV acute GVHD, based on the enhanced degree of STAT3 activation at day +21—prior to clinical recognition of alloreactivity (FIG. 8H). The degree of STAT3 phosphorylation among CD8+ T-cells was similar among those with or without GVHD, though both patient groups showed greater STAT3 activity than the healthy volunteers (FIGS. 8I, 8J). The absolute number of IL-6-responsive STAT3+ CD8+ T-cells and total CD8+ T-cells were not statistically different among those with or without acute GVHD (FIGS. 8K, 16B).

The Amount of Tissue-Resident $T_H17$ Correlates with GVHD Severity, Rapamycin GVHD Prophylaxis, and Glucocorticoid Response A total of 48 patients contributed 110 GVHD biopsies to the analysis. These samples were obtained from patients randomized to rapamycin (n=25) or methotrexate (n=23) in a GVHD prevention trial (NCT00803010)[Pidala, J, et al. (2012) Haematologica 97:1882-9]. Acute GVHD organ biopsy sites, as well as clinical and pathologic grade are represented in Table 2. GVHD diagnostic biopsies were not required by protocol, and all available biopsies were included in this analysis. While the total rapamycin-treated study population had reduction in grade II-IV acute GVHD [Pidala, J, et al. (2012) Haematologica 97:1882-9], the clinical grade distribution presented reflects that of biopsied patients. Comparison of GVHD-affected patients according to biopsy status is presented in Table 3. Time from GVHD biopsy to topical (P=0.17) or systemic glucocorticoid (P=0.55) therapy did not differ between *Rapa* and MTX-treated patients. RORgamma and CD4 co-registration analysis demonstrated that the majority of RORgamma+ cells were dual positive for CD4 (median 98%, range 89-99.6%). There was a low background of ILC3 cells in a subset of patients (n=24) who had cores dually-stained for CD3 and RORgamma ILC3 (CD3 negative, RORgamma+) only comprised an average of 6.3% of total RORgamma+ cells (FIG.

Figure 2C:
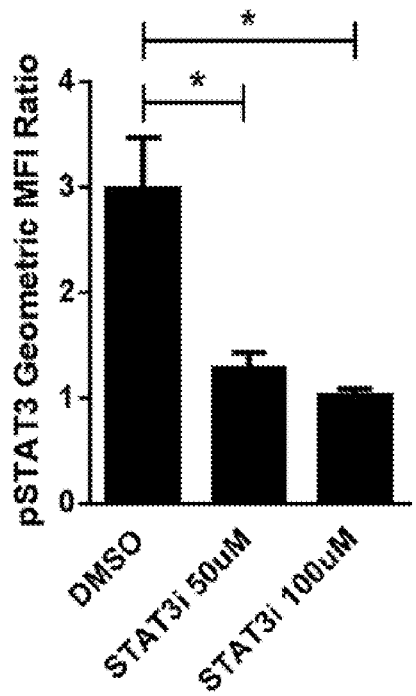
Figure 2D:
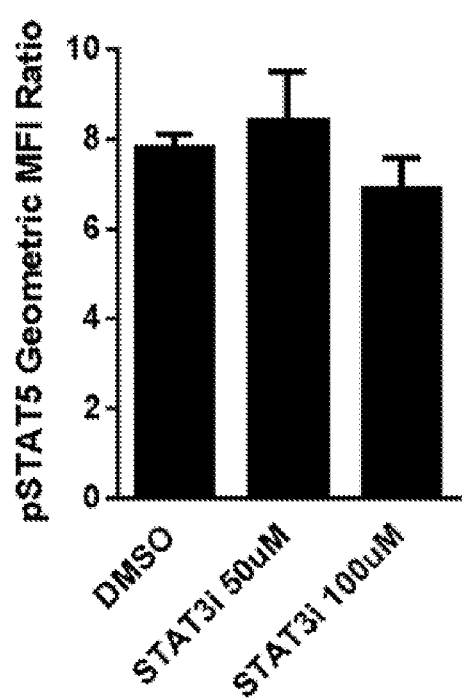
Figures 9A, 9B:
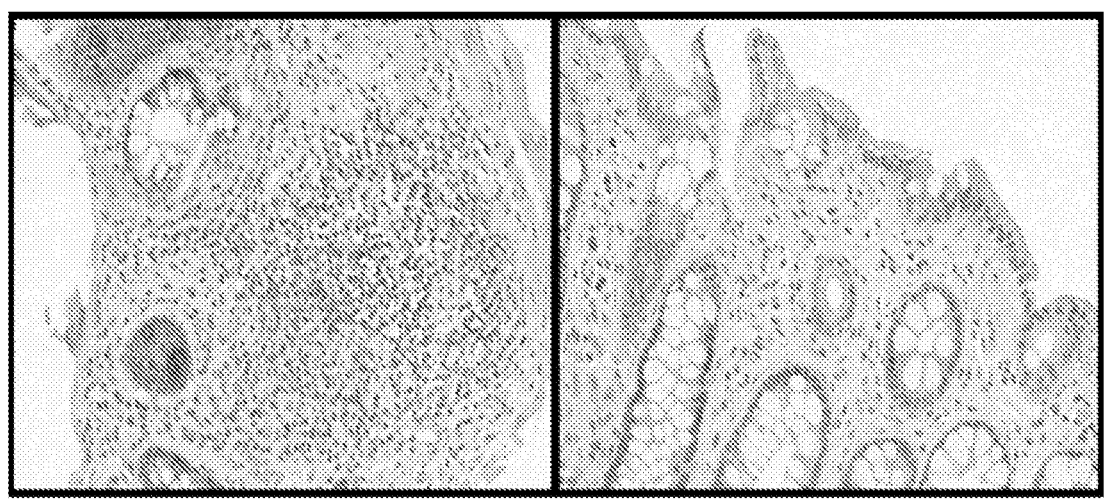
FIG. 9. Tissue-resident Th17 cells are associated with severity of GVHD pathologic grade. (A) shows increased RORgamma positive lymphocytes in a rectal biopsy from a patient with pathologic grade 3 GVHD. (B) shows fewer RORgamma positive lymphocytes in a rectal biopsy from a patient with pathologic grade 1 GVHD. [RORgamma, ×400]. Box and whisker plots show absolute number of tissue-resident Th17 (C), Th1 (D), and Treg (E) by pathologic GVHD grade. (F) Co-expression of CD3 (red) and RORgamma (brown) is shown in a representative biopsy image, confirming the exclusion of ILC3s (CD3 negative, RORgamma+) [×200, inset ×400]. (G) Co-expression of IL-17 (red) and RORgamma (brown) is shown in a representative biopsy image [×200, inset ×400]. NS=not significant, *P<0.05.
Figure 9C:
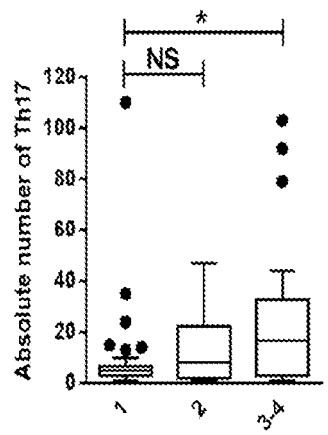
Figure 9D:
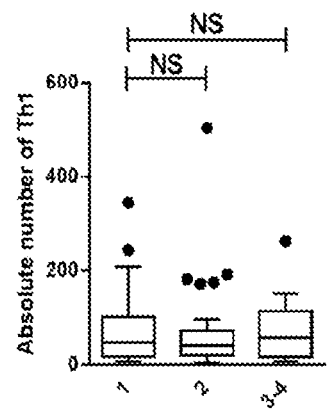
Figure 9E:
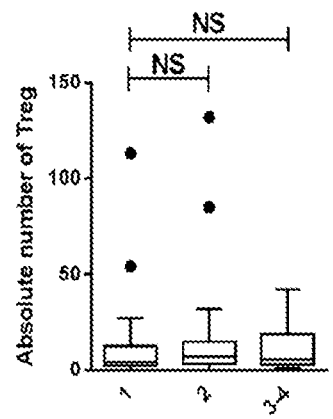
Figure 9F:
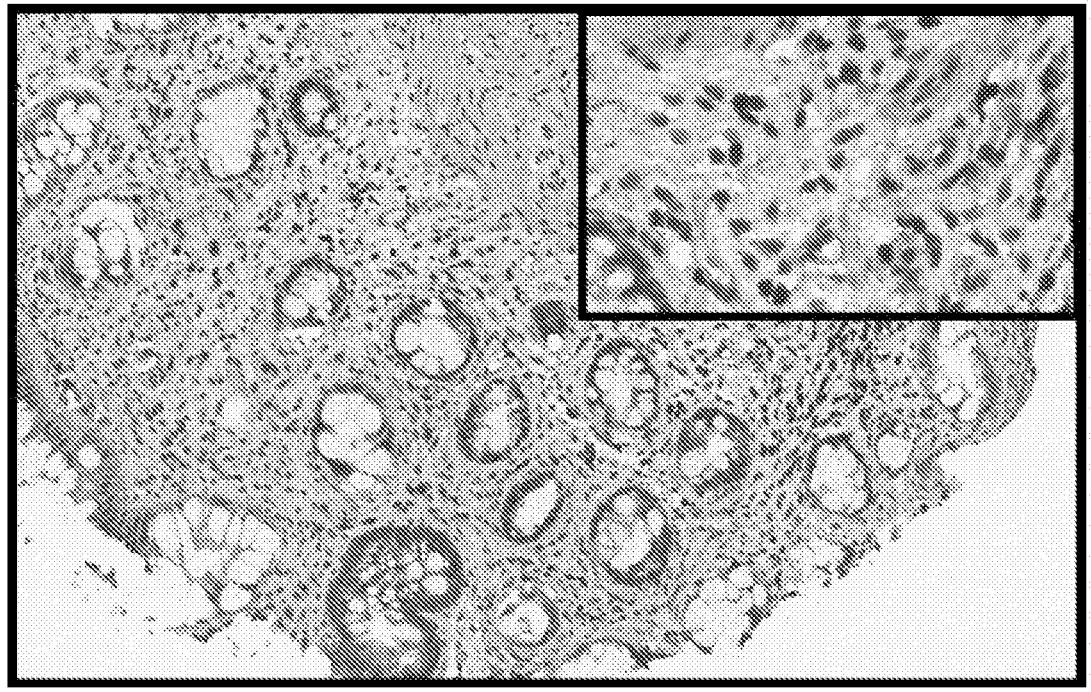
Figure 9G:
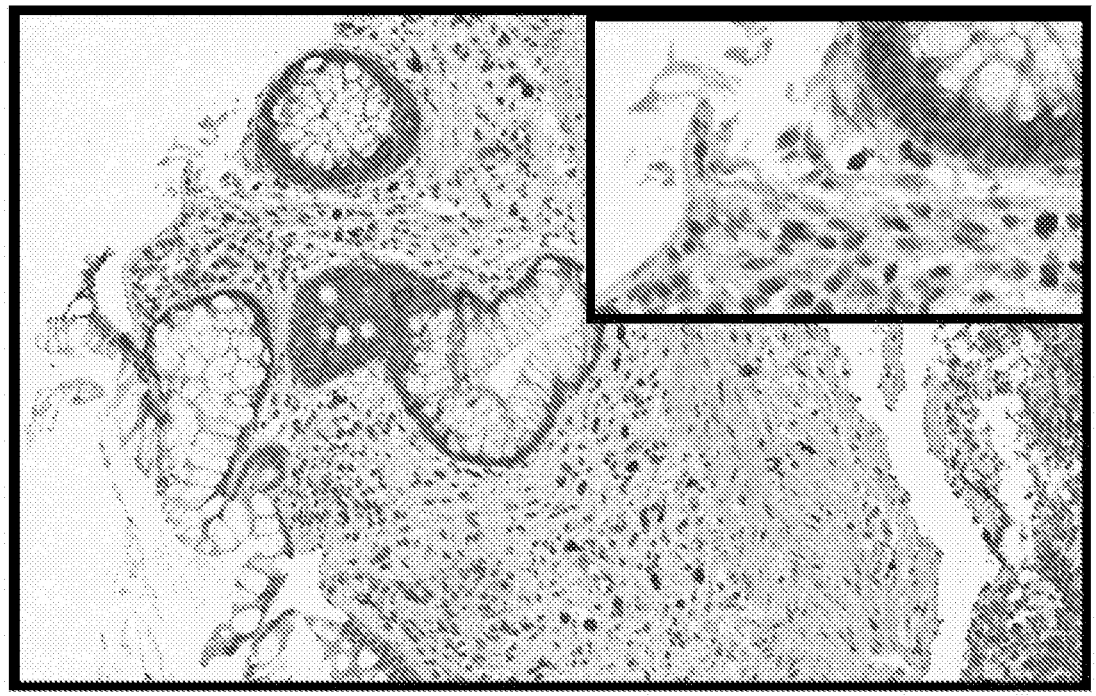

9F). There was a high degree of RORgamma/IL-17 co-expression among the dual stained cores (FIG. 9G). Thus, $T_H17$ were subsequently defined by RORgamma positivity. $T_H17$ increased (median values—grade 1: 5, grade 2: 8, grade 3: 20.5) with pathologic grade. ANOVA adjusted for GVHD organ site demonstrated that $T_H17$ (P=0.033) were significantly associated with pathologic grade (FIG. 2A-C). No other cell subsets were associated with pathologic grade (FIG. 9D, 9E).

Figures 11A, 11B:
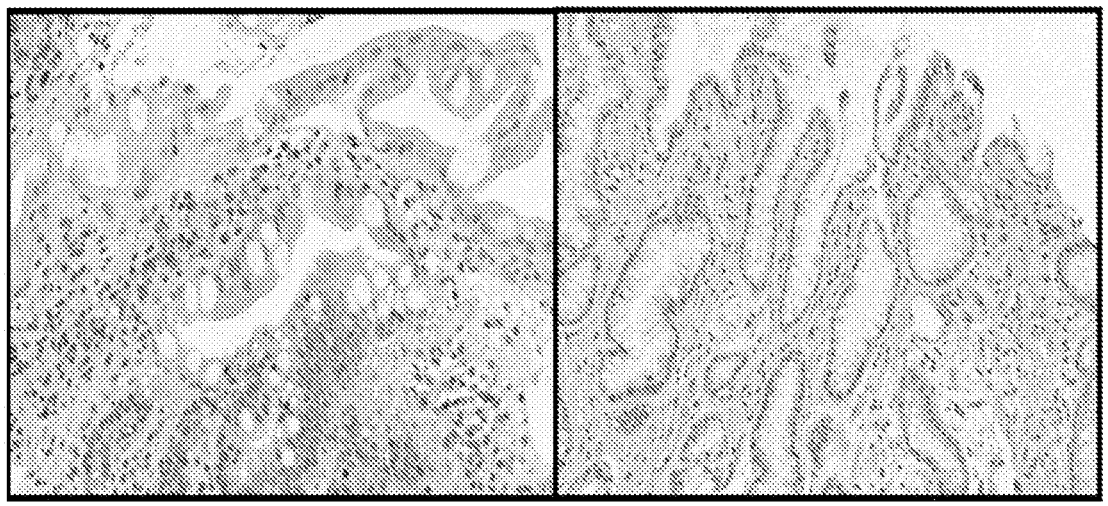
FIG. 11. Target-organ Th17 cells are reduced among those receiving rapamycin GVHD prophylaxis. (A) shows increased RORgamma positive lymphocytes in the duodenal lamina propria from a patient receiving methotrexate. (B) shows fewer RORgamma positive lymphocytes in the duodenal lamina propria of a patient receiving rapamycin. Both patients were diagnosed with pathologic grade 2 GVHD. [RORgamma, ×400]. Box and whisker plots show absolute number of tissue-resident Th17 (C), Th1 (D), and Treg (E) by use of rapamycin or methotrexate GVHD prophylaxis. Line depicts median. NS=not significant, *P<0.05.
Figure 11C:
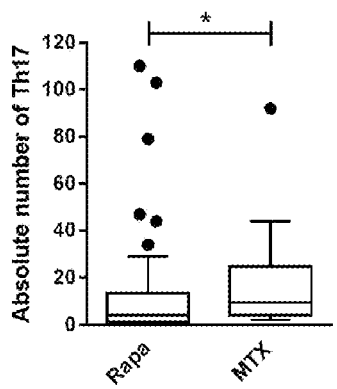
Figure 11D:
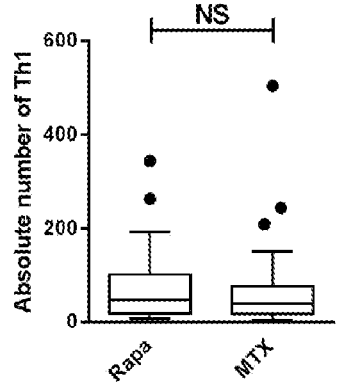
Figure 11E:
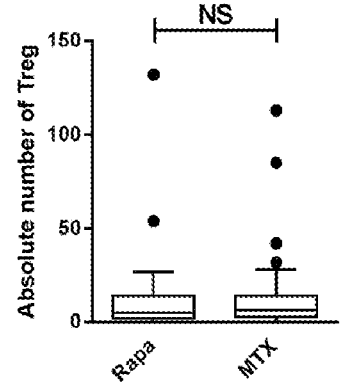

Other lymphocyte subsets did not differ between rapamycin and methotrexate treatment (FIG. 11D, 11E).

Refractoriness to standard initial acute GVHD therapy (≥1 mg/kg/day prednisone or equivalent) was defined as lack of complete or partial response by 28 days of therapy, as this is a validated predictor of subsequent non-relapse mortality [Levine, J E, et al. (2010) Biol Blood Marrow Transplant 16:1693-9]. Those with refractory acute GVHD had a significantly increased number of $T_H17$ present in affected

TABLE 2

GVHD organ involvement, pathologic, and clinical grade

|  |  | Rapa (%) | MTX(%) | TOTAL(%) | P value |
|---|---|---|---|---|---|
| Pathologic grade | 1 | 23 (38.3) | 15 (31.9) | 38 (35.5) | NS |
|  | 2 | 26 (43.3) | 21 (44.7) | 47 (43.9) |  |
|  | 3 | 11 (18.3) | 9 (19.1) | 20 (18.7) |  |
|  | 4 | 0 (0) | 2 (4.3) | 2 (1.9) |  |
|  | Total | 60 (56.1) | 47 (43.9) | 107 (100) |  |
| Biopsy organ site | Gastric antrum | 15 (23.8) | 12 (25.5) | 27 (24.5) | NS |
|  | Duodenum | 18 (28.6) | 12 (25.5) | 30 (27.3) |  |
|  | Rectum | 19 (30.2) | 15 (31.9) | 34 (30.9) |  |
|  | Liver | 1 (1.6) | 2 (4.3) | 3 (2.7) |  |
|  | Skin | 10 (15.9) | 6 (12.8) | 16 (14.5) |  |
|  | Total | 63 (57.3) | 47 (42.7) | 110 (100.0) |  |
| Clinical grade a,b, c | 1 | 9 (36) | 0 (0) | 9 (19) | <0.001 |
|  | 2 | 11 (44) | 21 (91) | 32 (67) |  |
|  | 3 | 4 (16) | 2 (9) | 6 (13) |  |
|  | 4 | 1 (4) | 0 (0) | 1 (2) |  |
|  | Total | 25 (52) | 23 (48) | 48 (100) |  |

Rapa = rapamycin/tacrolimus GVHD prophylaxis group,
MTX = methotrexate/tacrolimus GVHD prophylaxis group,
NS = not significant
a Clinical grade distribution reflects that of the represented biopsies, not the grade distribution of the total parent study population. Biopsies were not mandated per protocol, and thus were obtained per treating clinicians' judgment.
b Clinical grade distribution presented for patient-level data (number of patients for each overall clinical grade), while pathologic grade and biopsy site represent individual biopsy-level data.
c Overall grade distribution across study groups (Rapa vs. MTX) compared using Fisher exact test. Separate comparison of grade ½ vs. ¾ showed no significant difference (P = 0.42).

TABLE 3

Overall clinical grade distribution for GVHD-affected patients according to biopsy status

| Group | Overall clinical grade of acute GVHD Frequency (%) | | | | | p value* |
|---|---|---|---|---|---|---|
|  | 1 | 2 | 3 | 4 | total |  |
| MTX biopsy | 0 (0) | 21 (91) | 2 (9) | 0 (0) | 23 (38) | 0.003 |
| MTX no biopsy | 2 (17) | 8 (67) | 2 (17) | 0 (0) | 12 (20) |  |
| RAPA biopsy | 9 (36) | 11 (44) | 4 (16) | 1 (4) | 25 (41) |  |
| RAPA no biopsy | 1 (100) | 0 (0) | 0 (0) | 0 (0) | 0 (0) |  |
| Total | 12 (20) | 40 (66) | 8 (13) | 1 (2) | 61 (100) |  |

Figures 10A, 10B:
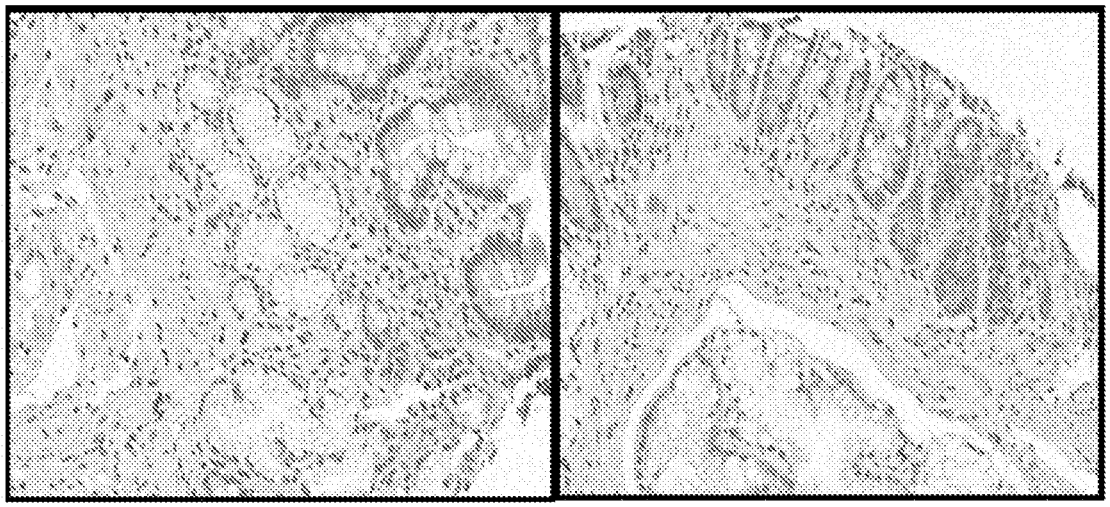
FIG. 10. The target-organ Th17/CD4+ and Treg/CD4+ T-cell ratios are increased in clinical stage 3 or 4 gastrointestinal GVHD. (A) shows increased RORgamma positive lymphocytes in a duodenal biopsy from a patient with clinical stage 3 acute GVHD. (B) shows fewer RORgamma positive lymphocytes in a duodenal biopsy from a patient with clinical stage 1 acute GVHD. [RORgamma, ×400]. Box and whisker plots show ratio of tissue-resident Th17/CD4+ (C), Th1/CD4+ (D), and Treg/CD4+ (E) T-cells by gastrointestinal GVHD clinical stage. NS=not significant, *P=0.0001-0.001, **P<0.0001.
Figure 10C:
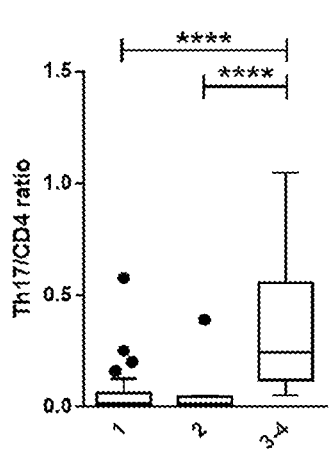
Figure 10D:
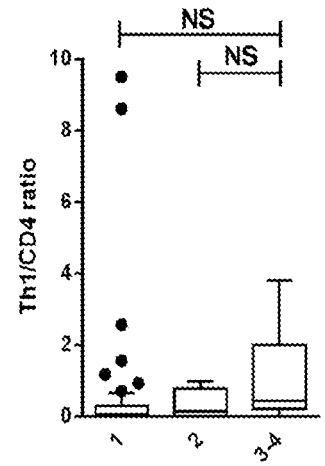
Figure 10E:
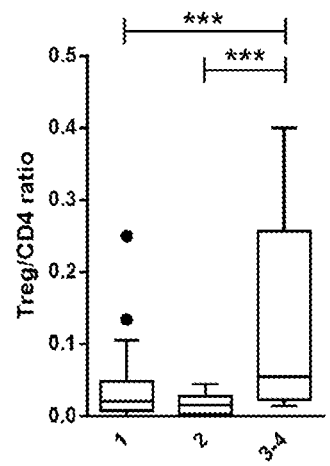

*Fisher's exact test comparison of overall clinical grade distribution per biopsy status An analysis of GI clinical stage, with an ANOVA adjusted for GI organ involvement, demonstrated that the $T_H17$/CD4 and Treg/CD4 ratios increased with greater GI organ stage (FIGS. 10A-10C, 10E). Th1 tissue-deposition was not associated with GI GVHD stage FIG. 10D). There were too few biopsies of skin and liver for organ-specific analysis.

Rapamycin-treated patients had significantly lower $T_H17$ cells than those treated with methotrexate (FIG. 11A-11C). Adjusted for clinical and pathologic grade, rapamycin remained significantly associated with lower $T_H17$ (P=0.04).

tissues compared to responsive (median 27 vs. 5) (FIG. 12A-12C). Logistic regression analysis demonstrated that tissue $T_H17$ were significantly associated with glucocorticoid refractoriness (OR 6.6, 95% CI 1.6-27, P=0.008), as was overall clinical GVHD grade (grade 3-4 vs. 2: OR 6.3, 95% CI 1.7-23.0, P=0.01). $T_H17$ was also significantly associated with refractoriness in a sub-group analysis limited to GI involvement. Other lymphocyte subsets were not associated with glucocorticoid refractoriness (FIG. 12D, 12E).

Differential Effects of S3I-201 and Rapamycin on mTOR and STAT3 Signaling

Figure 13A:
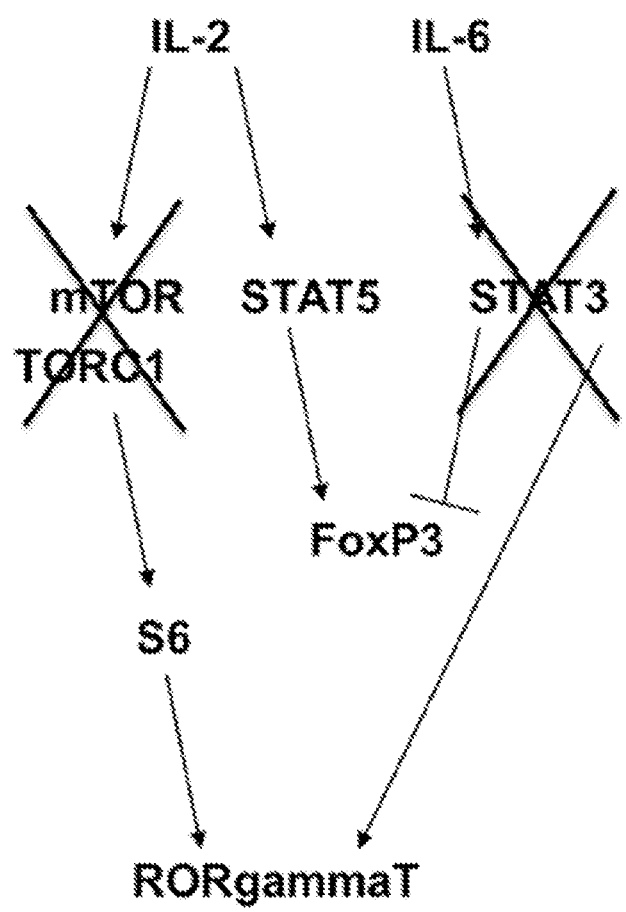
FIG. 13. Differential effects of S3I-201 and rapamycin on mTOR and STAT3 Y705 signaling. (A) Signaling schema of mTOR and STAT3 Y705 pathways that converge upon RORgammaT. Human T-cells were DC-allostimulated for 3 days to optimize STAT3 signaling. T-cells were harvested and serum-starved in the presence of DMSO, rapamycin 100 ng/ml, or STAT3i (S3I-201, STAT3 inhibitor) 50 uM for 4 hours, then pulsed with IL-2 or IL-6 to induce S6 ribosomal protein or STAT3 Y705 phosphorylation, respectively. (B) The means±SD from 5 independent experiments show rapamcyin has a negligible effect on STAT3 Y705 phosphorylation (the residue associated with RORgammaT expression), though Y705 is susceptible to STAT3i. (C) Representative histograms show the effect of mTOR and STAT3 blockade on STAT3 activation. (D) The means±SD from 5 independent experiments demonstrate that rapamycin significantly suppresses S6, while STAT3i imparts partial inhibition. (E) Representative contour plots show the impact of mTOR and STAT3 blockade on S6 signaling. *P<0.05, P=0.001-0.01, *P=0.0001-0.001.
Figure 13B:
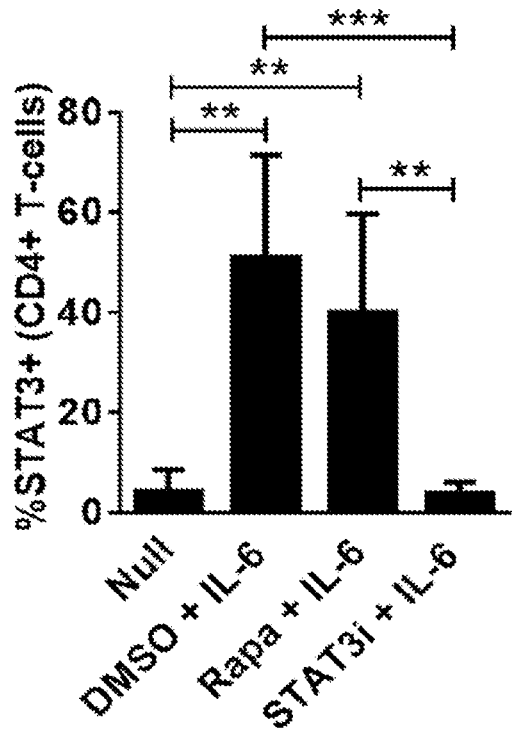
Figure 13C:
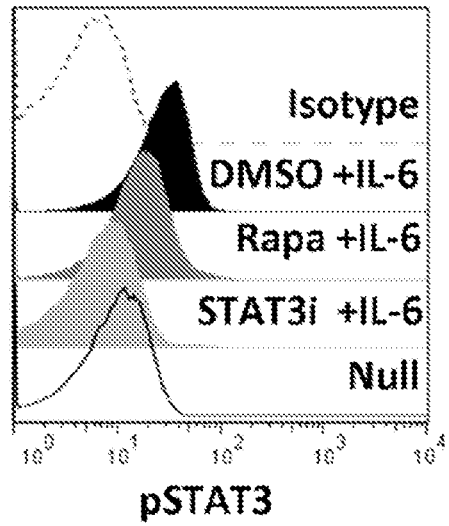
Figure 13D:
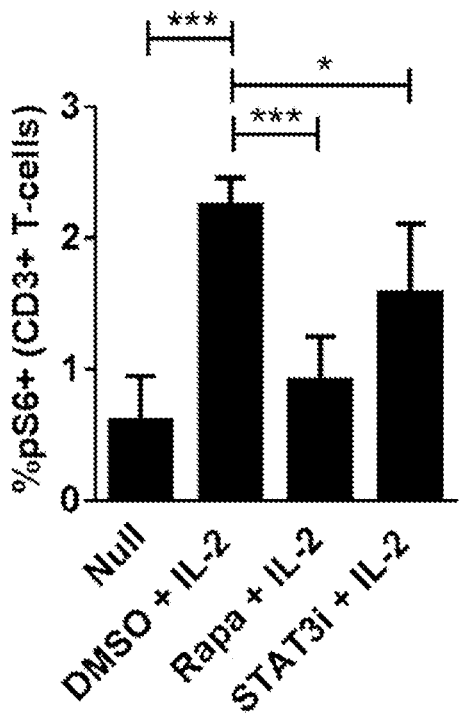
Figure 13E:
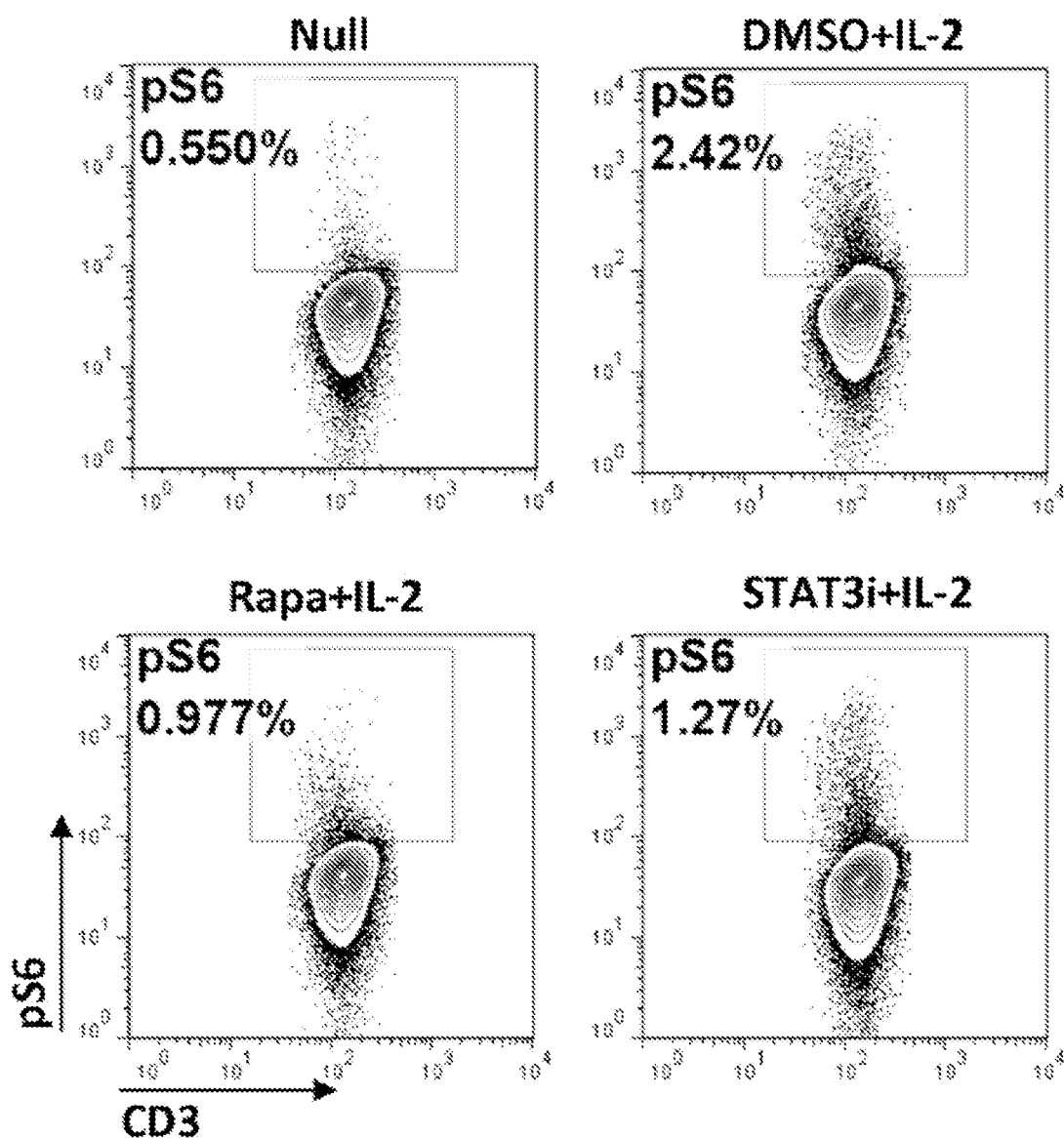

While rapamycin-based immune suppression is associated with a reduction in tissue-resident $T_H17$ during acute GVHD, it incompletely protects HCT recipients from alloreactivity [Pidala, J, et al. (2012) Haematologica 97:1882-9]. Rapamycin inhibits phosphorylation of the STAT3 Ser727 motif but does not affect the Y705 motif that is important for RORgammaT transcription [Kurebayashi, Y, et al. (2012) Cell reports 1:360-73; Ueda, A, et al. (2012) J Immunol 188:5247-56]. In contrast, S3I-201 predominantly inhibits phosphorylation of the STAT3 Y705 motif and much less the Ser727 motif [Kurebayashi, Y, et al. (2012) Cell reports 1:360-73; Siddiquee, K, et al. (2007) Proceedings of the National Academy of Sciences of the United States of America 104:7391-6; Ueda, A, et al. (2012) J Immunol 188:5247-56]. Therefore, the differential effects of rapamycin and S3I-201 on the Akt-mTOR-S6 and STAT3 signaling pathways was investigated (FIG. 6A). S3I-201 significantly decreased IL-6-mediated STAT3 phosphorylation of Y705 in cytokine-pulsed T-cells from healthy random donors (FIG. 13B, 13C) [Betts, B C, et al. (2013) J Leukoc Biol. 2014 95(2):205-13]. mTOR inhibition with rapamycin demonstrated little effect on STAT3 Y705 phosphorylation (FIG. 13B, 13C), but significantly decreased mTOR-dependent S6 signaling in IL-2-stimulated T-cells (FIG. 13D, 13E). S3I-201 modestly reduced S6 activation (FIG. 13D, 13E). These data demonstrate that STAT3 inhibition does not completely suppress mTOR activation, and mTOR inhibition does not suppress STAT3 phosphorylation. This suggests that suppression of both pathways is required to inhibit RORgammaT expression.

Dual STAT3/mTOR Inhibition Exerts Enhanced Control Over RORgammaT Expression and Alloreactivity To investigate the effect of dual STAT3 and mTOR inhibition on RORgammaT expression, moDC-allostimulated CD4+ T-cells were exposed to DMSO, S3I-201, rapamycin, or both inhibitors. Both STAT3 and mTOR inhibition independently demonstrated significant suppression of RORgammaT, compared with DMSO diluent control (FIG. 14A). Moreover, the combination of clinically relevant concentrations of rapamycin (10 ng/ml) and S3I-201 (5 µM) achieved superior inhibition of RORgammaT, compared with either rapamycin or S3I-201 alone (FIG. 14A).

Primary, 5-day AlloMLRs (moDC:T-cell ratio of 1:30) were treated with a low, fixed dose of rapamycin (10 ng/ml) combined with varying concentrations of S3I-201 (500 nM-50 µM). This approach was taken to best approximate physiologic drug levels [Siddiquee, K, et al. (2007) Proceedings of the National Academy of Sciences of the United States of America 104:7391-6; Zeiser, R, et al. (2008) Blood 111:453-62] and to optimize detection of any enhanced efficacy by dual STAT3/mTOR inhibition. 50 uM of S3I-201 significantly reduced allostimulated T-cell proliferation [Betts, B C, et al. (2013) J Leukoc Biol. 2014 95(2):205-13]. Additionally, concentrations of S3I-201 below 50 µM had no effect on alloreactive T-cell proliferation as a single agent [Betts, B C, et al. (2013) J Leukoc Biol. 2014 95(2):205-13]. Rapamycin alone modestly affected the alloresponse (P=0.06) (FIG. 14B). However, significant control over the alloresponse was achieved when S3I-201 was added to rapamycin, even at nanomolar concentrations of the STAT3 inhibitor (FIG. 14B). Either rapamycin (10 ng/ml) or S3I-201 (50 µM) alone significantly suppressed T-cell proliferation when added to primed T-cells during rechallenge with fresh, original allogeneic moDCs. Unlike T-cells responding to primary allostimulation, enhanced immune suppression was not observed when both rapamycin (10 ng/ml) and S3I-201 (5 µM) were added to the secondary alloMLR (FIG. 14C).

Discussion

This example shows that STAT3 pathway activation and $T_H17$ tissue invasion are clinically relevant to the pathogenesis of human acute GVHD. DC-allostimulation significantly increases the surface expression of the IL-6 receptor alpha subunit. In a cohort of asymptomatic allogeneic HCT recipients, STAT3 Y705 phosphorylation in circulating CD4+ T-cells is significantly increased by IL-6 in patients who later develop grade II-IV acute GVHD by day +100. Additionally, T-cell STAT3 activation is increased by IL-6 among all HCT patient groups compared with healthy volunteers.

STAT3 signaling is critical for RORgammaT expression and consequent $T_H17$ polarization. Accordingly, at time of acute GVHD diagnosis there was a marked abundance of $T_H17$ cells within the tissues of biopsied target organs. The epithelium was excluded from all tissue analyses to avoid RORgamma staining from non-$T_H17$ cells. Moreover, ILC3 cells (CD3 negative, RORgamma and/or IL-17 positive) were confirmed to comprise a minimal population (6.3%) within the biopsy field of interest using the described double staining procedure, as they similarly express CD4, RORgamma, and IL-17 [Kim, H Y, et al. (2014) Nature medicine 20:54-61; Geiger, T L, et al. (2014) The Journal of experimental medicine 211:1723-31; Longman, R S, et al. (2014) The Journal of experimental medicine 211:1571-83; Munneke, J M, et al. (2014) Blood 124:812-21].

Among the cohort of patients studied at day +21 after allogeneic transplant in this pilot investigation, the degree of phosphorylated STAT3 induced by IL-6 was linked to the eventual onset of acute GVHD. A cut point of 48% STAT3 phosphorylation within the CD4+ T-cells significantly stratifies those at greatest risk of acquiring acute GVHD. For those with <48% STAT3 activation, only 10% of patients developed this post-transplantation complication. Moreover, all of the observed patients with >48% STAT3 phosphorylation developed grade II-IV acute GVHD by day +100. Of note, the amount of phosphoprotein expression did not directly correlate with specific grade-wise assignment, rapidity of disease onset, or specific organ involvement of the observed GVHD. T-cell STAT3 activity is significantly increased in patients with systemic lupus erythematosus (SLE) [Hedrich, C M, et al. (2014) Proc Natl Acad Sci USA. 2014 111(37):13457-62]. Taken together, these observations made in acute GVHD and SLE identify STAT3 activation on T cells as an important factor in human immune-mediated disease.

Rapamycin inhibition of mTOR signaling was associated with a reduction in $T_H17$ burden at time of GVHD diagnosis. In mice, mTOR activation is linked to RORgammaT transcript migration by way of downstream phosphorylation of S6 ribosomal protein [Kurebayashi, Y, et al. (2012) Cell reports 1:360-73]. Interestingly, mTOR inhibition in mice does not affect expression of RORgammaT by the RORC gene [Kurebayashi, Y, et al. (2012) Cell reports 1:360-73]. Additionally, rapamycin is unable to control STAT3-mediated expression of RORgammaT [Ueda, A, et al. (2012) J Immunol 188:5247-56]. While rapamycin does suppress the Ser727 residue of STAT3, it fails to impede signaling via the Y705 motif [Ueda, A, et al. (2012) J Immunol 188:5247-56]. Phosphorylation of Y705 is required for $T_H17$ differentiation [Ueda, A, et al. (2012) J Immunol 188:5247-56]. Human data did show partial inhibition of S6 phosphorylation by S3I-201. Selective inhibitors of upstream JAK2 have demonstrated this effect as well [Zeng, Z Z, et al. (2002) The Journal of biological chemistry 277:41213-9; Couto, J P, et al. (2012) PloS one 7:e46869], suggesting that STAT3 may play a modest role in S6 signaling. Moreover, the most efficient means to prevent RORgammaT expression in human T-cells is achieved through combined inhibition of both mTOR and STAT3 activation.

Superior control over alloreactive T-cells was observed when low, physiologic concentrations of rapamycin and S3I-201 were combined in primary alloMLRs (>95% inhibition with rapamycin 10 ng/ml plus S3I-201 5 µM in comparison to DMSO, FIG. 14B). While single agent rapamycin (10 ng/ml) or S3I-201 (50 µM) partially inhibited the proliferation of primed T-cells in secondary alloMLRs (69% and 67% inhibition in comparison to DMSO, respectively, FIG. 14C), enhanced suppression was not achieved with concurrent pathway blockade in this setting. This suggests that STAT3 inhibition overcomes rapamycin-resistance during the initial T-cell:moDC encounter. Conversely, alternative activation mechanisms may drive the primed alloresponse despite the inhibition of STAT3 and/or mTOR signaling. PTEN is reduced in DC-primed, memory T-cells, which could potentially worsen rapamycin-resistance during the secondary response [Lozza, L, et al. (2008) European journal of immunology 38:30-9].

the significant increase in STAT3 activation among CD4+ T-cells in patients who go on to develop acute GVHD indicates that $T_H17$ contributes to acute GVHD. The amount of $T_H17$ cells was significantly associated with pathologic grade, clinical stage of gastrointestinal GVHD, and poor response to upfront glucocorticoids. These findings indicate a potential association between STAT3 activation prior to GVHD onset and the resultant deposition of $T_H17$ cells among the involved GVHD target-organs. Others have reported a lack of an association between $T_H17$ tissue deposition and acute GVHD onset [Broady, R, et al. (2010) Blood 116:5748-51; Ratajczak, P, et al. (2010) Blood 116: 1165-71]. These divergent findings may be explained by the current use of RORgammaT as a selective marker to identify $T_H17$ within the target tissues. Conversely, others stained acute GVHD biopsy samples for the IL-17 cytokine [Broady, R, et al. (2010) Blood 116:5748-51; Ratajczak, P, et al. (2010) Blood 116:1165-71], as opposed to the more specific transcription factor responsible for $T_H17$ differentiation. In agreement with existing published work, tissue-resident Tregs are present in the GI mucosa at time of acute GVHD onset [Lord, J D, et al. (2011) Biol Blood Marrow Transplant. 2011 17(4):486-9]. Moreover, the ratio of Treg/CD4 T-cells was shown to be increased in higher clinical stages of acute GVHD.

As opposed to typical broad immune suppression, selective STAT3 inhibition significantly expanded regulatory T-cells while preserving non-alloreactive effector T-cell function. Rapamycin promotes Treg potency and growth while suppressing conventional T-cells [Zeiser, R, et al. (2008) Blood 111:453-62; Veerapathran, A, et al. (2013) Blood. 122(13):2251-61; Veerapathran, A, et al. (2011) Blood 118:5671-80]. A natural translation of these findings includes GVHD prevention using dual mTOR and STAT3 inhibition. At present, STAT3 may be targeted at multiple signaling levels with available pharmacologic agents. This includes relevant cytokine inhibition (such as IL-6 or IL-23) [Das, R, et al. (2010) Blood 115:5249-58; Pidala, J, et al. (2012) Bone Marrow Transplant 47:747-8], upstream JAK2 blockade [Betts, B C, et al. (2011) Blood 118:5330-9], or direct suppression of STAT3 activation [Betts, B C, et al. (2013) J Leukoc Biol. 2014 95(2):205-13]. One approach is adding ustekinumab [Griffiths, C E, et al. (2010) The New England journal of medicine 362:118-28], a monoclonal antibody targeting the p40-cytokines, to rapamycin. The p40-cytokines include IL-12 and IL-23, where the latter uses a STAT3-dependent signaling mechanism [Das, R, et al. (2010) Blood 115:5249-58; Toichi, E, et al. (2006) J Immunol 177:4917-26; Tonel, G, et al. (2010) J Immunol 185: 5688-91]. While ustekinumab is FDA-approved for the treatment of psoriasis and psoriatic arthritis [Griffiths, C E, et al. (2010) The New England journal of medicine 362: 118-28], it has also demonstrated efficacy in treating refractory GVHD [Pidala, J, et al. (2012) Bone Marrow Transplant 47:747-8].

STAT3 activity and upregulation of RORgammaT are shown to occur early in the post-transplant course. STAT3 Y705 phosphorylation can identify patients at risk to develop acute GVHD prior to clinical recognition of the syndrome. $T_H17$ cells, identified by RORgammaT staining, are shown to be abundant in the target-organs of those diagnosed with severe acute GVHD. Moreover, this burden of $T_H17$ cells is associated with a poor upfront response to standard glucocorticoid therapy. Finally, concurrent blockade of mTOR and STAT3 is shown to efficiently optimize control over RORgammaT expression in human T-cells.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for identifying patients receiving hematopoietic stem cell transplantation (HSCT) who are at risk for developing graft versus host disease (GVHD), comprising assaying a biological sample from the patient for signal transducer and activator of transcription 3 (STAT3) phosphorylation at tyrosine 705 (Y705) residue within CD4+ T-cells, wherein detection of said STAT3 phosphorylation in at least 48% of the CD4+ T-cells is an indication that the patient will develop GVHD when said STAT3 phosphorylation is assayed by an immunoassay comprising an antibody that specifically binds STAT3 phosphorylated at Y705 residue; and administering a therapeutically effective amount of an inhibitor of STAT3 to patients with said STAT3 phosphorylation in at least 48% of the CD4+ T-cells, wherein the inhibitor of STAT3 inhibits phosphorylation of the STAT3 Y705 residue.

2. The method of claim 1, wherein the inhibitor of STAT3 is a small molecule, protein, or oligonucleotide.

3. The method of claim 1, wherein the STAT3 inhibitor comprises S3I-201 (CAS 501919-59-1)

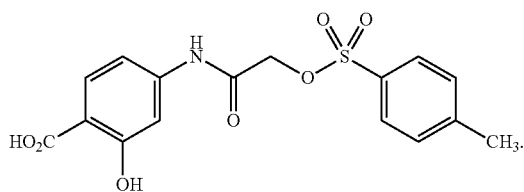 [SMILES: Cc1ccc(S(=O)(=O)OCC(=O)Nc2ccc(C(=O)O)c(O)c2)cc1]

4. The method of claim 1, wherein the STAT3 inhibitor comprises Stattic (CAS 19983-44-9)

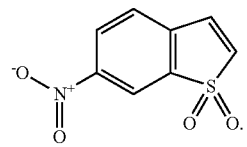

5. The method of claim 1, wherein STAT3 inhibitor increases the ratio of CD4+ Tregs to CD8+ alloreactive T effectors.

6. The method of claim 1, wherein STAT3 inhibitor suppresses $T_H17$ differentiation.

7. The method of claim 1, wherein STAT3 inhibitor promotes the differentiation of induced regulatory T cells (Tregs).

8. The method of claim 1, further comprising administering to the patient a therapeutically effective amount of a mammalian receptor of rapamycin (mTOR) inhibitor.

9. The method of claim 8, wherein the mTOR inhibitor is rapamycin, temsirolimus, everolimus, ridaforolimus, pimecrolimus, merilimus, zotarolimus, TOP216, TAFA93, or nab-rapamycin.

10. The method of claim 1, further comprising administering to the patient a therapeutically effective amount of tacrolimus.

11. The method of claim 1, wherein the biological sample comprises peripheral blood mononuclear cells (PBMC).

12. The method of claim 1, further comprising pulsing the CD4+ T-cells with IL-6 to stimulate STAT3 phosphorylation prior to assaying for STAT3 phosphorylation.

* * * * *

UNITED STATES PATENT AND TRADEMARK OFFICE
CERTIFICATE OF CORRECTION

| | |
|---|---|
| PATENT NO. | : 11,406,707 B2 |
| APPLICATION NO. | : 15/117913 |
| DATED | : August 9, 2022 |
| INVENTOR(S) | : Brian Betts |

It is certified that error appears in the above-identified patent and that said Letters Patent is hereby corrected as shown below:

In the Specification

In Column 1, Lines 10-16, the government support clause should read as:
This invention was made with Government support under Grant Nos. CA132197 and HL116547 awarded by the National Institutes of Health. The Government has certain rights in the invention.

Signed and Sealed this
Twenty-second Day of November, 2022

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 28
<212> TYPE: DNA
<213> ORGANISM: Artificial Sequence
<220> FEATURE:
<223> OTHER INFORMATION: Synthetic Construct

<400> SEQUENCE: 1
gttttcgatt tgtttagatt ttttcgtt                                    28

<210> SEQ ID NO 2
<211> LENGTH: 25
<212> TYPE: DNA
<213> ORGANISM: Artificial Sequence
<220> FEATURE:
<223> OTHER INFORMATION: Synthetic Construct

<400> SEQUENCE: 2
cctcttctct tcctccgtaa tatcg                                       25

```
<210> SEQ ID NO 3
<211> LENGTH: 22
<212> TYPE: DNA
<213> ORGANISM: Artificial Sequence
<220> FEATURE:
<223> OTHER INFORMATION: Synthetic Construct

<400> SEQUENCE: 3
atggcggtcg gatgcgtcgg gt                                          22

<210> SEQ ID NO 4
<211> LENGTH: 28
<212> TYPE: DNA
<213> ORGANISM: Artificial Sequence
<220> FEATURE:
<223> OTHER INFORMATION: Synthetic Construct

<400> SEQUENCE: 4
gtttttgatt tgtttagatt tttttgtt                                    28

<210> SEQ ID NO 5
<211> LENGTH: 25
<212> TYPE: DNA
<213> ORGANISM: Artificial Sequence
<220> FEATURE:
<223> OTHER INFORMATION: Synthetic Construct

<400> SEQUENCE: 5
cctcttctct tcctccataa tatca                                       25

<210> SEQ ID NO 6
<211> LENGTH: 22
<212> TYPE: DNA
<213> ORGANISM: Artificial Sequence
<220> FEATURE:
<223> OTHER INFORMATION: Synthetic Construct

<400> SEQUENCE: 6
atggtggttg gatgtgttgg gt                                          22

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ctgctgagaa ggacagggag                                             20

<210> SEQ ID NO 8
<211> LENGTH: 18
<212> TYPE: DNA
<213> ORGANISM: Artificial Sequence
<220> FEATURE:
<223> OTHER INFORMATION: Synthetic Construct

<400> SEQUENCE: 8
agttctgctg acgggtgc                                               18

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 9
accacagtcc atgccatcac                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
tccaccaccc tgttgctgta                                              20
```